United States Patent
Singh

(10) Patent No.: US 12,385,100 B2
(45) Date of Patent: Aug. 12, 2025

(54) METHODS AND COMPOSITIONS FOR DETECTING VIRULENT AND AVIRULENT *Escherichia coli* strains

(71) Applicant: The Florida State University Research Foundation, Inc., Tallahassee, FL (US)

(72) Inventor: Prashant Singh, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 570 days.

(21) Appl. No.: 17/185,077

(22) Filed: Feb. 25, 2021

(65) Prior Publication Data
US 2021/0292816 A1 Sep. 23, 2021

Related U.S. Application Data

(60) Provisional application No. 63/089,155, filed on Oct. 8, 2020, provisional application No. 62/981,224, filed on Feb. 25, 2020.

(51) Int. Cl.
*C12Q 1/689* (2018.01)
(52) U.S. Cl.
CPC ....... *C12Q 1/689* (2013.01); *C12Q 2600/158* (2013.01)
(58) Field of Classification Search
CPC .............. C12Q 1/689; C12Q 2600/156; C12Q 2600/166
See application file for complete search history.

(56) References Cited

U.S. PATENT DOCUMENTS

| | | | |
|---|---|---|---|
| 8,900,809 B1 * | 12/2014 | Bono | C12Q 1/689 435/6.1 |
| 10,190,177 B2 | 1/2019 | Mustapha et al. | |
| 2014/0005061 A1 * | 1/2014 | Tebbs | C12Q 1/689 435/6.12 |
| 2023/0227921 A1 * | 7/2023 | Singh | C12Q 1/686 435/6.15 |

OTHER PUBLICATIONS

Bardasi, L., Taddei, R., Fiocchi, I., Pelliconi, M.F., Ramini, M., Toschi, E., Merialdi, G., 2017. Shiga Toxin-Producing *Escherichia coli* in Slaughtered Pigs and Pork Products. Ital J Food Saf 6. https://doi.org/10.4081/ijfs.2017.6584.

Boer, E. D., & Heuvelink, A. E. (2000). Methods for the detection and isolation of Shiga toxin-producing *Escherichia coli*. Journal of Applied Microbiology, 88(S1), 133S-143S. https://doi.org/10.1111/j.1365-2672.2000.tb05341.x.

(Continued)

*Primary Examiner* — Diana B Johannsen
(74) *Attorney, Agent, or Firm* — Meunier Carlin & Curfman LLC

(57) ABSTRACT

Disclosed herein are methods for detecting virulent Shiga toxin-producing *E. coli* (STEC) strains O26, O103, O121, and O111 in a biological sample comprising the steps of: (i) enriching the bacterial concentration of the biological sample to result in an enriched sample; (ii) isolating DNA from said enriched biological sample; and (iii) detecting virulent strain in said isolated DNA sample via real-time PCR and a melt curve assay. Also disclosed are primers for said assay, as well as kits comprising said primers.

12 Claims, 9 Drawing Sheets

Specification includes a Sequence Listing.

Normalized melting peaks

(56) References Cited

OTHER PUBLICATIONS

Bosilevac, J.M., Dwivedi, H.P., Chablain, P., Ullery, M., Bailey, U.S., Dutta, V., 2019. Comparative Performance Evaluation of Real-Time PCR and Dual-Labeled Fluorescence Resonance Energy Transfer Probe-Based Melt Peak Analysis for the Detection of *Escherichia coli* O157:H7 in Beef Products. J. Food Prot. 82, 507-512. https://doi.org/10.4315/0362-028X.JFP-18-366.

Bosilevac, J.M., Koohmaraie, M., 2012. Predicting the Presence of Non-O157 Shiga Toxin-Producing *Escherichia coli* in Ground Beef by Using Molecular Tests for Shiga Toxins, Intimin, and O Serogroups. Appl Environ Microbiol 78, 7152-7155. https://doi.org/10.1128/AEM.01508-12.

Brichta-Harhay, D.M., Guerini, M.N., Arthur, T.M., Bosilevac, J.M., Kalchayanand, N., Shackelford, S.D., Wheeler, T.L., Koohmaraie, M., 2008. *Salmonella* and *Escherichia coli* O157:H7 Contamination on Hides and Carcasses of Cull Cattle Presented for Slaughter in the United States: an Evaluation of Prevalence and Bacterial Loads by Immunomagnetic Separation and Direct Plating Methods. Appl. Environ. Microbiol. 74, 6289-6297. https://doi.org/10.1128/AEM.00700-08.

Centers for Disease Control and Prevention (CDC), 2019. Culture-independent Diagnostic Tests | Food Safety | CDC. URL https://www.cdc.gov/foodsafety/challenges/cidt.html (accessed Dec. 15, 2020).

Etcheverría, A. I., & Padola, N. L. (2013). Shiga toxin-producing *Escherichia coli*. Virulence, 4(5), 366-372. https://doi.org/10.4161/viru.24642.

Feng, P. C., Jinneman, K., Scheutz, F., & Monday, S. R. (2011). Specificity of PCR and serological assays in the detection of *Escherichia coli* Shiga toxin subtypes. Applied and environmental microbiology, 77(18), 6699-6702.

Margot, H., Cernela, N., Iversen, C., Zweifel, C., & Stephan, R. (2013). Evaluation of seven different commercially available real-time PCR assays for detection of Shiga toxin 1 and 2 gene subtypes. Journal of food protection, 76(5), 871-873.

Fratamico, P. M., Bagi, L. K., Cray, W. C., Narang, N., Yan, X., Medina, M., & Liu, Y. (2011). Detection by Multiplex Real-Time Polymerase Chain Reaction Assays and Isolation of Shiga Toxin-Producing *Escherichia coli* Serogroups O26, O45, O103, O111, O121, and O145 in Ground Beef. Foodborne Pathogens and Disease, 8(5), 601-607. https://doi.org/10.1089/fpd.2010.0773.

Gassama, A., Sow, P.S., Fall, F., Camara, P., Philippe, H., Guèye-N'diaye, A., Seng, R., Samb, B., M'Boup, S., Germani, Y., Aïdara-Kane, A., 2001. Ordinary and opportunistic enteropathogens associated with diarrhea in senegalese adults in relation to human immunodeficiency virus serostatus. International Journal of Infectious Diseases 5, 192-198. https://doi.org/10.1016/S1201-9712(01)90069-4.

Hyma, K.E., Lacher, D.W., Nelson, A.M., Bumbaugh, A.C., Janda, J.M., Strockbine, N.A., Young, V.B., Whittam, T.S., 2005. Evolutionary Genetics of a New Pathogenic *Escherichia* Species: *Escherichia albertii* and Related Shigella boydii Strains. Journal of Bacteriology 187, 619-628. https://doi.org/10.1128/JB.187.2.619-628.2005.

Jana, M., Adriana, V., & Eva, K. (2020). Evaluation of DNA Extraction Methods for Culture-Independent Real-Time PCR-Based Detection of Listeria monocytogenes in Cheese. Food Analytical Methods, 13(3), 667-677. https://doi.org/10.1007/s12161-019-01686-2.

Li, F., Li, B., Dang, H., Kang, Q., Yang, L., Wang, Y., Aguilar, Z. P., Lai, W., & Xu, H. (2017). Viable pathogens detection in fresh vegetables by quadruplex PCR. LWT—Food Science and Technology, 81, 306-313. https://doi.org/10.1016/j.lwt.2017.03.064.

Liu, Y., Singh, P., & Mustapha, A. (2018). High-resolution melt curve PCR assay for specific detection of *E. coli* O157:H7 in beef. Food Control, 86, 275-282. https://doi.org/10.1016/j.foodcont.2017.11.025.

Lusk, T. S., Strain, E., & Kase, J. A. (2013). Comparison of six commercial DNA extraction kits for detection of *Brucella* neotomae in Mexican and Central American-style cheese and other milk products. Food Microbiology, 34(1), 100-105. https://doi.org/10.1016/j.fm.2012.11.007.

Majowicz, S.E., Scallan, E., Jones-Bitton, A., Sargeant, J.M., Stapleton, J., Angulo, F.J., Yeung, D.H., Kirk, M.D., 2014. Global Incidence of Human Shiga Toxin-Producing *Escherichia coli* Infections and Deaths: A Systematic Review and Knowledge Synthesis. Foodborne Pathogens and Disease 11, 447-455. https://doi.org/10.1089/fpd.2013.1704.

Melton-Celsa, A.R., 1998. Structure, biology, and relative toxicity of Shiga toxin family members for cells and animals [WWW Document]. URL /paper/Structure%2C-biology%2C-and-relative-toxicity-of-Shiga-Melton-Celsa/e7511a2b2ded5cef25ad388257ce807859f985cc (accessed Jul. 26, 2020).

Nastasijevic, I., Schmidt, J.W., Boskovic, M., Glisic, M., Kalchayanand, N., Shackelford, S.D., Wheeler, T.L., Koohmaraie, M., Bosilevac, J.M., 2020. Seasonal prevalence and characterization of Shiga toxin-producing *Escherichia coli* on pork carcasses at three steps of the harvest process at two commercial processing plants in the US. bioRxiv 2020.07.15.205773. https://doi.org/10.1101/2020.07.15.205773.

Norman, K. N., Strockbine, N. A., & Bono, J. L. (2012). Association of Nucleotide Polymorphisms within the O-Antigen Gene Cluster of *Escherichia coli* O26, O45, O103, O111, O121, and O145 with Serogroups and Genetic Subtypes. Applied and Environmental Microbiology, 78(18), 6689-6703. https://doi.org/10.1128/AEM.01259-12.

Paton, A. W., and J. C. Paton. 1998. Detection and characterization of Shiga toxigenic *Escherichia coli* by using multiplex PCR assays for stx1, stx2, eaeA, enterohemorrhagic *E. coli* hlyA, rfbO111, and rfbO157. J. Clin. Microbiol. 36:598-602.

Quirós, P., Martínez-Castillo, A., Muniesa, M., 2015. Improving Detection of Shiga Toxin-Producing *Escherichia coli* by Molecular Methods by Reducing the Interference of Free Shiga Toxin-Encoding Bacteriophages. Appl. Environ. Microbiol. 81, 415-421. https://doi.org/10.1128/AEM.02941-14.

Sambrook, J., Russell, D.W., 2006. Standard Ethanol Precipitation of DNA in Microcentrifuge Tubes. Cold Spring Harb Protoc 2006, pdb.prot4456.https://doi.org/10.1101/pdb.prot4456.

Scott, J.J., Adam, T.C., Duran, A., Burkepile, D.E., Rasher, D.B., 2020. Intestinal microbes: an axis of functional diversity among large marine consumers. Proceedings of the Royal Society B: Biological Sciences 287, 20192367. https://doi.org/10.1098/rspb.2019.2367.

Singh, P., & Mustapha, A. (2015). Multiplex real-time PCR assays for detection of eight Shiga toxin-producing *Escherichia coli* in food samples by melting curve analysis. International Journal of Food Microbiology, 215, 101-108. https://doi.org/10.1016/j.ijfoodmicro.2015.08.022.

Singh, P., Cubillos, G., Kirshteyn, G., Bosilevac, J.M., 2020. High-resolution melting real-time PCR assays for detection of *Escherichia coli* O26 and O111 strains possessing Shiga toxin genes. LWT 131, 109785. https://doi.org/10.1016/j.lwt.2020.109785.

Singh, P., Liu, Y., Bosilevac, J. M., & Mustapha, A. (2019). Detection of Shiga toxin-producing *Escherichia coli*, stx1, stx2 and *Salmonella* by two high resolution melt curve multiplex real-time PCR. Food Control, 96, 251-259. https://doi.org/10.1016/j.foodcont.2018.09.024.

United States Department of Agriculture (USDA), 2020. Meat Animals Production, Disposition, and Income 2019 Summary. URLhttps://usda.library.cornell.edu/concern/publications/02870v85d.

Untergasser, A., Cutcutache, I., Koressaar, T., Ye, J., Faircloth, B. C., Remm, M., & Rozen, S. G. (2012). Primer3—new capabilities and interfaces. Nucleic Acids Research, 40(15), e115-e115.

USDA, FSIS, 2020a. Detection, Isolation and Identification of Top Seven Shiga Toxin-Producing *Escherichia coli* (STECs) from Meat Products and Carcass and Environmental Sponges. URL https://www.fsis.usda.gov/wps/wcm/connect/7ffc02b5-3d33-4a79-b50c-81f208893204/MLG-5B.pdf?MOD=AJPERES (accessed Dec. 15, 2020).

(56) References Cited

OTHER PUBLICATIONS

USDA, FSIS, 2020b. Cost-Benefit Analysis for FSIS's Implementation of Its Non-O157 STEC Testing on Beef Manufacturing Trimmings and Expansion of Its Testing to Ground Beef and Ground Beef Components Other Than Beef Manufacturing Trimmings. URL https://www.fsis.usda.gov/wps/wcm/connect/c37a7129-639c-41fa-ab75-be6dddcd1c44/FSIS-Non-0157-STEC-Testing-CBA-June-2020.pdf?MOD=AJPERES (accessed Dec. 15, 2020).

Wasilenko, J. L., Fratamico, P. M., Narang, N., Tillman, G. E., Ladely, S., Simmons, M., & Cray, W. C. (2012). Influence of Primer Sequences and DNA Extraction Method on Detection of Non-O157 Shiga Toxin-Producing *Escherichia coli* in Ground Beef by Real-Time PCR Targeting the eae, stx, and Serogroup-Specific Genes. Journal of Food Protection, 75(11), 1939-1950. https://doi.org/10.4315/0362-028X.JFP-12-08.

\* cited by examiner

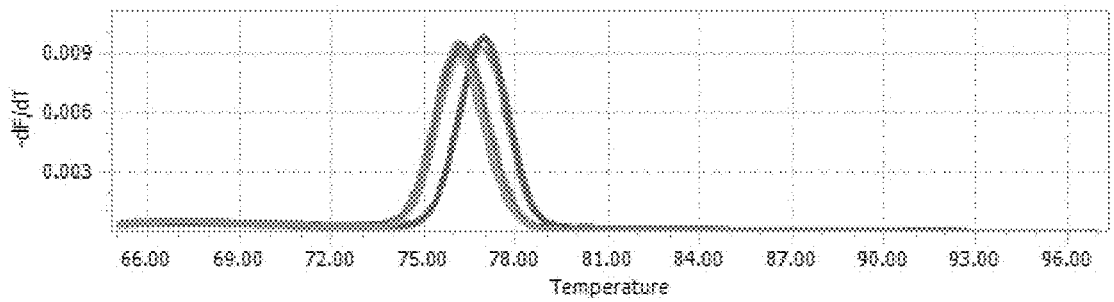
Fig 1a. Melting peaks
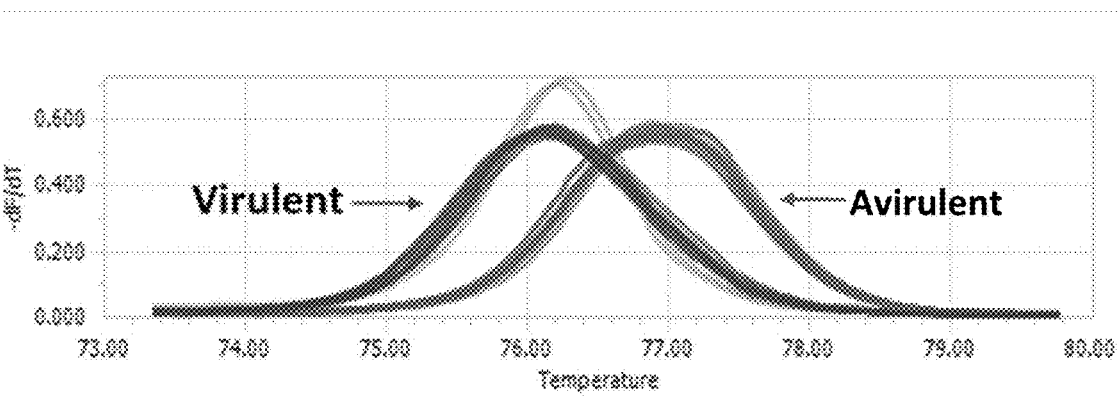
Fig 1b. Normalized melting peaks
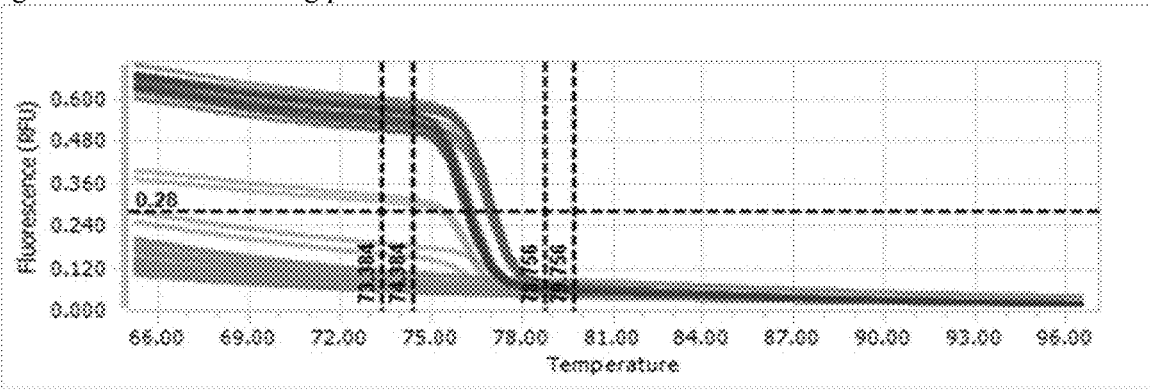
Fig 1c: Melting curves

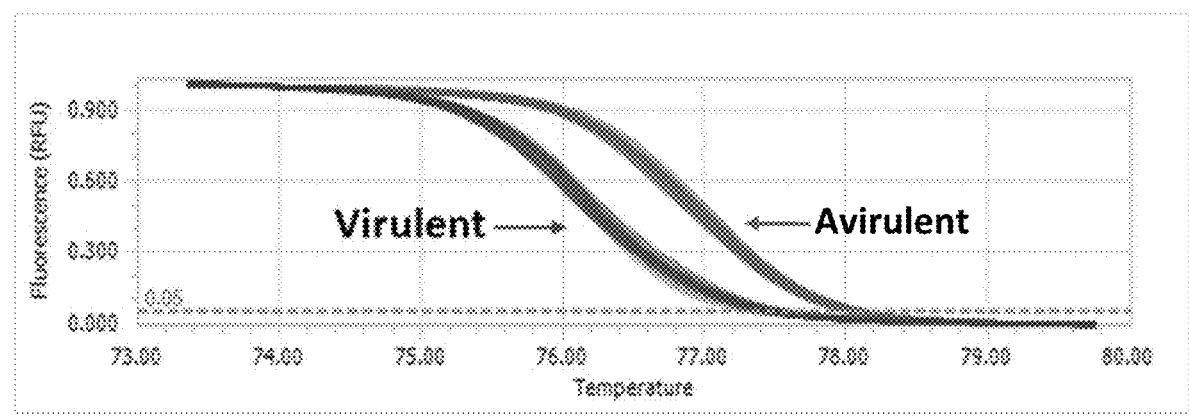
Fig 1d: Normalized melting curves

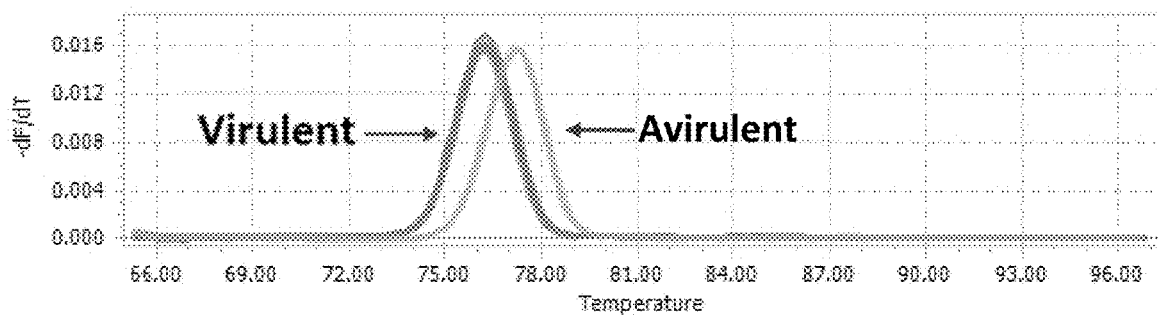
Fig 2a. Melting peaks
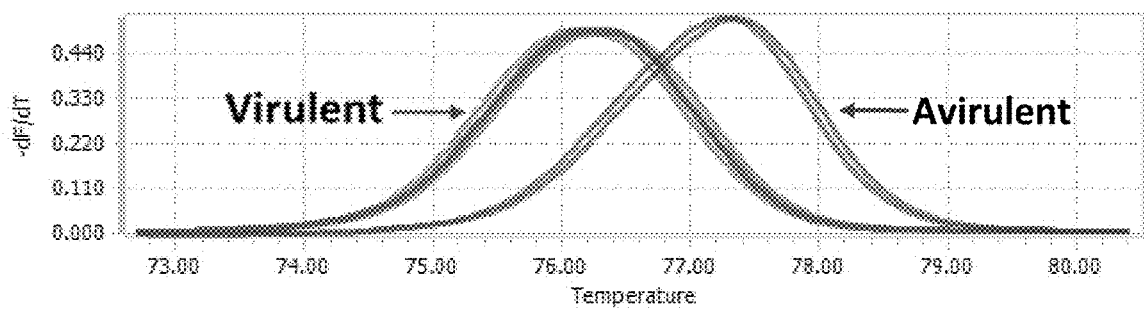
Fig 2b. Normalized melting peaks
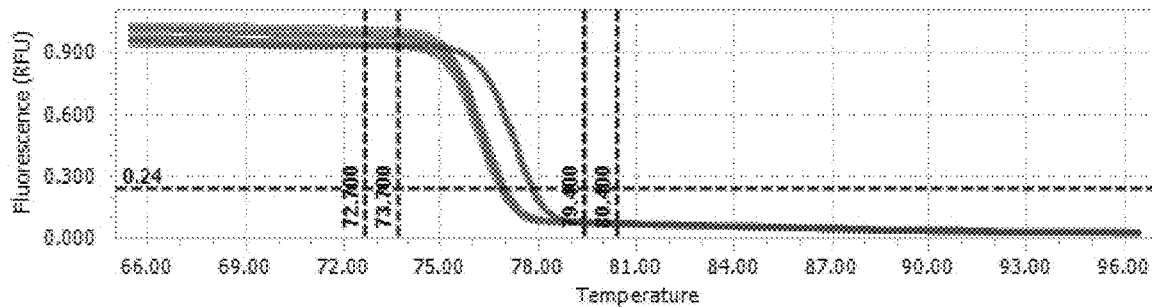
Fig 2c: Melting curves

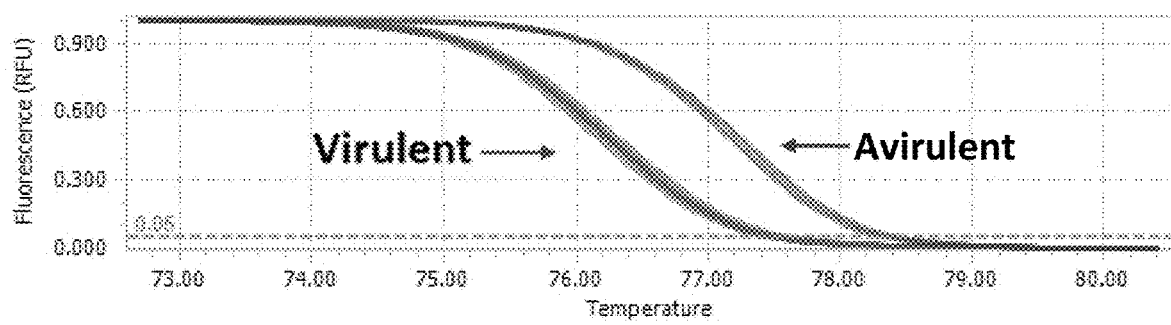
Fig 2d: Normalized melting curves

O26 fnl1
LEFT PRIMER      32  20  60.01  50.00  5.00  0.00 GTGGCACTGGTTCTTTTGGT
RIGHT PRIMER    118  22  58.28  36.36  6.00  2.00 TTTCATCCCTGCTAAATATTCG
SEQUENCE SIZE: 1035
INCLUDED REGION SIZE: 1035

PRODUCT SIZE: 87, PAIR ANY COMPL: 3.00, PAIR 3' COMPL: 0.00
TARGETS (start, len)*: 88,1

```
  1 ATGTTTAAGAATAAAACACTCGTTATCACTGGTGGCACTGGTTCTTTTGGTAATGCCGTA
                                 >>>>>>>>>>>>>>>>>>>>

61 CTTAAGCGTTTTCTAGATACAGATATTACTGAAATACGAATATTTAGCAGGGATGAAAAA
            *          <<<<<<<<<<<<<<<<<<<<<<

121 AAACAAGATGATATGCGGAAAAAATATAATAACTCAAAATTAAAATTTTATATAGGTGAT

181 GTGCGAGACTATAATTCCGTTCTAAATGCAACGCGTGGTGCCGATTTTCTGTATCATGCA

241 GCAGCCCTTAAACAAGTTCCTTCATGTGAATTTCACCCTATGGAGGCGGTTAAGACAAAT

301 GTTCTGGGTACGGAAAATGTTCTGGAGGCTGCTATTGCGAATGGGATTAAACGCGTGGTG
```

FIGURE 3

O111 wbdK
LEFT PRIMER     604  20  60.80  55.00  6.00  2.00 CTTCGAGCTCATGGTTGGAC
RIGHT PRIMER    717  22  57.02  36.36  6.00  2.00 CGACTCTTCGAAAATATCATCA
SEQUENCE SIZE: 1167
INCLUDED REGION SIZE: 1167

PRODUCT SIZE: 84, PAIR ANY COMPL: 5.00, PAIR 3' COMPL: 0.00
TARGETS (start, len)*: 687,1

1 ATGATTACATACCCACTTGCTAGTAATACTTGGGATGAATATGAGTATGCAGCAATACAG

61 TCAGTAATTGACTCAAAAATGTTTACCATGGGTAAAAAGGTTGAGTTATATGAGAAAAAT

121 TTTGCTGATTTGTTTGGTAGCAAATATGCCGTAATGGTTAGCTCTGGTTCTACAGCTAAT

181 CTGTTAATGATTGCTGCCCTTTTCTTCACTAATAAACCAAAACTTAAAAGAGGTGATGAA

241 ATAATAGTACCTGCAGTGTCATGGTCTACGACATATTACCCTCTGCAACAGTATGGCTTA

301 AAGGTGAAGTTTGTCGATATCAATAAAGAAACTTTAAATATTGATATCGATAGTTTGAAA

361 AATGCTATTTCAGATAAAACAAAAGCAATATTGACAGTAAATTTATTAGGTAATCCTAAT

421 GATTTTGCAAAAATAAATGAGATAATAAATAATAGGGATATTATCTTACTAGAAGATAAC

481 TGTGAGTCGATGGGCGCGGTCTTTCAAAATAAGCAGGCAGGCACATTCGGAGTTATGGGT

541 ACCTTTAGTTCTTTTTACTCTCATCATATAGCTACAATGGAAGGGGCTGCGTAGTTACT

601 GATGATGAAGAGCTGTATCATGTATTGTTGTGCCTTCGAGCTCATGGTTGGACAAGAAAT
                             >>>>>>>>>>>>>>>>>>>>
661 TTACCAAAAGAGAATATGGTTACAGGCACTAAGAGTGATGATATTTTCGAAGAGTCGTTT
         *     <<<<<<<<<<<<<<<<<<<<<<

721 AAGTTTGTTTTACCAGGATACAATGTTCGCCCACTTGAAATGAGTGGTGCTATTGGGATA

FIGURE 4

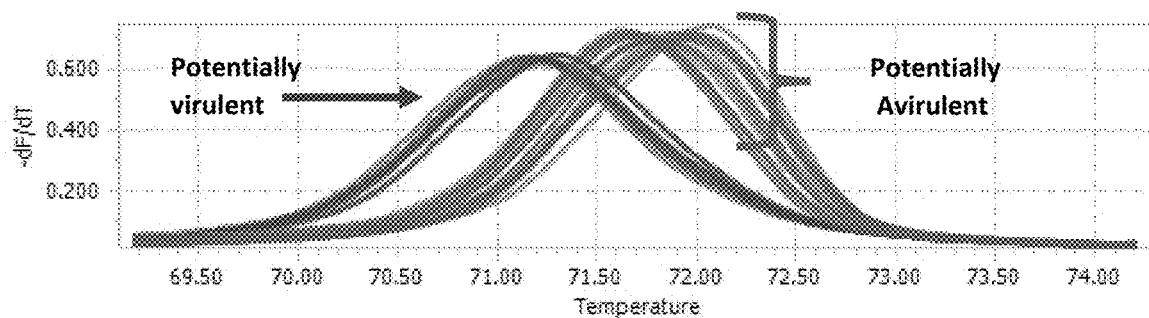
Fig 5a. Normalized melting peaks for O103 HRM assay using pure culture strains.
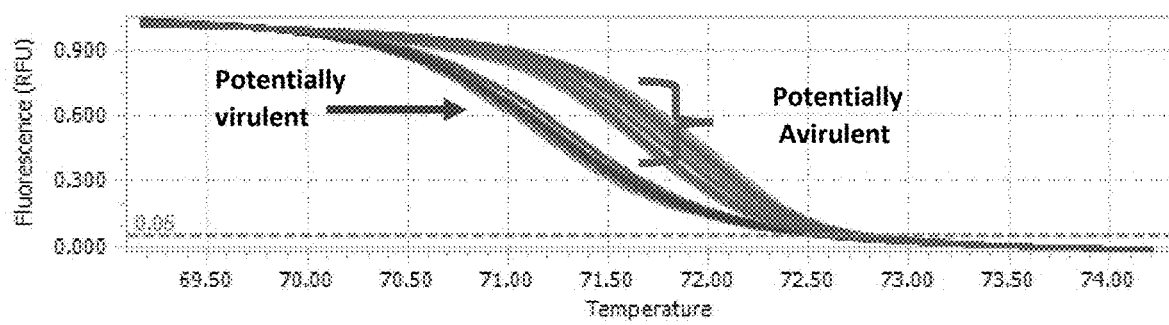
Fig 5b. Normalized melting curves for O103 HRM assay using pure culture strains.
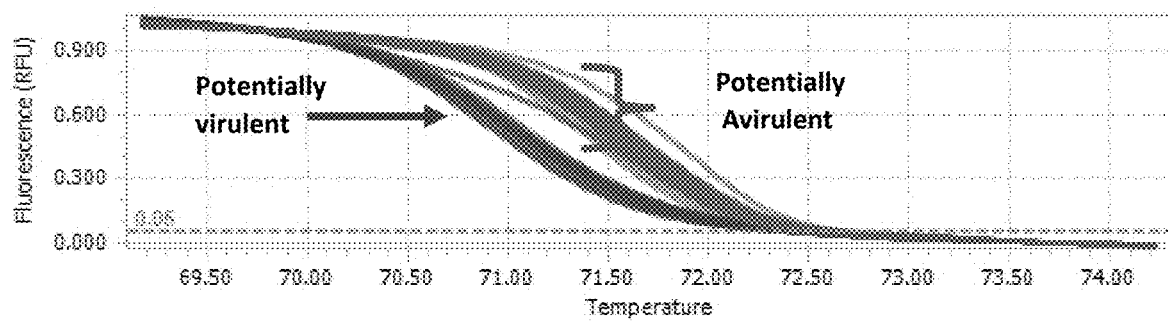
Fig 5C. Normalized melting curves of O103 HRM assay using enriched food samples.
FIGURE 5A-C

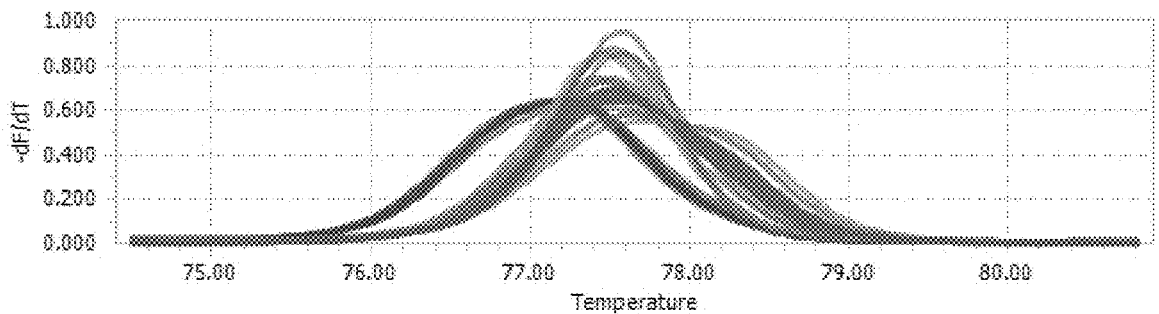
Fig 6a. Normalized melting peaks for O121 HRM assay using pure culture strains.
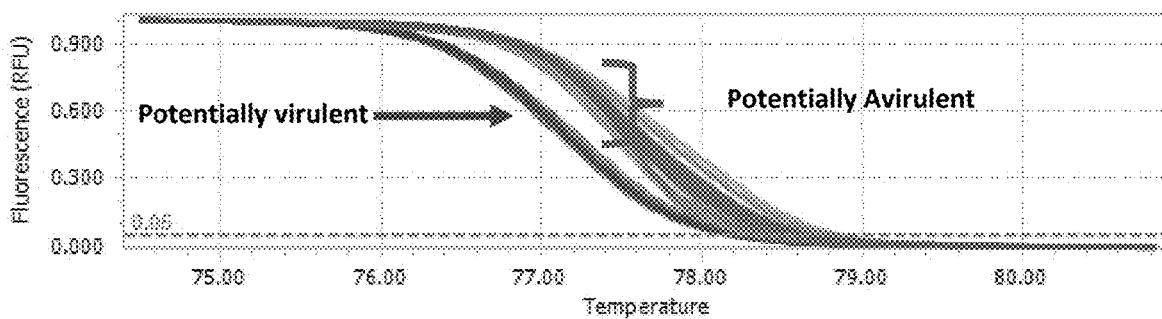
Fig 6b. Normalized melting curves for O121 HRM assay using pure culture strains.
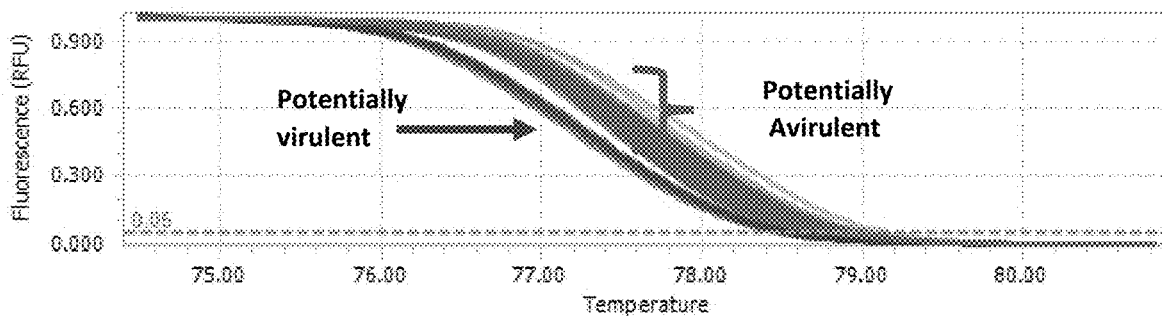
Fig 6C. Normalized O121 melting curves of O121 HRM assay using enriched food samples.
FIGURE 6A-C

METHODS AND COMPOSITIONS FOR DETECTING VIRULENT AND AVIRULENT *Escherichia coli* strains

CROSS-REFERENCE TO RELATED APPLICATIONS

This application claims benefit of U.S. Provisional Application No. 62/981,224, filed Feb. 25, 2020, and U.S. Provisional Application No. 63/089,155 filed Oct. 8, 2020, both of which are hereby incorporated herein by reference in their entirety.

REFERENCE TO SEQUENCE LISTING

The sequence listing submitted on Dec. 18, 2023, as an .txt file entitled "10850-042US1_ST25" created on Oct. 23, 2023, and having a file size of 39,133 bytes is hereby incorporated by reference pursuant to 37 C.F.R. § 1.52 (e) (5).

BACKGROUND

Beef, a major industry, is considered important agricultural commerce in the United States. The US beef agribusiness, at present, is valued at $69 billion (USDA, 2019). As of January 2020, 94.4 million cattle heads were processed, producing approximately 27 billion pounds of beef products (USDA, ERS, 2020). Foodborne pathogens are a common cause of concern for beef products, resulting in costly product recalls. Shiga toxin-producing *Escherichia coli* (STEC) is one of the top foodborne pathogens commonly associated with beef products, and cattle are considered the primary reservoirs for STEC strains. These STEC strains are broadly divided into O157 and non-O157 STEC (USDA, 2020). The top STEC serogroups O157, O26, O121, O103, O145, O45, and O111, are considered adulterants in non-intact beef. Members of these seven STEC serogroups can be further divided into virulent and avirulent strains. The virulent strains of STEC serogroups harbor the stx1, stx2, and eae virulence genes and are pathogenic to humans. These virulent STEC strains can cause different symptoms ranging from bloody diarrhea to renal failure. While the avirulent STEC strains lack significant virulence genes and are usually are unlikely to cause infection. Unlike virulent strains of the top seven STEC serogroups, avirulent strains are more prevalent in the raw meat samples. The presence of these avirulent strains in the raw meat samples constitutes a significant challenge for the testing laboratories in the regulatory agency and beef industry. The presence of avirulent strains in food samples reduces the assay accuracy, resulting in product hold-up for further confirmation by a culture-based method. The Microbiology Laboratory Guidebook (MLG-5C) is the standard method for detecting the top seven STEC serogroups. Based on USDA, FSIS cost-benefit analysis, the currently available STEC detection method has a false positive rate of 81-100%, which results in a loss of around $47 million in raw beef products.

Infection by STEC strains results in bloody diarrhea, hemolytic uremic syndrome and renal failure. According to the CDC, national enteric disease surveillance report *E. coli* O26 and O111 are responsible for 16% and 10.7% of STEC cases, respectively. According to the CDC, national enteric disease surveillance report *E. coli* O121 are responsible for 4.7% of total STEC cases. Previously, single nucleotide polymorphisms (SNPs) in the O-antigen gene has been identified and associated with virulent properties of STEC strains. What is needed in the art is an assay for the differentiation of virulent strains of *E. coli* O26, *E. coli* O121, *E. coli* O103, and *E. coli* O111 from avirulent O26, O111, O103 and O121 strains.

SUMMARY

Disclosed herein is a method for detecting virulent and avirulent Shiga toxin-producing *E. coli* (STEC) strain O26 in a biological sample comprising the steps of: (i) enriching the bacterial concentration of the biological sample to result in an enriched sample; (ii) isolating DNA from said enriched biological sample; and (iii) detecting virulent and avirulent O26 strains in said isolated DNA sample via real-time PCR and a high resolution melt curve assay. Said real-time PCR can comprise at least one primer pair. Said primer pair can comprise SEQ ID NO: 1 and SEQ ID NO: 2. Said real-time PCR can comprise an internal amplification control. Virulent amplicons produced in step (iii) can comprise a melting temperature differing by 1-4° C. from avirulent amplicons in said real-time PCR. Said biological sample can comprise a food or a beverage, such as meat, produce, or juice. Said biological sample can comprise a clinical sample, such as stool, urine, or blood.

Also disclosed is a method for detecting virulent and avirulent Shiga toxin-producing *E. coli* (STEC) strain O111 in a biological sample comprising the steps of: (i) enriching the bacterial concentration of the biological sample to result in an enriched sample; (ii) isolating DNA from said enriched biological sample; and (iii) detecting virulent and avirulent O111 strains in said isolated DNA sample via real-time PCR and a melt curve assay. Said real-time PCR can comprise at least one primer pair, such as SEQ ID NO: 3 and SEQ ID NO: 4. Said real-time PCR can comprise an internal amplification control. The virulent amplicons produced in step (iii) can comprise a melting temperature differing by 1-4° C. from avirulent amplicons in said real-time PCR. The biological sample can comprise a food or a beverage, such as meat, produce, or juice. Said biological sample can comprise a clinical sample, such as stool, urine, or blood.

Disclosed herein is a method for detecting virulent and avirulent Shiga toxin-producing *E. coli* (STEC) strain O103 in a biological sample comprising the steps of: (i) enriching the bacterial concentration of the biological sample to result in an enriched sample; (ii) isolating DNA from said enriched biological sample; and (iii) detecting virulent and avirulent O103 strains in said isolated DNA sample via real-time PCR and a melt curve assay. Said real-time PCR can comprise at least one primer pair. Said primer pair can comprise SEQ ID NO: 7 and SEQ ID NO: 7. Said real-time PCR can comprise an internal amplification control. Virulent amplicons produced in step (iii) can comprise a melting temperature differing by 1-4° C. from avirulent amplicons in said real-time PCR. Said biological sample can comprise a food or a beverage, such as meat, produce, or juice. Said biological sample can comprise a clinical sample, such as stool, urine, or blood.

Also disclosed is a method for detecting virulent and avirulent Shiga toxin-producing *E. coli* (STEC) strain O121 in a biological sample comprising the steps of: (i) enriching the bacterial concentration of the biological sample to result in an enriched sample; (ii) isolating DNA from said enriched biological sample; and (iii) detecting virulent and avirulent O121 in said isolated DNA sample via real-time PCR and a melt curve assay. Said real-time PCR can comprise at least one primer pair, such as SEQ ID NO: 9 and SEQ ID NO: 10. Said real-time PCR can comprise an internal amplification control. The virulent amplicons produced in step (iii) can comprise a melting temperature differing by 1-4° C. from avirulent amplicons in said real-time PCR. The biological sample can comprise a food or a beverage, such as meat, produce, or juice. Said biological sample can comprise a clinical sample, such as stool, urine, or blood.

Further disclosed is an isolated nucleic acid sequence comprising SEQ ID NO: 1, 2, 3, 4, 7, 8, 9, or 10. Disclosed is an isolated nucleic acid sequence comprising at least 90% identity to SEQ ID NO: SEQ ID NO: 1, 2, 3, 4, 7, 8, 9, or 10. Disclosed is an isolated nucleic acid sequence comprising at least 95% identity to SEQ ID NO: 1, 2, 3, 4, 7, 8, 9, or 10. Disclosed is an isolated nucleic acid sequence consisting of SEQ ID NO: SEQ ID NO: 1, 2, 3, 4, 7, 8, 9, or 10. Disclosed is an isolated nucleic acid sequence consisting of at least 90% identity to SEQ ID NO: SEQ ID NO: 1, 2, 3, 4, 7, 8, 9, or 10. Disclosed is an isolated nucleic acid sequence consisting of at least 95% identity to SEQ ID NO: SEQ ID NO: 1, 2, 3, 4, 7, 8, 9, or 10.

Also disclosed herein is a kit comprising a primer pair, wherein the primer pair comprises SEQ ID NO: 1 and SEQ ID NO: 2. Said kit can further comprise additional reagents for amplification.

Disclosed herein is a kit comprising a primer pair, wherein the primer pair comprises SEQ ID NO: 3 and SEQ ID NO: 4. Said kit can further comprise additional reagents for amplification.

Also disclosed herein is a kit comprising a primer pair, wherein the primer pair comprises SEQ ID NO: 7 and SEQ ID NO: 8. Said kit can further comprise additional reagents for amplification.

Disclosed herein is a kit comprising a primer pair, wherein the primer pair comprises SEQ ID NO: 9 and SEQ ID NO: 10. Said kit can further comprise additional reagents for amplification.

Further disclosed is a kit comprising two sets of primer pairs, wherein said primer pairs are selected from the group comprising SEQ ID NOS 1 and 2, SEQ ID NOS: 3 and 4, SEQ ID NOS: 7 and 8; or SEQ ID NOS: 9 and 10. Said kit can further comprise additional reagents for amplification.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE FIGURES

The accompanying drawings, which are incorporated in and constitute a part of this specification, illustrate certain examples of the present disclosure and together with the description, serve to explain, without limitation, the principles of the disclosure. Like numbers represent the same elements throughout the figures.

FIG. 1A-D shows a high resolution melt assay for specific identification of *E. coli* O26 isolates and their differentiation of virulent and avirulent strains: 1*a*. Melting peaks; 1*b*. Normalized melting peaks; 1*c*: Melting curves; 1*d*: Normalized melting curves; 1*e*: Difference plot.

FIG. 2A-D shows a high resolution melt assay for specific identification of *E. coli* O111 isolates and their differentiation of virulent and avirulent strains: 2*a*. Melting peaks; 2*b*. Normalized melting peaks; 2*c*. Melting curves; 2*d*. Normalized melting curves.

FIG. 3 shows forward and reverse primers for O26 (SEQ ID NOS: 1 and 2) as well as where the primer hybridization sites on nucleotides 1-360 of SEQ ID NO: 5 occur, which is the antigen gene cluster for *E. coli* strain O26 fnl1 gene.

FIG. 4 shows forward and reverse primers for O111 (SEQ ID NOS: 3 and 4) as well as where the primer hybridization sites on nucleotides 1-780 of SEQ ID NO: 6 occur, which is the antigen gene cluster for *E. coli* strain O111 wbdK gene.

FIG. 5A-C shows normalized melting information for O103 HRM assay. 5A shows normalized melting peaks for O103 HRM assay using pure culture strains. FIG. 5B shows normalized melting curves for O103 HRM assay using pure culture strains. FIG. 5C shows normalized melting curves of O103 HRM assay using enriched food samples.

FIG. 6A-C shows normalized melting information for O121 HRM. FIG. 6A shows normalized melting peaks for O121 HRM assay using pure culture strains. FIG. 6B shows normalized melting curves for O121 HRM assay using pure culture strains. FIG. 6C shows normalized O121 melting curves of O121 HRM assay using enriched food samples.

DETAILED DESCRIPTION

Figure 7:
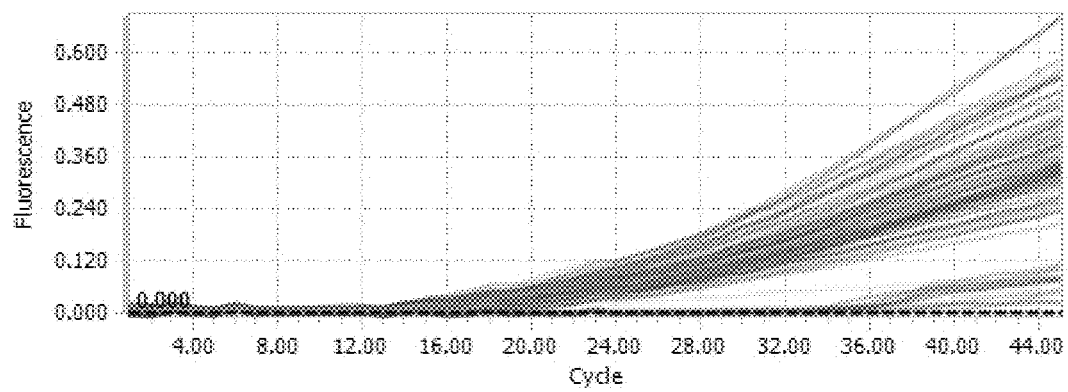
FIG. 7 shows enriched beef samples when tested using LightCycler® 480 High-Resolution Melting Master.
Figure 8:
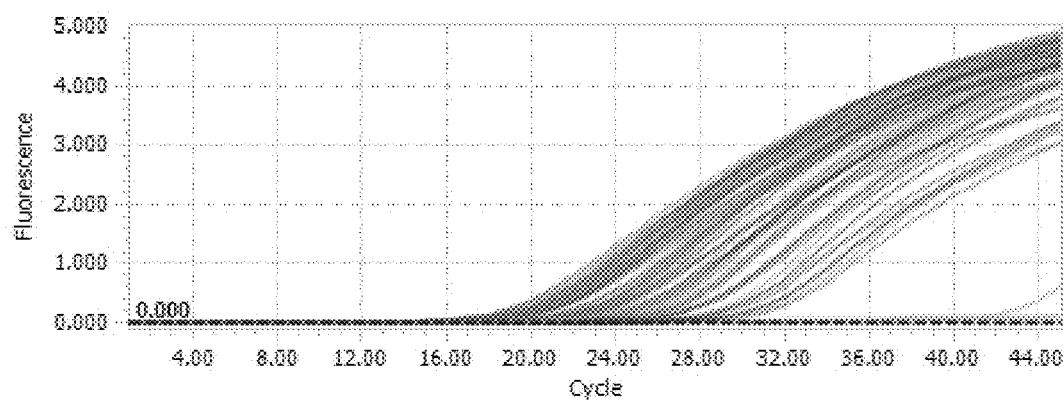
FIG. 8 shows enriched beef samples when tested using Apex qPCR 2× GREEN master mix supplemented with 0.25 μL of 1× EvaGreen.

The following description of the disclosure is provided as an enabling teaching of the disclosure in its best, currently known embodiment. To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Definitions

In this specification and in the claims which follow, reference will be made to a number of terms which shall be defined to have the following meanings:

As used herein, the singular forms "a," "an" and "the" include plural referents unless the context clearly dictates otherwise. Thus, for example, reference to a "metal" includes examples having two or more such "metals" unless the context clearly indicates otherwise.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, "STEC" or "Shiga toxin-producing *Escherichia coli*" refers to a group of *E. coli* strains with the ability to produce Shiga toxin via the expression of stx1 and stx2 genes. STECs are broadly divided into *E. coli* serotype O157 and non-O157 serogroups. Specifically discussed herein are the O26, O121, O103, and O111 strains.

As used herein, "multiplex" refers to refers to the use of PCR to amplify several different DNA targets (genes) simultaneously in a single assay or reaction. Multiplexing can amplify nucleic acid samples, such as genomic DNA, cDNA, RNA, etc., using multiple primers and any necessary reagents or components in a thermal cycler.

As used herein, "enrichment" refers to conditions favoring the growth of a particular microorganism. For example, in one embodiment, a method of the present invention may benefit from an enrichment step whereby bacterial cells or a solution obtained by homogenizing a biological sample and containing one or more target bacterial cells or species are placed in an enrichment medium to allow for the growth of the target bacterial species or strains for the purposes of detection of the bacterial cells or species.

As used herein, the term "subject," "patient," or "organism" includes humans and mammals (e.g., mice, rats, pigs, cats, dogs, and horses). Typical subjects for which methods of the present invention may be applied will be mammals, such as humans. A wide variety of subjects will be suitable for veterinary, diagnostic, research, or food safety applications, e.g., humans; livestock such as cattle, sheep, goats, cows, swine, and the like; poultry such as chickens, ducks, geese, turkeys, and the like; and domesticated animals, particularly pets such as dogs and cats. The term "living subject" refers to a subject as noted above or another organism that is alive.

As used herein, the term "culture media" or "media" refers to liquid, semi-solid, or solid media used to support bacterial cell growth in a non-native environment. Further, by culture media is meant a sterile solution that is capable of sustaining and/or promoting the division or survival of such cells. Suitable culture media are known to one of skill in the art, as discussed herein. The media components may be obtained from suppliers other than those identified herein and may be optimized for use by those of skill in the art according to their requirements. Culture media components are well known to one of skill in the art and concentrations and/or components may be altered as desired or needed.

In certain embodiments, sequences of the present invention, including primer sequences, target sequences and Internal amplification control (IAC) sequences may be identical to the sequences provided here in or comprise less than 100% sequence identity to the sequences provided herein. For instance, primer sequences, target sequences or IAC sequences of the present invention may comprise 90% identity to the sequences provided herein.

The terms "identical" or "percent identity," in the context of two or more nucleic acids or sequences, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., the NCBI web site found at ncbi.nlm.nih.gov/BLAST/or the like). Such sequences are then referred to as "substantially identical." This definition also refers to, or applies to, the compliment of a particular sequence. The definition may also include sequences that have deletions, additions, and/or substitutions. To compensate for gene sequence diversity and to target multiple gene variants of the same genes, degenerated primer pairs (1-2 bases or approximately 5-10% alterations) are allowed. The sequence can comprise or consist of those sequences disclosed herein.

As used herein, the term "nucleic acid" refers to a single or double-stranded polymer of deoxyribonucleotide bases or ribonucleotide bases read from the 5' to the 3' end, which may include genomic DNA, target sequences, primer sequences, or the like. In accordance with the invention, a "nucleic acid" may refer to any DNA or nucleic acid to be used in an assay as described herein, which may be isolated or extracted from a biological sample. The term "nucleotide sequence" or "nucleic acid sequence" refers to both the sense and antisense strands of a nucleic acid as either individual single strands or in the duplex. The terms "nucleic acid segment," "nucleotide sequence segment," or more generally, "segment," will be understood by those in the art as a functional term that includes genomic sequences, target sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

The term "gene" refers to components that comprise bacterial DNA or RNA, cDNA, artificial bacterial DNA polynucleotide, or other DNA that encodes a bacterial peptide, bacterial polypeptide, bacterial protein, or bacterial RNA transcript molecule, introns and/or exons where appropriate, and the genetic elements that may flank the coding sequence that are involved in the regulation of expression, such as, promoter regions, 5' leader regions, 3' untranslated region that may exist as native genes or transgenes in a bacterial genome. The gene or a fragment thereof can be subjected to polynucleotide sequencing methods that determines the order of the nucleotides that comprise the gene. Polynucleotides as described herein may be complementary to all or a portion of a bacterial gene sequence, including a promoter, coding sequence, 5' untranslated region, and 3' untranslated region. Nucleotides may be referred to by their commonly accepted single-letter codes.

The term "recombinant" when used with reference, e.g., to a cell, or nucleic acid indicates that the cell or nucleic acid has been modified by the introduction, by natural or artificial means, of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. In some embodiments, recombinant sequences may also include nucleic acids, proteins, or recombinant genomes, such as bacterial genomes. In certain embodiments, a "recombinant" bacterium or cell may refer to a bacterial cell into which a stx gene or nucleic acid has been inserted, for example by a lambdoid phage, conferring the ability of the bacterial cell to produce shiga toxin.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular electrode is disclosed and discussed and a number of modifications that can be made to the electrode are discussed, specifically contemplated is each and every combination and permutation of the electrode and the modifications that are possible unless specifically indicated to the contrary. Thus, if a class of electrodes A, B, and C are disclosed as well as a class of electrodes D, E, and F and an example of a combination electrode, or, for example, a combination electrode comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Methods and Compositions for Detection of Virulent Strains of *E. coli*

The present invention provides methods for detecting and differentiating between virulent and non-virulent strains of Shiga-toxin producing *Escherichia coli* (STEC) O26, O121, O103, and O111 antigens in a biological sample. Disclosed herein are primers specific for these strains, as well as methods of detecting STEC strains O26, O121, O103, and O111 strains.

STECs are zoonotic pathogens found in the intestinal tract and feces of beef cattle and ruminants, and thus can be introduced into food products of animal origin during slaughter. Beef products contaminated with animal feces have been associated with STEC infections in human. These pathogens have also been reported to contaminate milk, cheese, and other dairy products. STEC infections lead to a variety of illnesses with varying severity, including diarrhea, hemorrhagic colitis (bloody diarrhea), hemolytic uremic syndrome (kidney failure), and death resulting in STEC strains causing human illness to be included as notifiable pathogens to the Nationally Notifiable Diseases Surveillance System in 2000.

STECs are broadly divided into *E. coli* serotype O157 and non-O157 serogroups. In the last decade, the non-O157 serogroup has emerged as a major food-borne pathogen of concern worldwide, responsible for 63%, 74%, 82%, and 80% of the total STEC infections in Canada, Denmark, Germany, and the Netherlands, respectively. To date, a large number of STEC serogroups have been identified, but not all are pathogenic to humans. The frequency of infections of STEC serogroups is variable, with six non-0157 STEC serotypes being most commonly reported: O26 (26%), O103 (22%), O111 (19%), O121 (6%), O45 (5%), and O145 (4%), leading to their classification by the USDA as adulterants (zero tolerance) in non-intact raw beef products.

STECs produce Shiga toxins via the expression of stx1 and stx2 genes, which are transferred to a bacterial cell by lambdoid phages that integrate into the bacterial chromosome. A total of 10 known stx subtypes are presently known. The stx1 and stx2 are further divided into multiple subtypes, in which stx1 has three subtypes (stx1a, stx1c, and stx1d), and stx2 has seven subtypes (stx2a, stx2b, stx2c, stx2d, stx2e, stx2f, and stx2g). Although commercial kits are presently available for identification of Shiga toxin genes, the high genetic diversity of the stx subtypes results in subtypes that may not necessarily be detected by the various assays (Feng et al., Appl Environ Microbiol 77:6699-6702, 2011; Margot et al., J Food Protection 76:871-873, 2013).

In accordance with the invention, both virulent and avirulent strains of O26, O121, O103, and O111 can be specifically and reliably detected in a biological sample. Using the methods described herein, these STECs may be specifically and reliably detected in a biological sample at low concentrations and in minimal time, thus enabling rapid and low-cost simultaneous detection of multiple pathogenic bacteria. Importantly, melting curves can further distinguish between virulent and avirulent strains. For example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0° C. or more difference in the melting peaks can be used to can be used to separate virulent from avirulent strains of O26, O121, O103, and O111. This can be seen in FIGS. 1 and 2.

The methods described herein may be used to test a multitude of biological samples, for example food products. In one embodiment, a biological sample may be meat such as beef, beef stew meat, beef trimmings, chicken, turkey, or the like. A biological sample may also include produce such as various vegetables and fruits, such as alfalfa sprouts, spinach, lettuce, or juices from vegetable or fruits such as apple cider. As used herein, a "biological sample" or "sample" may also include clinical samples such as blood and blood parts including, but not limited to, serum, plasma, platelets, or red blood cells; sputum, mucosa, tissue, cultured cells, including primary cultures, explants, and transformed cells; biological fluids, stool, and urine. A biological sample may also include sections of tissues such as biopsy and autopsy samples, and frozen sections taken for histologic purposes. A biological sample may be obtained from a eukaryotic organism, for example a mammal, including humans, cows, pigs, chickens, turkeys, ducks, geese, dogs, goats, and the like. Any tissue appropriate for use in accordance with the invention may be used, for instance, skin, brain, spinal cord, adrenals, pectoral muscle, lung, heart, liver, crop, duodenum, small intestine, large intestine, kidney, spleen, pancreas, adrenal gland, bone marrow, lumbosacral spinal cord, or blood.

In some embodiments, methods of the present invention may comprise the steps of: i) enriching a bacterial concentration in a test sample by incubating the sample aerobically at approximately 42° C., for instance 37° C., 38° C., 39° C., 40° C., 41° C., 42° C., 43° C., 44° C., or 45° C. in an enrichment media such as described herein; ii) isolating DNA from the enriched sample; and iii) detecting sample DNA using the specific primer sets as described herein.

During the sample enrichment step, a biological sample such as a food sample or other clinical sample, may be collected and diluted in a buffer or media such as water, saline, brain heart infusion broth (BHI), tryptic soy broth (TSB), modified tryptic soy broth (mTSB) or sterile Buffered Peptone Water (BPW), among others. Media useful for culture or enrichment of STECs, *Salmonella*, or other food pathogens in food samples would be known by one of skill in the art. Exemplary media in accordance with the invention may include, but are not limited to, BHI, TSB, mTSB and buffered peptone water (BPW) broth. In some embodiments, a sample as described herein may be diluted at any stage in a desired buffer or solution, for example 1:10, 1:9, 1:8, 1:7, 1:6, 1:5, 1:4, 1:3, 1:2, or 1:1.

Antibiotics may be used in the enrichment of STECs in order to provide a selective advantage for pathogens to grow among any other bacteria present in a food or environmental sample. The use of antibiotics in enrichment broth may hinder the growth of other existing bacteria and simultaneously promote the selective growth of pathogens to be detected in the assay of the present invention. Selection of suitable antibiotics may ensure that the growth of the selected pathogen is not inhibited, thereby ensuring that the sample enrichment time is not lengthened unnecessarily. In some embodiments, antibiotics may be added to a sample or medium such as an enrichment medium or a culture medium. For example, VCC supplement, containing vancomycin, which deters the growth of Gram-positive bacteria, cefixime, which suppresses the growth of *Proteus* spp., and/or cefsulodin, which inhibits *Pseudomonas* spp.; novobiocin, acriflavine, penicillin, streptomycin, chloramphenicol, gentamycin, and the like. Antimycotic compounds may include, but are not limited to Fungizone or other suitable compound. Any of these compounds may be used alone or in combination where appropriate. Any suitable concentration of antibiotic or antimycotic may be used, for example 10 mg/L, 9 mg/L, 8 mg/L, 7 mg/L, etc. In other embodiments, a diluted sample may be homogenized using an appropriate device, such as a Stomacher, for a short time period (such as 2 minutes) in order to release attached cells. The homogenized samples may be incubated aerobically, such as at 42° C. or other temperature suitable for a bacterial strain, for anywhere from 4 to 12 hours to allow for enrichment (recovery and growth of target bacterial species). For example, samples may be incubated for 4 hours, 5 hours, 6 hours, 7 hours, 8 hours, 9 hours, 10 hours, 11 hours, or 12 hours, or 15 hours the like.

During the DNA isolation step as described herein, DNA from an enriched sample may be isolated using any method available as would be known by one of skill in the art. In one embodiment, a commercially available kit, such as Prep-Man® Ultra Sample Preparation Reagent (Applied Biosystems, Life Technologies), or DNeasy® Power Food Microbial Kit (Qiagen, Hilden, Germany) may be used to isolate DNA. According to one embodiment, suspended food particles may be separated from the media, for instance through filtration or centrifugation of the enriched sample, for example at 100×g. The obtained supernatant may then be used for DNA isolation as described herein.

Isolation and Amplification of DNA

Methods such as polymerase chain reaction (PCR and RT-PCR) and ligase chain reaction (LCR) may be used to amplify nucleic acid sequences directly from genomic material, such as genomic DNA, mRNA, cDNA, or from genomic libraries, or cDNA libraries.

In some embodiments, the primers are not labeled, and the amplicons may be visualized, detected, and/or analyzed by real-time PCR using a intercalating dye based approach following their melting temperature, for example by generation of melt curve assays or plots or a dual-labeled probe based approach (i.e., TaqMan, Molecular beacon, Sunrise probe). In other embodiments, an amplicon may be visualized according to size, e.g., using agarose gel electrophoresis. In some embodiments, ethidium bromide staining of the PCR amplicons following size resolution allows visualization of the different size amplicons. Such an approach may be referred to as end-point PCR. Conventional end-point PCR, while suitable for amplification and detection of a target DNA or sequence, may require extensive sample enrichment time due to the higher copy number of target DNA molecules needed for detection. This translates to a higher number of target cells, which, in turn, translates to longer enrichment times. In some embodiments, the primers of the invention may be radiolabeled, or labeled by any suitable means (e.g., using a non-radioactive fluorescent tag), to allow for rapid visualization of amplicons of different sizes following an amplification reaction without any additional labeling step or visualization step.

In accordance with the invention, a PCR assay as described herein may be multiplexed in order to combine multiple reactions into a single assay. For example, a multiplex assay may enable amplification of multiple target sequences using a number of PCR primer pairs, such as one or more primers set forth in the Examples. One of skill in the art will understand that the reaction conditions for each individual reaction in a multiplex assay will necessarily be similar in order to achieve efficient amplification of each target. Optimization or other testing of each individual primer pair may be necessary. For the development of a multiplex PCR assay such as described herein, a large number of primer-pairs has to be tested for each target in order to determine the optimum primer that will produce the best result. Out of multiple PCR primers that work for a particular multiplex assay, a final set of primer pairs for a multiplex assay may be selected based on specific criteria, including, but not limited to, (1) maximum melting temperature difference (at least 2-3° C.) from neighboring peaks; (2) higher PCR amplification efficiency; (3) amplicon size; and (4) size of melt peak formed on the melt curve plot.

In some embodiments, a bacterial species such as a STEC species or serogroups as described herein may be detected based on the level of a particular RNA or DNA in a biological sample. Any of the primers described herein and set forth as SEQ ID NOs: 1-4 or 7-10 may be used for detection, diagnosis, and determination of the presence of such a bacterial species. An amplified nucleotide may then be detected and distinguished for other sequences using techniques described herein.

A PCR assay may include a number of reagents and components, including a master mix and nucleic acid dye or intercalating agent. In some embodiments, an exemplary PCR master mix may contain template genomic material, such as DNA, PCR primers, salts such as $MgCl_2$, a polymerase enzyme, and deoxyribonucleotides. One of skill in the art will be able to identify useful components of a master mix in accordance with the present invention. In one embodiment, a master mix such as MeltDoctor™ HRM Master Mix (Applied Biosystems, Life Technologies), which contains the high resolution melting (HRM) dye, SYTO®9 may be used.

During real-time PCR detection, PCR may be performed in any reaction volume, such as 10 µL, 20 µL, 30 µL, 50 µL, 100 µL, or the like. Reactions may be performed singly, in duplicate, or in triplicate. PCR thermal cycling conditions are well known in the art and vary based on a number of factors. As described herein, an exemplary two-step amplification protocol may include, for example, an initial denaturation at 94° C. for 10 min; 40 cycles of 94° C. for 30 s, 60° C. for 45 s; and a melt curve step performed at the end of the PCR (from 60° C. to 95° C., with gradual temperature increments of 0.04-0.1° C./s). Melt curve plots may be prepared by plotting the negative derivative of fluorescence (-Rn) versus temperature. Mean Tm values for each product may be calculated by averaging the Tm values from duplicate runs of two replications. Any thermal cycling program may be designed as appropriate for use with the particular primers for detection of particular bacterial species as would be understood by one of skill in the art.

Test samples or assays as described herein may be compared to a control or reference sample, such as a positive control, in order to accurately determine the presence and/or amount of a particular pathogen such as a STEC or pathogenic or antibiotic resistant bacterial species. In addition, a reaction control may be used, such as an IAC, in order to avoid false negative results and thereby increase the reliability of an assay. Use of an IAC in a reaction provides assurance that a negative result for a target is truly a negative result rather than due to a problem or break-down in the reaction. Because the signal for the IAC should always be generated, even when the target signal is not generated (i.e., the target organism or DNA is not present in the sample), this would indicate that a negative target signal is indeed a negative result. An IAC may be useful in diagnostic assays because food matrices may harbor inhibitory components that may interfere with PCR amplification, leading to false negative results.

Short oligonucleotides such as an IAC molecule as described herein may be amplified at a much higher amplification efficiency (>100%) and thus may be preferentially amplified in a multiplex PCR reaction. To overcome this issue, an IAC molecule may be added to a multiplex reaction at the lowest possible concentration (10-20 fg), facilitating preferential amplification of the desired target DNA.

Modification of Nucleic Acids

Any number of methods well known to those skilled in the art can be used to isolate and manipulate a DNA molecule. For example, as previously described, PCR technology may be used to amplify a particular starting DNA molecule and/or to produce variants of the starting DNA molecule. DNA molecules, or fragments thereof, can also be obtained by any techniques known in the art, including directly synthesizing a fragment by chemical means. Thus, all or a portion of a nucleic acid as described herein may be synthesized.

As used herein, the term "complementary nucleic acids" refers to two nucleic acid molecules that are capable of specifically hybridizing to one another, wherein the two molecules are capable of forming an anti-parallel, double-stranded nucleic acid structure. In this regard, a nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are known in the art and described by Sambrook, et al. (1989), and by Haymes et al. (1985).

Departures from complete complementarity are permissible, as long as the capacity of the molecules to form a double-stranded structure remains. Thus, in order for a nucleic acid molecule or a fragment of the nucleic acid molecule to serve as a primer or probe, such a molecule or fragment need only be sufficiently complementary in sequence to be able to form a stable double-stranded structure under the particular solvent and salt concentrations employed.

Appropriate stringency conditions that promote DNA hybridization are well known to one of skill in the art and may include, for example, 6× sodium chloride/sodium citrate (SSC) at about 45° C., followed by a wash of 2×SSC at 50° C. The salt concentration in the wash step may be selected from a low stringency of approximately 2×SSC at 50° C. to a high stringency of about 0.2×SSC at 50° C. The temperature in the wash step may be increased from low stringency conditions at room temperature, about 22° C., to high stringency conditions at about 65° C. The temperature and/or salt conditions may be varied as appropriate for optimum results. In accordance with the invention, a nucleic acid may exhibit at least from about 80% to about 100% sequence identity with one or more nucleic acid molecules as described herein, for example at least from about 80%, about 85%, about 90%, about 95%, about 98%, about 99%, or about 100% sequence identity. One of skill in the art will understand that stringency may be altered as appropriate to ensure optimum results.

As used herein, the terms "sequence identity," "sequence similarity," or "homology" are used to describe sequence relationships between two or more nucleotide sequences. The percentage of "sequence identity" between two sequences is determined by comparing two optimally aligned sequences over a specific number of nucleotides, wherein the portion of the sequence in the comparison window may comprise additions or deletions (i.e., gaps) as compared to a reference sequence. Two sequences are said to be identical if nucleotides at every position are the same. A nucleotide sequence when observed in the 5' to 3' direction is said to be a "complement" of, or complementary to, a second nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

SEQ ID NOS: 1-2 and 3-4 set forth particular primer pairs Specifically disclosed are variants of these primers which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Stated another way, disclosed are primers which differ by 1, 2, 3, 4, 5, 6, 7, 8, or 10 nucleotides from SEQ ID NOS: 1-4. Those of skill in the art readily understand how to determine variations that can occur in the primers which still allow for the retention of their functionality.

Detecting the Presence of a Bacterial Species in a Biological Sample

In some embodiments, the oligonucleotides of the invention may be detectably labeled, thereby also functioning as probes. Detectable labels may include, but are not limited to, radiolabels, fluorochromes, including fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxy fluorescein (6-FAM) or N,N,N',N'-tetramethyl-6-carboxyrho-damine (TAMRA); radioactive labels such as 32P, 35S, and 3H), and the like. In some embodiments, a detectable label may involve multiple steps (e.g., biotin-avidin, hapten-anti-hapten antibody, and the like). A primer useful in accordance with the invention may be identical to a particular bacterial target nucleic acid sequence and different from other bacterial sequences. In another embodiment, a primer and/or probe useful in accordance with the invention may enable distinction between a nucleic acid sequence from a virulent and an avirulent STEC strain, such as in O26, O111, O103, and O121.

Diagnostic Tests and Kits

Disclosed are kits that may comprise one or more of the primer pairs disclosed herein. For example, the kit may comprise primers comprising SEQ ID NOS: 1 and 2, or variants thereof. Another kit may comprise primers comprising SEQ ID NOS: 3 and 4, or variants thereof. Another kit may comprise primers comprising SEQ ID NOS: 7 and 8, or variants thereof. Another kit may comprise primers comprising SEQ ID NOS: 9 and 10, or variants thereof. Yet another kit may comprise any combination of these primer pairs, such as SEQ ID NOS: 1-4; SEQ ID NOS: 1-2 and 7-8; SEQ ID NOS: 1-2 and 9-10; SEQ ID NOS: 3-4 and 7-8; SEQ ID NOS: 3-4 and 9-10; SEQ ID NOS: 1-4 and 7-8; SEQ ID NOS: 1-4 and 9-10; SEQ ID NOS: 3-4 and 7-10; or all of SEQ ID NOS: 1-4 and 7-10, or variants thereof. Additional primer sets not included in this list may also be included.

The invention further provides diagnostic reagents and kits comprising one or more such reagents or components for use in a variety of diagnostic assays, including for example, nucleic acid assays, e.g., PCR or RT-PCR assays. Such kits may preferably include at least a first primer pair as described herein, and means for detecting or visualizing amplification of a target sequence. In some embodiments, such a kit may contain multiple primer pairs as described herein for the purpose of performing multiplex PCR or RT-PCR for detection of multiple target sequences. Primer pairs may be provided in lyophilized, desiccated, or dried form, or may be provided in an aqueous solution or other liquid media appropriate for use in accordance with the invention.

Kits may also include additional reagents, e.g., PCR components, such as salts including $MgCl_2$, a polymerase enzyme, and deoxyribonucleotides, and the like, reagents for DNA isolation, or enrichment of a biological sample, including for example media such as water, saline, BHI, TSB, BPW, or the like, as described herein. Such reagents or components are well known in the art. Where appropriate, reagents included with such a kit may be provided either in the same container or media as the primer pair or multiple primer pairs, or may alternatively be placed in a second or additional distinct container into which the additional composition or reagents may be placed and suitably aliquoted. Alternatively, reagents may be provided in a single container means.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1: High-Resolution Melt Assay for Detection of Virulent *E. coli* O26 and O111 Strains Serogroup specific O26 and O111 primers showed 100% specificity. Virulent strains of *E. coli* O26 and O111 formed distinct melt profiles in the normalized and differential melting curves plots. Melt profiles of virulent strains clustered separately and were easily distinguishable from those of avirulent O26 and O111 strains. The O26 assays showed 75% specificity and 100 sensitivity, whereas the O111 assay showed 100% specificity and 100% sensitivity for the identification of virulent strains. The assay developed for specific identification O26 and O111 serogroups and differentiation of positive isolates into virulent and avirulent strains can be used to improve food safety and reduce response time during foodborne outbreaks.

Materials and Methods

Bacterial strains: Virulent and avirulent STEC strains were received from Roman L. Hruska U.S. Meat Animal Research Center (Clay Center, NE, USA). Other bacterial strains were obtained from Florida State University, Food Microbiology Lab Culture collection. Bacterial strains were sub-cultured at 37° C. overnight in Tryptic Soy broth (TSB) (Hardy Diagnostics, Santa Maria, Calif., USA).

Bacterial isolates used (see Table 3): *Acinetobacter pittii* 27B MM, *Acinetobacter schindleri* 27B MC1, *Acinetobacter schindleri* 27B MC2, *Aeromonas hydrophila* 20A MM2, *Alcaligenes faecalis* 22B MC2 1, *Bifidobacterium* bifidum 11863, *Citrobacter freundii* 14B MC1, *Citrobacter freundii* 16B MM1, *E. coli* 25922, *E. coli* O103-1 hSTEC 05, *E. coli* O103-2 MDR 0089 (USMARC_GB_STEC 045), *E. coli* O103-3 March 125B (USMARC_GB_STEC 046), *E. coli* O103 302.1, *E. coli* O103 33, *E. coli* O103 612.1, *E. coli* O103 621.2, *E. coli* O103 745.1, *E. coli* O103 75.2, *E. coli* O103 802.1, *E. coli* O111 C4-462-2_7095, *E. coli* O111 F-A 790.1, *E. coli* O111: H8-hSTEC 08, *E. coli* O111 739.3, *E. coli* O121 2' nphl_12738, *E. coli* O121 211-1, *E. coli* O121 219.5, *E. coli* O121 256-1, *E. coli* O121 3' C4-63-1_3218, *E. coli* O121 4 V2-G2 1-C 16.3, *E. coli* O121 508.3, *E. coli* O121 75.3, *E. coli* O121 785.2, *E. coli* O121 967.1, *E. coli* O145 1 hSTEC 22, *E. coli* O145 170-2, *E. coli* O145, 2 May 109, *E. coli* O145 219.7, *E. coli* O145 3 C4-69-1_3275, *E. coli* O145 317.2, *E. coli* O145 56.2, *E. coli* O145 690.1, *E. coli* O157 221.2, *E. coli* O157 645.V1, *E. coli* O157 766.V1, *E. coli* O157 E0018, *E. coli* O26 16.2, *E. coli* O26 699.1, *E. coli* O26 859.V3, *E. coli* O26 946.1, *E. coli* O26 97.1, *E. coli* O26 hSTEC-03, *E. coli* O26 Imp 133.1, *E. coli* O26 May 063 (USMARC_GB_STEC 021), *E. coli* O45 151.1, *E. coli* O45 219.1, *E. coli* O45 235.1, *E. coli* O45 623.3, *E. coli* O45 978.1, *E. coli* 14B MM, *E. coli* 27A MNC, *Enterobacter hormaechei* 25B MC1, *Enterobacter hormaechei* 25B MC2, *Enterobacter lignolyticus* 15B MC2-1, *Enterobacter lignolyticus* 15B MM1, *Enterococcus faecalis* 15A MNC1, *Enterococcus faecalis* 15B MC2 2, *Klebsiella pneumoniae* 24A MNC2, *Lactobacillus plantarum, Lelliottia amnigena* 15B MC1 1, *Morganella morganii* 15A MNC2, *Morganella morganii* 16B MC1 1, *Obesumbacterium proteus* 17B MM2, *Obesumbacterium proteus* 28A MNC, *Pantoea alhagi* 25A MNC, *Proteus mirabilis* 16B MC1-2, *Proteus mirabilis* 16B MC2 1, *Providencia alcalifaciens* 17B MC2-2, *Salmonella Typhimurium* 14028, *Serratia marcescens* 28B MC2, *Serratia marcescens* 28B MM, *Stenotrophomonas maltophilia* 29B MC1, *Stenotrophomonas maltophilia* 29B MC2, *Vibrio alginolyticus* 18B MC2-1, *Vibrio alginolyticus* 18B MM, *Vibrio fluvialis* 24B MM, *Vibrio parahaemolyticus* 24B MC1 and *Vibrio parahaemolyticus* 24B MC2

DNA extraction: Genomic DNA from overnight cultures were extracted using Extracta DNA Prep for PCR (QantaBio, Beverly, MA, USA). Bacterial cell pellet from one milliliter of bacterial cultures were obtained by centrifugation at 13,000×g for 1 min. Obtained cell pellets were lysed with 50 µl of extraction reagent and heating at 95° C. for 10 minutes on dry bath. Samples were cooled at room temperate for 5 minutes and 50 µl of stabilization buffer was added and samples were centrifuged at 13,000×g for 2 min. Fifty microliters of supernatant containing bacterial DNA was transferred to a new Eppendorf tube. The purity and concentration of isolated DNA were measured by a Nanodrop Lite Spectrophotometer (Thermo Fisher, Wilmington, DE, USA). DNA samples were diluted to 10 ng/µl concentration and used for real-time PCR.

Primer design: The real-time PCR primer for this study was designed using the Primer3 software (Untergasser et al., 2012). Primer-pairs were designed flanking the SNP identified in previous publication (Norman et al., 2012). The specificity and cross-amplification potential of the designed primer-pairs was tested using NCBI/Primer-BLAST tool. All oligonucleotides (Table 1) used in this study were commercially synthesized by IDT (Coraville, IA, USA).

TABLE 1

Primers Used

| Name | Primer sequence | Product Size |
|---|---|---|
| O26 fnl1-32F | 5'-GTG GCA CTG GTT CTT TTG GT-3' (SEQ ID NO: 1) | 87 |
| O26 fnl1-118R | 5'-TTT CAT CCC TGC TAA ATA TTC G-3' (SEQ ID NO: 2) | |
| O111 wbdK-634F | 5'-CTT CGA GCT CAT GGT TGG AC-3' (SEQ ID NO: 3) | 84 |
| O111 wbdK-717R | 5'-CGA CTC TTC GAA AAT ATC A-3' (SEQ ID NO: 4) | |

Real-time PCR: Real-time high-resolution melt assays were performed on LightCycler® 96 real-time PCR instrument (Roche Diagnostics Corp., Indianapolis, USA) with 2× LightCycler® 480 High Resolution Melting Master (Roche Diagnostics Corp., Indianapolis, USA). Additionally, a 10 µl real-time PCR reaction mixture consisted of 20 ng of DNA, 0.5 µM forwards and reverse primers and 2.5 mM $MgCl_2$. A two-step PCR protocol was used for the amplification of target sequence. The amplification protocol consisted of an initial denaturation step at 94° C. for 600 seconds, 40 cycles of 95° C. for 15 s and 62° C. for 30 s. A HRM was performed at the end of the PCR amplification starting from 60° C. to 95° C., with gradual temperature increments of 0.04° C./s (25 reading/° C.). Signal from PCR amplification and HRM were collected in the ResoLight channel of the real-time instrument. HRM analysis for *E. coli* O26 was performed with a pre-melt region 73.3-74.3° C. and a post-melt region 78.7-79.7° C. Whereas, HRM analysis for *E. coli* O111 was performed with a pre-melt region 71.5-72.5° C. and a post-melt region 78.2-79.2° C.

Inoculum preparation and enumeration: Six strains of O26 and four strains of O111 were chosen for inoculating the food samples (Table 2). Each strain was individually cultured at 37° C. in 10 mL TSB (Hardy Diagnostics, Santa Maria, Calif., USA). At end of the incubation period cultures were serially diluted and enumerated on tryptic soya agar (Hardy Diagnostics, Santa Maria, Calif., USA). Broth cultures after enumeration were stored in refrigerator while awaiting the colony counts and TSA plates were aerobically incubated at 37° C. Counts from TSA plates were used to calculate appropriate dilution and volume needed for spiking food samples at 10 CFU. Further, the volume used to spike food sample were spread plated on TSA agar for accurately enumerating the *E. coli* cells used to spike food samples.

TABLE 2

Bacterial strains used for spiking food samples.

| Stab ID | Source | EHEC Pattern |
|---|---|---|
| O26:H11 hSTEC-03 | human | 1 e h |
| O26:H11 Imp 133.1 | beef | 1 e h |
| O26:H11 May 063 (USMARC_GB_STEC 021) | beef | 1 e h |
| O26 16.2 | | |
| O26 97.1 | | espK1 nleB eae nleF |
| O26 699.1 | | nleB eae nleF |
| O111:H8 hSTEC 08 | human | 1 2 e h |

TABLE 2-continued

Bacterial strains used for spiking food samples.

| Stab ID | Source | EHEC Pattern |
|---|---|---|
| O111 C4-462-2_7095 | beef | stx eae |
| O111 F-A 790.1 | beef | 1 e h |

Food sample preparation: Ground beef (12% fat: 88% lean), beef pot roasts, and spinach were purchased from the Costco (Tallahassee, Florida). Beef pot roast were trimmed into thin strips as recommended by USDA N60 sampling protocol. Three hundred and twenty-five grams of beef sample and 25 grams of spinach samples were aseptically transferred in sterile WhirlPak filter stomacher bags (Nasco, Fort Atkinson, WI). Food samples in stomacher bags were individually spiked with 10 CFU/bag using strains of *E. coli* O26 and O111. Spiked food samples were allowed to attach to the food matrix by incubating samples for 15 minutes at room temperature. After attached step spiked food samples were stored at 4° C. for 24 h. At the end of 24 h storage samples beef samples were diluted with 975 mL whereas spinach samples were diluted with 225 mL of TSB with casamino acid and 2 mg/L novobiocin at 37° C. Beef samples were hand messaged and spinach samples were stomached at 230 rpm for 2 min. Food samples after addition of enrichment broth were incubated at 37° C. and samples were collected after 15 h and 21 h enrichment time. DNA from 1.8 mL of enrichment broth were isolated using DNeasy® Power Food Microbial Kit (Qiagen, Hilden, Germany), following manufacturer instructions.

Results and Discussion

Combination of culture, immunological and molecular methods are used for rapid identification of foodborne pathogens. In this study two high resolution melt real-time PCR assays were standardized for specific identification of virulent strains of *E. coli* O26 and O111. The assay developed were initially standardized using pure culture DNA samples. The specificity of developed assays were tested using 87 pure culture isolates which belonged to 19 genera. The specificity of *E. coli* O26 primer pair designed in this correctly identified all *E. coli* O26 isolates.

The HRM melt analysis for O26 assay was performed using a pre-melt region of 73.3 to 74.3° C. and post-melt region of 78.7 to 79.9° C. The sensitivity of HRM analysis was adjusted to 100% discrimination based on delta Tm discrimination. The ability of assay to discriminate between virulent and avirulent strains were tested using 8 O26 strains (16.2, 97.1, 699.1, 859.V3, 946.1, hSTEC-03, Imp 133.1, May 063 (USMARC_GB_STEC 021)). The *E. coli* O26 HRM assay correctly discriminated between all virulent and avirulent strains except *E. coli* O26 97.1 (FIG. 1). This strain clustered with virulent strains. The 97.1 isolate lacked the stx genes and was positive for espK1, nleB, eae and nleF genes. It appears that this isolate (97.1) was a pathogenic isolate, which lost it stx genes at some point of time. This assay can accurately identify O26 isolates and can be used for discrimination of virulent and avirulent strains.

The *E. coli* O111 HRM assay developed showed 100% sensitivity and specificity. The primer designed in this study showed no cross reactivity with any of the 87 isolates spread across 19 genera and accurately identified all O111 isolates. The HRM analysis was performed with sensitivity adjusted to 100% discrimination based on delta Tm discrimination. The O111 isolates tested in this study clustered into two groups (FIG. 2). Four O111 isolates were tested (C4-462-2_7095, F-A 790.1, hSTEC 08 and 739.3) in the culture collection. The assay was accurately able to differentiate between virulent and avirulent strains.

Beef products and fresh produce are frequently associated with STEC outbreaks. Low infective dose (<10 cells) of these STEC strains and their ease of transmission through contaminated food makes them foodborne pathogen of significance concern (Etcheverría & Padola, 2013). Hence, food samples in this study were spiked at ~10 CFU/325 g for beef samples and ~10 CFU/25 g for spinach samples. At the time of spiking food samples, calculated amount of inoculum was spread plated on plate count agar. The inoculum counts for beef and spinach samples ranged between 5 to 19 CFU.

Beef products and fresh produce have high bacterial load, varying fat content and PCR inhibitors making detection of foodborne pathogens at lower concentration a challenging task and necessitating use of enrichment step (Li et al., 2017; Singh et al., 2019; Singh & Mustapha, 2015). The aerobic plate count of spinach, beef trims and ground beef were (5.3-5.5 log CFU/g), (4.5-6.0 log CFU/g) and (5.6-6.0 log CFU/g), respectively. STEC strains (O26: H11 hSTEC-03, O26: H11 Imp 133.1, O26: H11 May 063 (USMARC_GB_STEC 021), O26 16.2, O26 97.1, O26 699.1, O111 C4-462-2_7095 and O111 F-A 790.1) were detected following a 15 h enrichment period. During enrichment of spiked food samples, the food microbiota and spiked pathogen competes with each other for same nutrients. Therefore, food samples with higher microbial load may require longer enrichment time.

Antibiotics (e.g. novobiocin, cefoxitin, vancomycin, cefsulodin) are often added to deter growth of commensal microbiota and facilitate growth of target pathogen (Boer & Heuvelink, 2000). The STEC strains are resistant to these antibiotics, however based on experience these antibiotics can still slowdown growth of STEC strains at recommended concentrations (Singh et al., 2019; Singh & Mustapha, 2015). Therefore, novobiocin was added to enrichment broth at a reduced concentration (2 mg/L).

The PrepMan ultra sample preparation reagent is a commonly used method for isolation of bacterial DNA from enriched food samples (Fratamico et al., 2011; Wasilenko et al., 2012). This DNA isolation method is rapid and results in DNA samples which are suitable for most PCR based foodborne pathogen detection methods. However, the HRM assays are very sensitive to quality of DNA quality. Presence of impurities in DNA samples can interfere with grouping of melt profiles during the HRM analysis step. Therefore, in this study DNeasy PowerFood Microbial Kit was used for isolation of microbial DNA from enriched food samples. Depending on number of samples, DNA isolation process using the DNeasy PowerFood Microbial Kit can take from 4 to 6 h. Nevertheless, the DNeasy PowerFood Microbial Kit results in higher purity DNA which is more suited for HRM assays. Previous studies have shown superior performance of DNeasy PowerFood Microbial Kit over other DNA isolation kit (Jana et al., 2020; Liu et al., 2018; Lusk et al., 2013).

Example 2: Detection of Virulent *E. coli* O103 and O121 Strains

Introduction: Seven virulent strains of Shiga toxin-producing *Escherichia coli* (STEC) are considered as adulterant in non-intact red meat. Infection caused by virulent STEC strains results in bloody diarrhea, hemolytic uremic syndrome, and renal failure. According to the CDC, national enteric disease surveillance report *E. coli* O103 and O121 are responsible for 15.6% and 4.7% of total STEC cases, respectively. Previously, single nucleotide polymorphism (SNP) in the serogroup specific O-antigen gene cluster has been identified and associated with virulent properties of STEC serogroup (Norman et al., 2012).

Purpose: Disclosed herein is a real-time PCR high resolution melting assay for the specific detection of *E. coli* O103 and O121 strains. Further, the high resolution melt profile is used for the differentiation of potentially virulent strains *E. coli* O103 and O121 from avirulent strains.

Methods: Serogroup-specific primers targeting the *E. coli* O103 (wbtD and wbtE genes) and O121 (vioA gene) were designed. A high-resolution melting real-time PCR assay was standardized. The developed for specific identification of O103 and O121 serogroups. The absolute quantification data from the assay was used for the serogroup identification, whereas the grouping obtained after high resolution melt was used for the discrimination of potentially virulent strains from the avirulent strains. The assay was validated using 92 pure culture bacterial DNA samples. Assay were further validated using DNA isolated from enriched beef (n=36) and pork (n=36) samples collected by USDA FSIS.

Results: Both assays when validated using 92 pure culture bacterial DNA samples showed 100% specificity towards their serogroup. High resolution melt data from the pure culture DNA samples showed the potentially virulent strains of *E. coli* O103 and O121 forming a distinct melt profile in the normalized and differential melting curves plots. Based on these specific melt profiles potentially virulent strains can be differentiated from the avirulent strains.

The assay accurately identified all avirulent O121 strains (n=33/72) from the enriched beef and pork samples. The *E. coli* O103 assay identified 17 positive samples among enriched beef and pork samples. The data from the two HRM assay for *E. coli* O103 and O121 was in agreement with the USDA data.

Significance: The assay developed in this study for specific identification O103 and O121 serogroup and differentiation of positive isolates into potentially virulent and avirulent strains can be used to improve food safety and reduce time needed by regulatory agencies for testing food samples.

TABLE 3

*E. coli* Isolates Used for the development and validation of assays: Path-mlg-PCR

| Isolate | O group | stx mlg | ecf | espK1 | nleB | eae | F/sub |
|---|---|---|---|---|---|---|---|
| 16.2 | 26 | 0 | 0 | 0 | 0 | 0 | 0 |
| 222.1 | 26 | 0 |   | 0 | 0 | 0 | 0 |
| 766.1 | 26 | 0 | 0 | 0 | 0 | 0 | 0 |
| 946.1 | 26 | 0 | 0 | 0 | 0 | 0 | 0 |
| 859.V3 | 26 | 0 |   | 0 | 0 | 0 | 0 |
| 3.5 | 45 | 0 | 0 | 0 | 0 | 0 | 0 |
| 151.1 | 45 | 0 |   | 0 | 0 | 0 | 0 |
| 235.1 | 45 | 0 | 0 | 0 | 0 | 0 | 0 |
| 623.3 | 45 | 0 | 0 | 0 | 0 | 0 | 0 |
| 786.1 | 45 | 0 | 0 | 0 | 0 | 0 | 0 |
| 33 | 103 | 0 |   | 0 | 0 | 0 | 0 |
| 75.2 | 103 | 0 | 0 | 0 | 0 | 0 | 0 |
| 302.1 | 103 | 0 | 0 | 0 | 0 | 0 | 0 |
| 621.2 | 103 | 0 | 0 | 0 | 0 | 0 | 0 |
| 802.1 | 103 | 0 | 0 | 0 | 0 | 0 | 0 |
| 739.3 | 111 | 0 | 0 | 0 | 0 | 0 | 0 |
| 75.3 | 121 | 0 |   | 0 | 0 | 0 | 0 |
| 219.5 | 121 | 0 | 0 | 0 | 0 | 0 | 0 |
| 508.3 | 121 | 0 | 0 | 0 | 0 | 0 | 0 |
| 745.1 | 121 | 0 | 0 | 0 | 0 | 0 | 0 |
| 967.1 | 121 | 0 | 0 | 0 | 0 | 0 | 0 |
| 219.7 | 145 | 0 | 0 | 0 | 0 | 0 | 0 |
| 317.2 | 145 | 0 | 0 | 0 | 0 | 0 | 0 |
| 221.2 | O157 | 0 |   | 0 | 0 | 0 | 0 |
| 645.V1 | O157 | 0 | 0 | 0 | 0 | 0 | 0 |
| 766.V1 | O157 | 0 | 0 | 0 | 0 | 0 | 0 |
| 999.V1 | O157 | 0 | 0 | 0 | 0 | 0 | 0 |
| hSTEC-03 | O26 |   |   |   |   |   |   |
| Imp 133.1 | O26 |   |   |   |   |   |   |
| May 063 (USMARC_GB_STEC 021) | O26 |   |   |   |   |   |   |
| C4-462-2_7095 | O111 |   |   |   |   |   |   |
| F-A 790.1 | O111 |   |   |   |   |   |   |
| hSTEC 08 | O111 |   |   |   |   |   |   |

TABLE 4

Avirulent isolates of the top 7 STEC serogroups and HRM assay results

| | | Virulence factors present[a] | | | | | | O26 Assay results | | O111 Assay results | |
|---|---|---|---|---|---|---|---|---|---|---|---|
| Isolate | O group | stx | espK1 | nleB | eae | nleF | subAB | PCR | Vir/Avir | PCR | Vir/Avir |
| 16.2 | O26 | − | − | − | − | − | − | + | Avir | − | − |
| 97.1 | O26 | − | + | + | + | + | − | + | Vir | − | − |
| 699.1 | O26 | − | − | + | + | + | − | + | Avir | − | − |
| 859.V3 | O26 | − | − | − | − | − | − | + | Avir | − | − |
| 946.1 | O26 | − | − | − | − | − | − | + | Avir | − | − |
| hSTEC-03 | O26 | + | − | − | + | − | − | + | Vir | − | − |
| Imp 133.1 | O26 | + | − | − | + | − | − | + | Vir | − | − |
| May063 | O26 | + | − | − | + | − | − | + | Vir | − | − |
| 219.1 | O45 | − | + | + | + | + | − | − | − | − | − |
| 151.1 | O45 | − | − | − | − | − | − | − | − | − | − |
| 235.1 | O45 | − | − | − | − | − | − | − | − | − | − |
| 623.3 | O45 | − | − | − | − | − | − | − | − | − | − |
| 978.1 | O45 | − | + | + | + | + | − | − | − | − | − |
| 33 | O103 | − | − | − | − | − | − | − | − | − | − |

TABLE 4-continued

Avirulent isolates of the top 7 STEC serogroups and HRM assay results

| | | Virulence factors present[a] | | | | | | O26 Assay results | | O111 Assay results | |
|---|---|---|---|---|---|---|---|---|---|---|---|
| Isolate | O group | stx | espK1 | nleB | eae | nleF | sub AB | PCR | Vir/Avir | PCR | Vir/Avir |
| 75.2 | O103 | − | − | − | − | − | − | − | − | − | − |
| 302.1 | O103 | − | − | − | − | − | − | − | − | − | − |
| 612.1 | O103 | − | + | − | + | − | − | − | − | − | − |
| 621.2 | O103 | − | − | − | − | − | − | − | − | − | − |
| 802.1 | O103 | − | − | − | − | − | − | − | − | − | − |
| 739.3 | O111 | − | − | − | − | − | − | − | − | + | Avir |
| C4-462-2_7095 | O111 | + | − | − | + | − | − | − | − | + | Vir |
| F-A 790.1 | O111 | + | − | − | + | − | − | − | − | + | Vir |
| hSTEC08 | O111 | + | − | − | + | − | − | − | − | + | Vir |
| 2014-5-4C | O111 | + | | | | | | | | + | Vir |
| 2016-11-378B2 | O111 | − | | | | | | | | + | Avir |
| 75.3 | O121 | − | − | − | − | − | − | − | − | − | − |
| 219.5 | O121 | − | − | − | − | − | − | − | − | − | − |
| 508.3 | O121 | − | − | − | − | − | − | − | − | − | − |
| 745.1 | O121 | − | − | − | − | − | − | − | − | − | − |
| 785.2 | O121 | + | − | − | − | − | − | − | − | − | − |
| 967.1 | O121 | − | − | − | − | − | − | − | − | − | − |
| 219.7 | O145 | − | − | − | − | − | − | − | − | − | − |
| 317.2 | O145 | − | − | − | − | − | − | − | − | − | − |
| 766.1 | O157 | − | − | − | − | − | − | − | − | − | − |
| 221.2 | O157 | − | − | − | − | − | − | − | − | − | − |
| 645.V1 | O157 | − | − | − | − | − | − | − | − | − | − |
| 999.V1 | O157 | − | − | − | − | − | − | − | − | − | − |

[a]Virulence genes included stx (universal primer set) eae, espK1, nleB, and nleF (Stromberg 2016) to identify avirulent *E. coli* of the 7 most common STEC serogroups.

DNA Sample List

DNA of other bacterial strains used for the assay validation

1. *Acinetobacter pittii*
2. *Citrobacter freundii*
3. *Enterobacter* sp.
4. *Enterobacter* sp.
5. *Acinetobacter pittii*
6. *Acinetobacter* sp.
7. *Acinetobacter pitti*
8. *Acinetobacter* sp.
9. *Acinetobacter calcoaceticus*
10. *Citrobacter freundii*
11. *Vibrio parahaemolyticus*
12. *Morganella morganii*
13. *Citrobacter* sp.
14. *Hafnia paralvei*
15. *Serratia marcescens*
16. *Serratia marcescens*
17. *Enterobacter cloacae*
18. *Enterobacter cloacae*
19. *Klebsiella pneumoniae*
20. *Vibrio parahaemolyticus*
21. *Citrobacter* sp.
22. *Enterobacter faecalis*
23. *Lelliottia amnigena*
24. *Lelliottia amnigena*
25. *Proteus mirabilis*
26. *Proteus mirabilis*
27. *Vibrio alginolyticus*
28. *Vibrio alginolyticus*
29. *Morganella morganii*
30. *Proteus mirabilis*
31. *Morganella morganii*
32. *Aeromonas hydrophila*
33. *Alcaligenes faecalis*
34. *Proteus mirabilis*
35. *Enterobacter hormaechei*
36. *Enterobacter hormaechei*
37. *Acinetobacter schindleri*
38. *Acinetobacter schindleri*
39. *Stenotrophomonas maltophilia*
40. *Stenotrophomonas maltophilia*

Example 3: High-Resolution Melting Assays for the Detection of Virulent Strains of *Escherichia coli* O103 and O121

Shiga toxin-producing *Escherichia coli* (STEC) serogroups O103 and O121 are considered adulterants found in red-meat products. Two high resolution melting assays were standardized to distinguish between potentially virulent and avirulent linage of *E. coli* O103 and O121 strains. The standardized assay was validated using 87 pure culture bacterial DNA samples, naturally contaminated beef (n=84) and pork (n=84) samples collected from the USDA surveillance program, and inoculated beef and spinach samples (n=36). The HRM assays were able to specifically identify the O103 and O121 strains and differentiation between the potentially avirulent or virulent STEC lineages. Data from this study showed greater than percent sensitivity and specificity for the O103 and O121 assays developed in this study.

Materials and Methods

Primer Design

For this study, the serogroup specific primer-pairs were designed using the Primer3 software (Untergasser et al., 2012). The primer pairs used for the specific identification of O103 were intended to target the single nucleotide polymorphism (SNP) located in the wbtD gene at the 937 position (C to T). In comparison, the O121 serogroups were designed to target the SNP in the vioA gene located at the 313 position (C to T). These SNPs have been previously associated with the differentiation of potentially virulent and avirulent strains (Norman et al., 2012). Designed primer-pairs were tested for their specificity and their potential to cross-amplification other serogroups with the NCBI Primer-BLAST tool. The designed oligonucleotides were synthesized by IDT (Coralville, IA, USA). All the oligonucleotides used for this study are listed in Table 5.

TABLE 5

Oligonucleotides for the specific detection of *E. coli* O103 and O121 by the HRM assays.

| Name | Primer Sequence | Target Gene | Product Size |
|---|---|---|---|
| O103-850F | 5'-GATGAAACAAACGGTAAAT-3' (SEQ ID NO: 7) | wbtD | 146 |
| O103-995R | 5'-TTTCATATTTAGCTAACAAGTTT-3' (SEQ ID NO: 8) | | |
| O121-257F | 5'-CAACTGCACACTCCTTGGTC-3' (SEQ ID NO: 9) | vioA | 98 |
| O121-354R | 5'-CGCCTCTTCAATTCTTCTCG-3' (SEQ ID NO: 10) | | |

Real-Time PCR

The HRM assays were performed on a LightCycler® 96 real-time PCR instrument (Roche Diagnostics Corp., Indianapolis, USA). A 2× LightCycler® 480 High-Resolution Melting Master (Roche Diagnostics Corp., Indianapolis, USA) was used for the O121 assay. Whereas Apex qPCR 2× GREEN master mix (Apex Bioresearch, NC, USA) supplemented with 0.25 µL of 1× EvaGreen (Biotium Inc., Hayward, CA, USA) and 1 mM MgCl$_2$ was used for the O103 assay. A typical 10 µl reaction mixture consisted of 20 ng of DNA, 1 µM of forward and reverse primer-pair, 3.0 mM MgCl$_2$, and 0.6 µL of nuclease-free water. A three-step PCR protocol was used for the amplification of the target sequence. The amplification protocol entailed for the O121 assay using 2× LightCycler® 480 High-Resolution Melting Master consisted of an initial denaturation step at 95° C. for 600 s, followed by 40 cycles of denaturation at 95° C. for 15 s, with annealing at 60° C. for 30 s, and extension at 72° C. for 10 s. Whereas the amplification for the O103 assay was performed with an initial denaturation step at 95° C. for 900 s, followed by 40 cycles of denaturation at 95° C. for 15 s, with annealing at 60° C. for 30 s, and extension at 72° C. for 25 s. The HRM step for both assays consisted of a gradual temperature increase of 0.07° C./s from 65 to 97° C. Fluorescence data from the amplification and HRM steps were collected in channel 1 of the instrument. The HRM data for O103 was analyzed with a pre-melt region of 71.9-72.9° C. and a post-melt region of 76.3-77.3° C., while the HRM for O121 was performed with a pre-melt region of 75.5-76.5° C. and a post-melt region of 79.8-80.8° C. Additionally for HRM analysis all negative samples were removed from the analysis.

Bacterial Strains

The specificity of the two HRM assays standardized in this study was validated using DNA isolated from 87 pure bacteria strains (Table 8) as described in Singh et al. 2020.

Assay Validation with Inoculated Food Samples

The performance of the two assays were validated by inoculating the food samples with O103 and O121 strains. Six strains of O103 and O121 were chosen for the inoculation of food samples (Table 1). Each of the strains was individually cultured overnight in 10 mL of tryptic soy broth (TSB) (Hardy diagnostics, Santa Maria, CA, USA). After the incubation, the cultures were serially diluted and spread plated on tryptic soy agar (TSA) (Hardy diagnostics, Santa Maria, CA, USA). The cultures awaiting enumeration were kept in the refrigerator at 4° C., while the PCA plates were incubated at 37° C. overnight. Count from the PCA plates were used to calculate the appropriate dilution and volume to achieve 10 CFU. The computed volume was used to spike the food samples. Additionally, the inoculum was spread plated onto TSA agar to accurately enumerate the inoculation load use to spiked into the food samples.

TABLE 6

*E. coli* strains used for inoculating food samples

| *E. coli* Strain | Source | Virulence Gene |
|---|---|---|
| O103 33 | Beef | stx$^{-ve}$, eae$^{-ve}$ |
| O103 75.2 | Beef | stx$^{-ve}$, eae$^{-ve}$ |
| O103 302.1 | Beef | stx$^{-ve}$, eae$^{-ve}$ |
| O103-1 | Human | stx$_1$, eae |
| O103-2 | Beef | stx$_1$, eae |
| O103-3 | Beef | stx$_1$, eae, |
| O121 75.3 | Beef | stx$^{+ve}$, eae$^{-ve}$ |
| O121 219.55 | Beef | stx$^{-ve}$, eae$^{-ve}$ |
| O121 508.3 | Beef | stx$^{-ve}$, eae$^{-ve}$ |
| O121-2 | Human | stx, eae |
| O121-3 | Beef | stx, eae |
| O121-4 | Beef | stx, eae |

Food Sample Preparation

Ground beef (12% fat 88% lean), beef roast, and spinach were purchased from the local grocery store (Tallahassee, Florida). The beef roast was thinly sliced according to the USDA N60 sampling procedure (USDA 2008). Twenty-five grams of spinach, 325 g of the ground beef, and beef trims were all separately transferred into sterile Whirl-Pak® filter stomacher bags (Nasco, Fort Atkinson, WI). The food samples were individually spiked with one of the 12 strains of *E. coli* O103 and O121 at 10 CFU per bag. The food samples were incubated for 15 minutes at room temperature to facilitate attachment of the inoculum to the food matrix. The inoculated food samples were stored at 4° C. for 24 hours to stress the inoculum. At the end of the 24-hour stressing period, the food samples were diluted with a modified TSB (mTSB) with casamino acid (10 g/L) and 2 mg/L of novobiocin. The 325 g bags of ground beef and beef trims were diluted with 975 ml of the mTSB, while 25 g bags of spinach samples were diluted with 225 ml of the mTSB. The beef bags were lightly massaged after the addition of enrichment broth, whereas the spinach bags were stomached at 230 rpm for 2 minutes. The food samples with enrichment broth were incubated for a 15-hour enrichment at 42° C. After 15 hours, 1.8 mL samples were taken from the enrichment bags and transferred to Eppendorf tubes. DNA from the 1.8 mL of enrichments were isolated using the DNeasy® Power Food Microbial Kit (Qiagen, Hilden, Germany) following the manufacturer's instructions.

Results

Two HRM assays for the specific detection of *E. coli* O103 and O121 serogroups were standardized. The O103 and O121 primer-pairs at first were standardized with pure culture DNA samples. The assay was accurately able to identify all the O103 strains (33, 75.2, 302.1, 612.1 621.2, 745.1, 802.1, O103-1, O103-2, O103-3) tested in the study. The O103 primer-pair did not show any cross-amplification with any other 77 non-target bacteria strains. The O103 primer-pair showed 100% sensitivity and specificity for the specific detection of *E. coli* O103 serogroup. Further, the HRM analysis of samples generating positive amplification correctly differentiated between potentially virulent and avirulent strains lacking crucial virulence genes (FIGS. 5*a* and 5*b*).

Similarly, the O121 HRM assay correctly identified all ten O121 isolates (2' nphl_12738, 211-1, 219.5, 256-1, C4-63-1_3218, V2-G2 1-C 16.3, 508.3, 75.3, 785.2 and 967.1). The O121 HRM analysis of the positive samples was able to show the distinction between the melting plots for the virulent and avirulent strains (FIGS. 6*a* and *b*). The O121 primer-pair did not show any non-specific amplification with any of the other 77 non-target bacteria strains showed 100% sensitivity and specificity with the pure culture strains.

The food samples inoculums used for the spiking food samples ranged from 2 to 11 CFU. The two HRM assays standardized in this study were able to correctly identify the target *E. coli* strains (O103 33, O103 75.2, O103 302.1, O103-1, O103-2, O103-3, O121 75.3, O121 219.5, O121 508.3, 2' nphl_12738, C4-63-1_3218, V2-G2 1-C 16.3) following a 15 h enrichment period. Further, the HRM plots accurately distinguished the virulent and avirulent strains (FIGS. 5*c* and 6*c*).

4. Discussion

The current USDA, FSIS standard method (MLG5) initially screens samples for the presence of stx and eae virulence genes. Samples testing positive for these two virulence genes are further screened for presence of seven *E. coli* serogroups which are considered adulterant. The MLG5 assays in total employs ten primer pairs and 10 dual-labeled probes in a multiplex format for detection of seven STEC serogroups (i.e., O157, O26, O45, O111, O103, O121, and O145). The stx and eae genes are founds in other Gram-negative genera (Margot et al., 2013; Quirós et al., 2015; Gassama et al., 2001; Hyma et al., 2005). This testing approach often results in higher screen positive ($stx^+$, $eae^+$) and potentially positive ($stx^+$, $eae^+$, O-group$^+$) rates (Bosilevac and Koohmaraie, 2012). The reason for this big difference in the potentially positive samples and confirmed STEC strains is likely due to positive results generated by presence of non-pathogenic ($stx^-$, $eae^-$) strains of the big-seven serogroups.

The initial goal was to standardize both assays using one high resolution master mix (i.e., 2× LightCycler® 480 High-Resolution Melting Master). The master mix generated very distinct melt profile for the accurate identification of target SNPs. However, the O103 primer-pair generated poor amplification plots (FIG. 7) in the absolute quantification, making it difficult to call a sample positive or negative based on the Cq values. Initial attempts to optimize the O103 PCR reaction by optimizing primer concentration, reaction conditions, $MgCl_2$ concentrations, primer with locked nucleic acid bases, different HRM master mixes did not result in any significant improvement in the amplification curve. The use of Apex qPCR 2× GREEN master mix supplemented with 0.25 µL of 1× EvaGreen and 1 mM $MgCl_2$ was the only combination which generated a sigmoid amplification plots and acceptable high resolution melting plots. Even though the Apex qPCR 2× GREEN master mix is not a HRM master mix, studies conducted in the laboratory have shown its suitability for the HRM assay (Laxmi Sharma et al., 2020). Further incorporation of EvaGreen and optimization of $MgCl_2$ to the master mix further improved its ability to identify SNP.

Conclusion

Compared to commonly used approach that relies on testing for stx, eae, and serogroup specific genes, a novel approach for the specific identification of potentially virulent strains of O103 and O121 serogroups has been standardized. Application of this approach will help to decrease false-positive rate due to presence of avirulent strains, reduce burden of confirming avirulent strains by regulatory labs and lessen product loss for the stake holders.

Example 4: Multiplex Dual-Labeled 5'-Nuclease Assays for the Detection of Virulent Strains of *Escherichia coli* O26, O111, O103 and O121

Dual-labeled 5'-nuclease assays are considered as a gold standard for the diagnostic assay. A 5'-nuclease assays relies on specific binding of a probe sequence to the target region and thus are more specific than intercalating dye based real-time PCR chemistries. Due to higher target specificity use of probe-based assay is recommended by all major regulatory agencies.

In this study eight dual-labeled probes (Table 7) were designed for the specific identification of potentially virulent and avirulent strains of *E. coli* O26, O111, O103 and O121. The serogroup specific gene target with the SNP was amplified using pre-validated primer-pairs used for the high-resolution melting assays (Table 7). Dual-labeled probes were designed using the Primer3 software (Untergasser et al., 2012). The central three to six bases of the probe sequence flanking the target SNP was replaced by locked nucleic acid (LNA) bases. The LNA bases have excellent ability for discriminating DNA sequences differing by a single base difference, are considered superior to DNA based probes. All probe targeting the potentially virulent genotype were labeled at 3' end with the 6-FAM dye and probes targeting the potentially avirulent genotype were labeled with the HEX dye. The USDA FSIS recommended primer and probe sequence targeting the bacterial 16 rRNA gene sequence was used as an IAC (MLG 5C Appendix 4.00).

A multiplex 5'-nuclease assays was standardized for the specific detection of potentially virulent and avirulent strains of *E. coli* O26, O111, O103 and O121. Each multiplex real-time PCR reaction consisted of serogroup primer pair, two dual-labeled probes, primer amplifying the bacterial 16 rRNA gene sequence and probe detecting the 16 rRNA gene sequence. Multiplex reaction 1 consisted of SEQ ID NO: 1, SEQ ID NO: 2, SEQ ID NO: 11, SEQ ID NO: 12, SEQ ID NO: 19, SEQ ID NO: 20 and SEQ ID NO: 21. Multiplex reaction 2 consisted of SEQ ID NO: 3, SEQ ID NO: 4, SEQ ID NO: 13, SEQ ID NO: 14, SEQ ID NO: 19, SEQ ID NO: 20 and SEQ ID NO: 21. Multiplex reaction 3 consisted of SEQ ID NO: 7, SEQ ID NO: 8, SEQ ID NO: 15, SEQ ID NO: 16, SEQ ID NO: 19, SEQ ID NO: 20 and SEQ ID NO: 21. Multiplex reaction 4 consisted of SEQ ID NO: 9, SEQ ID NO: 10, SEQ ID NO: 17, SEQ ID NO: 18, SEQ ID NO: 19, SEQ ID NO: 20 and SEQ ID NO: 21.

Real-time PCR assays were performed on LightCycler® 96 real-time PCR instrument (Roche Diagnostics Corp., Indianapolis, USA) with 2× Apex qPCR Probe Master Mix (without ROX) (Apex Bio Research Products, NC, USA). A 10 μl real-time PCR reaction mixture consisted of 20 ng of DNA, 500 nM of E. coli O26, O111, O103 and O121 forwards and reverse primers (SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8), 50 nM of probe (SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18), 100 nM of 16S primer (SEQ ID NO: 19, SEQ ID NO: 20), and 50 nM of 16S probe (SEQ ID NO: 21). A three-step PCR protocol was used for the amplification of the target sequence. The amplification protocol for O26, O111, and O121. consisted of an initial denaturation step at 95° C. for 900 seconds, 45 cycles of 95° C. for 20 s, 63° C. for 20 s and 72° C. for 5 s. Whereas, the amplification protocol for O103 consisted of an initial denaturation step at 95° C. for 900 seconds, 45 cycles of 95° C. for 20 s, 55° C. for 20 s and 72° C. for 5 s. Amplification data were collected in the 6-FAM, HEX and CY5 detection channels of the instrument.

TABLE 7

DUAL-LABELED PROBES

| Name | Primer Sequence | Target Gene | Product Size |
|---|---|---|---|
| *E. coli* O26 | | | |
| O26-32F | 5'-GTG GCA CTG GTT CTT TTG GT-3' (SEQ ID NO: 1) | fnl1 | 87 |
| O26-118R | 5'-TTT CAT CCC TGC TAA ATA TTC G-3' (SEQ ID NO: 2) | | |
| O26-Vir-Probe | 5'-6-FAM/CA GAT A+T+T +A+C+T +GAA ATA CG-3'-IABKFQ (SEQ ID NO: 11) | | |
| O26-A Vir-Probe | 5'-HEX/CA GAT A+T+T +G+C+T +GAA ATA CG-3'IABkF (SEQ ID NO: 12) | | |
| *E. coli* O111 | | | |
| O111-634F | 5'-CTT CGA GCT CAT GGT TGG AC-3' (SEQ ID NO: 3) | wbdK | 84 |
| O111-717R | 5'-CGA CTC TTC GAA AAT ATC ATC A-3' (SEQ ID NO: 4) | | |
| O111-Avir-Probe | 5'-HEX/TG GTT ACA G+G+C +ACT AAG AGT-3'-IABKFQ (SEQ ID NO: 13) | | |
| O111-Vir-Probe | 5'-6-FAM/TG GTT ACA G+G+T +ACT AAG AGT-3'-3IABKFQ (SEQ ID NO: 14) | | |
| *E. coli* O103 | | | |
| O103-850F | 5'-GATGAAACAAACGGTAAAT-3' (SEQ ID NO: 7) | wbtD | 146 |
| O103-995R | 5'-TTTCATATTTAGCTAACAAGTTT-3' (SEQ ID NO: 8) | | |
| O103-Avir-Probe | 5'-HEX/AT TAA C+C+T +G+C+A +TAT TAA A-3'-IABKFQ (SEQ ID NO: 15) | | |
| O103-Vir-Probe | 5'-6-FAM/AT TAA C+C+T +G+T+A +TAT TAA A-3'-IABKFQ (SEQ ID NO: 16) | | |
| *E. coli* O121 | | | |
| O121-257F | 5'-CAACTGCACACTCCTTGGTC-3' (SEQ ID NO: 9) | vioA | 98 |
| O121-354R | 5'-CGCCTCTTCAATTCTTCTCG-3' (SEQ ID NO: 10) | | |
| O121-Avir-Probe | 5'-HEX/CG ATA TTG A+T+C +CCA AAA CC-3'-IABKFQ (SEQ ID NO: 17) | | |
| O121-Vir-Probe | 5'-6-FAM/CG ATA TTG A+T+T +CCA AAA CC-3'-IABKFQ (SEQ ID NO: 18) | | |
| 16S RNA IAC | | | |
| 16SRna-F | CCT CTT GCC ATC GGA TGT G (SEQ ID NO: 19) | 16S | 99 |
| 16SRna-R | GGC TGG TCA TCC TCT CAG ACC (SEQ ID NO: 20) | | |
| 16S rRNA Probe | 5'-Cy5-GTG GGG TAA CGG CTC ACC TAG GCG AC-3'-IBRQ (SEQ ID NO: 21) | | |

TABLE 8

List of pure culture strains used for testing specificity of the O103 and O121 HRM assays.

*Acinetobacter pittii* 27B MM
*Acinetobacter schindleri* 27B MC1
*Acinetobacter schindleri* 27B MC2
*Aeromonas hydrophila* 20A MM2
*Alcaligenes faecalis* 22B MC2 1
*Bifidobacterium bifidum* 11863
*Citrobacter freundii* 14B MC1
*Citrobacter freundii* 16B MM1
*E. coli* 25922
*E. coli* O103-1 hSTEC 05
*E. coli* O103-2 MDR 0089 (USMARC_GB_STEC 045)
*E. coli* O103-3 Mar 125B (USMARC_GB_STEC 046)
*E. coli* O103 302.1
*E. coli* O103 33
*E. coli* O103 612.1
*E. coli* O103 621.2
*E. coli* O103 745.1
*E. coli* O103 75.2
*E. coli* O103 802.1
*E. coli* O111 C4-462-2_7095
*E. coli* O111 F-A 790.1
*E. coli* O111:H8-hSTEC 08
*E. coli* O111 739.3
*E. coli* O121 nphl_12738
*E. coli* O121 211-1
*E. coli* O121 219.5
*E. coli* O121 256-1
*E. coli* O121 C4-63-1_3218
*E. coli* O121 V2-G2 1-C 16.3
*E. coli* O121 508.3
*E. coli* O121 75.3
*E. coli* O121 785.2
*E. coli* O121 967.1
*E. coli* O145 1 hSTEC 22
*E. coli* O145 170-2
*E. coli* O145 2 May 109
*E. coli* O145 219.7
*E. coli* O145 3 C4-69-1_3275
*E. coli* O145 317.2
*E. coli* O145 56.2
*E. coli* O145 690.1
*E. coli* O157 221.2
*E. coli* O157 645.V1
*E. coli* O157 766.V1
*E. coli* O157 E0018
*E. coli* O26 16.2
*E. coli* O26 699.1
*E. coli* O26 859.V3

TABLE 8-continued

List of pure culture strains used for testing specificity of the O103 and O121 HRM assays.

*E. coli* O26 946.1
*E. coli* O26 97.1
*E. coli* O26 hSTEC-03
*E. coli* O26 Imp 133.1
*E. coli* O26 May 063 (USMARC_GB_STEC 021)
*E. coli* O45 151.1
*E. coli* O45 219.1
*E. coli* O45 235.1
*E. coli* O45 623.3
*E. coli* O45 978.1
*E. coli* 14B MM
*E. coli* 27A MNC
*Enterobacter hormaechei* 25B MC1
*Enterobacter hormaechei* 25B MC2
*Enterobacter lignolyticus* 15B MC2-1
*Enterobacter lignolyticus* 15B MM1
*Enterococcus faecalis* 15A MNC1
*Enterococcus faecalis* 15B MC2 2
*Klebsiella pneumoniae* 24A MNC2
*Lactobacillus plantarum*
*Lelliottia amnigena* 15B MC1 1
*Morganella morganii* 15A MNC2
*Morganella morganii* 16B MC1 1
*Obesumbacterium proteus* 17B MM2
*Obesumbacterium proteus* 28A MNC
*Pantoea alhagi* 25A MNC
*Proteus mirabilis* 16B MC1-2
*Proteus mirabilis* 16B MC2 1
*Providencia alcalifaciens* 17B MC2-2
*Salmonella* Typhimurium 14028
*Serratia marcescens* 28B MC2
*Serratia marcescens* 28B MM
*Stenotrophomonas maltophilia* 29B MC1
*Stenotrophomonas maltophilia* 29B MC2
*Vibrio alginolyticus* 18B MC2-1
*Vibrio alginolyticus* 18B MM
*Vibrio fluvialis* 24B MM
*Vibrio parahaemolyticus* 24B MC1
*Vibrio parahaemolyticus* 24B MC2

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims.

```
SEQUENCES
SEQ ID NO: 1: O26 fnl1-32F (forward primer):
                                                            (SEQ ID NO: 1)
5'-GTG GCA CTG GTT CTT TTG GT-3'

SEQ ID NO: 2: O26 fnl1-118R (reverse primer):
                                                            (SEQ ID NO: 2)
5'-TTT CAT CCC TGC TAA ATA TTC G-3'

SEQ ID NO: 3 O111 wbdK-634F (forward primer):
                                                            (SEQ ID NO: 3)
5'-CTT CGA GCT CAT GGT TGG AC-3'

SEQ ID NO: 4: O111 wbdK-717R (reverse primer):
                                                            (SEQ ID NO: 4)
5'-CGA CTC TTC GAA AAT ATC A-3'

SEQ ID NO: 5: AY763106.1: O26 Escherichia coli serotype
O26:H11 O-antigen operon, partial sequence:
GCATTAATACCCCTATTAATCAACCTAAGAGCCGCTTATTTCACAGCATGCTCTGAAGT

AATATGGAATAATAAAGTGAAGATACTTGTTACTGGTGGCGCAGGATTTATTGGTTCTG

CTGTAGTTCGTCACATTATAAATAATACGCAGGATAGTGTTGTTAATGTCGATAAATTA
```

-continued

```
ACGTACGCCGGAAACCTGGAATCACTTGCTGATGTTTCTGATTCTGAACGCTATGTTTTT
GAACATGCGGATATTTGCGATGCAGCTGCAATGGCGCGGATTTTTGCTCAGCATCAGCC
GGATGCAGTGATGCACCTGGCTGCTGAAAGCCATGTTGACCGTTCAATTACCGGCCCTG
CGGCATTTATTGAAACCAATATTGTTGGTACTTATGTCCTTTTGGAAGCCGCTCGCAATT
ACTGGTCTGCTCTTGATAGCGACAAGAAAAATAGCTTCCGTTTTCATCATATTTCTACTG
ACGAAGTCTATGGTGATTTGCCTCATCCTGACGAAGTAAATAATACAGAAGAATTACCC
TTATTTACTGAGACGACAGCTTACGCGCCAAGCAGTCCTTATTCCGCATCCAAAGCATC
TAGCGATCATTTAGTCCGCGCGTGGAAACGTACCTATGGTTTACCGACCATTGTGACTA
ACTGTTCGAATAACTACGGCCCTTATCACTTTCCGGAAAAATTGATTCCGCTGGTAATTC
TTAATGCTCTGGAAGGTAAGGCATTACCTATTTATGGCAAAGGGGATCAAATTCGCGAT
TGGCTATATGTTGAAGATCATGCGCGTGCGTTATATACCGTTGTCACCGAAGGTAAAGC
GGGTGAAACTTATAACATTGGCGGACACAACGAAAAGAAAAAACATCGATGTTGTGCTG
ACTATTTGTGATTTGTTGGATGAGATTGTACCGAAAGAGCAATCTTATCGTGAGCAAAT
TACTTATGTTGCCGATCGTCCGGGACACGATCGCCGTTATGCGATTGATGCTGAGAAGA
TTAGCCGCGAATTGGGCTGGAAACCGCAGGAAACGTTTGAGAGCGGGATTCGGAAGAC
AGTGGAATGGTACCTGTCCAATACAAAATGGGTCGAAAATGTGAAAAGTGGTGCCTAT
CAGTCATGGATTGCACAGAACTATGAGGGCCGTCAGTAATGAATATCCTCCTTTTCGGC
AAAACAGGGCAGGTAGGTTGGGAACTACAGCGTGCTCTGGCACCTCTGGGTAATTTGAT
TGCTCTTGATGTTCACTCTACTGATTATTGCGGTGATTTTAGTAATCCTGAAGGTGTAGC
TGAAACCGTAAGAAGCATTCGGCCTGATATTATTGTCAACGCAGCCGCTCACACCGCAG
TAGACAAAGCAGAATCAGAACCGGAGTTTGCACAATTACTTAACGCAACAAGTGTCGA
AGCGATTGCGAAAGCAGCCAATGAAGTCGGCGCCTGGCTTATTCATTACTCGACTGATT
ACGTCTTCCCTGGAAATGGCGATATGCCATGGCGGGAGACGGATGCAACCGCACCACT
AAATGTTTACGGTGAAACCAAGTTAGCCGGAGAAAAAGCGTTACAGGAATATTGCGCA
AAGCATCTTATTTTCCGGACCAGCTGGGTCTATGCAGGAAAAGGAAATAACTTCGCCAA
AACGATGTTACGTCTGGCAAAAGAGCGTGAAGAATTAGCGGTTATTAATGATCAGTTTG
GTGCGCCAACAGGTGCTGAACTGCTGGCTGATTGTACAGCACATGCCATTCGTGTCGCA
CTGAATAAACCAGAAGTCGCAGGCTTGTACCATCTGGTAGCCAGTGGTACCACAACCTG
GCACGATTATGCTGCGCTGGTTTTTGAAGAGGCACGCAAAGCAGGTATTCCCCTTGCAC
TCAACAAGCTCAACGCAGTACCAACAACAGCCTATCCTACACCAGCTCGTCGTCCGCAT
AACTCTCGCCTTAATACAGAAAAATTTCAGCAGAAATTTGCGCTTGTTTTGCCTGATTGG
CAGGTTGGCGTGAAACGAATGCTCAACGAATTATTTACGACTACAGCAATTTAATAGTT
TTTGCATCTTGTTCGTGATGGTGGAGCAAGATGAATTAAAAGGAATGATGAAATGAAAA
CGCGTAAAGGTATTATTTTAGCTGGTGGTTCGGGTACTCGTCTTTATCCTGTAACTATGG
CTGTCAGTAAACAGTTGTTACCGATTTATGATAAACCGATGATCTATTACCCGTTGTCTA
CACTGATGTTAGCGGGTCTTCGCGATATTCTGATTATTAGTACGCCACAGGATACTCCTC
GTTTTCAACAACTGCTGGGTGACGGGAGCCAGTGGGGCTAAATCTTCAGTACAAAGTG
CAACCGAGTCCAGATGGTCTTGCGCAGGCATTTATCATCGGTGAAGAGTTTATCGGTGG
TGATGATTGTGCTTTGGTTCTAGGTGATAATATCTTTTACGGTCACGATCTGCCGAAGTT
AATGGATGTCGCTGTTAACAAAGAAAGTGGTGCAACGGTATTTGCCTATCACGTTAATG
ATCCTGAACGCTACGGTGTCGTTGAGTTTGATAAAAACGGTACGGCGATCAGCCTGGAA
```

-continued

```
GAAAAACCGCTACAACCAAAAAGTAATTATGCGGTAACCGGGCTTTATTTTTATGATAA
CTACGTTGTCGAAATGGCGAAAAATCTTAAGCCTTCTGCCCGCGGTGAACTGGAAATTA
CCGATATTAACCGTATTTATATGGAACAGGGGCGTTTATCCGTTGCCATGATGGGACGT
GGTTATGCATGGCTGGACACGGGGACACATCAAAGTCTTATTGAGGCAAGCAATTTTAT
CGCAACAATAGAAGAACGTCAGGGGCTGAAAGTTTCCTGCCCGGAAGAAATTGCTTAC
CGTAAAGGGTTTATCGATGCTGAGCAGGTGAAAGTATTAGCTGAACCGTTGAAGAAAA
ATGCTTATGGTCAGTATCTGCTGAAAATGATTAAAGGTTATTAATAAAATGAACGTAAT
TAAAACAGAAATTCCAGATGTACTGATTTTTGAACCGAAAGTTTTTGGTGATGAGCGTG
GTTTCTTTATGGAAAGCTTTAATCAGAAAGTTTTTGAAGAAGCTGTAGGGCGGAAGGTT
GAATTTGTTCAGGATAATCATTCTAAATCATCTAAGGGTGTGTTACGCGGACTGCACTA
TCAGCTGGAACCCTATGCTCAAGGTAAATTAGTTCGTTGTGTGGTCGGTGAAGTATTTG
ATGTAGCAGTTGATATTCGTAAATCGTCACCTACATTTGGGAAATGGGTTGGGGTGAAT
TTGTCTGCTGAGAATAAGCGTCAGTTGTGGATCCCTGAGGGGTTTGCGCATGGTTTTTG
GTGTTAAGCGAGATAGCAGAGTTTGTTTATAAGACGACAAATTATTATCATCCTGAATC
AGAAGGTTGCATAAAATGGGATGATTCTTTTTTGATGATTGATTGGCCAAATAAACCGA
TAGCAATCTCAGAAAAAGATAAAAAAGGCTCATCAATTTTGAGGCTAAATGACTATTGA
TGTTGAAAAAAAAACTTCAAAAAATAAAGGAATATCATTCAGTATTGGAGTTGGCAAT
AATTCAGGGTGCGAATGCCATATTTCCTGTGTTGGTATTCCCATTTTTTCTTATTACCTTA
GGGGAAAACATCTTTTCAAGTATTGCTGTTGGTGAAGTACTAGCACTATATGTGCTTAT
ATTTTCGCTATACAGTTTTGATATTATAAGTGTGCAGAAGGTAATTTCAAGTGTGACAA
AAGATGAAATATTTAAAGTTTACATTCTGACACTAATCTGTAGGTTGTGTTTATTTGTTA
TTTCAGGAATATGTCTTTTATTTATAACGTATTTAATTAATAAAACATTAAGTGTATACT
TGGGATTGTTTTTATTGTACCCAGTAGGGATGATATTGCAATCTAATTATTTTTTTCAGG
CTACGAATAACAATAGGCCATTGGCTGTTTTTGTACTAATTGCTCGTGGTATGTCATTAT
GTCTTATTTATTTTTATAATGGACCAGCAGGCTATTTAACAAGTTATTATTATGTCATTT
GTGTGTCTGGTTCGTATTTTTTATCTGGCGTGCTATCGCTTATATATATATATTATCAAAA
TAAGACTAATAAAGCTAAAATTCAATGGGCGGAAATTTTAGAATATATATGCACAGGTT
ATCATCTGTTTATTGCTAATATATTTGTTATTCTATACAGAAATAGTAATATTATTATTCT
TGGCACTCTTGCTTCGCCTGTTGCAACGTCTCTGTACGCGACGGCAGAGAAAATTATTA
AATGTATTCAGTCTATAGCAACCCCGTTAAATCAATACTATTTCACGAGGTTGATAAAG
CAACATGAATTGAAATTAGAACCATACAAAGTTGGAGAATATAAAAGCCTGCTATATG
CAAGCACAAATATTCAGCTAAAGTTCATGGTTTTCATTGTCCTGAGTTTAGGGGGGGTG
GGTACTATATTGGGATATAAGGTTCAAAGTATCGCTGAAATTAGAAGCGCGTTCATCCC
TTTATCAATAATGTCTTTTGCAATATTTATGGGGATATACAATTTTATGTTTGGTTCGGTT
GGATTGTCCATAAGAGGGTATAAAAAAGAATTTTCTTATATAGTGGCCATTACGGGTGT
TTCAACTATTATTTTATCATTATGCCTGAGTTATTTCTTTGCTGAAATAGGCGCTGCAATT
GCTTATGTATTTGCTGAGTTTATCTTACTTATTCTCATACTTAGAATTTATAAAGTGAAA
CGATTATAATTCCCGGTAAGAACTGATAGTGCAAAATCATCATGGCTATAGACTGAATA
AATTGCGGGAAAGAATGTATTACATCATATTTGTGATGGTTTTAGGTTTATGGATTATT
GCATTCAACTACGCTAGAGCAAACAAGCTAAGTAATTTGGTAATTGTGCTTATTATTAC
```

-continued

```
TACTTTATTTATTATTAATAGGCAGAATCAAGACTATGAAGCGTATGTTGATATATTTAA

TGTCAATGAACTTTATGCCGAGATTGGTTATCGCTGGTTAATTTATGGTGTTAAGTATTT

AGGCGGTACCCATGAAGTCATAATTGGCTTGCTGGGTTTATTCCTTGGGACCACATTCCT

ACGATTAATACAATACAGTAAGTATACAGCATTTGGTTTGCTGCTTTACATGTTGTGTCC

AATGCCTATTGACATTGTTCAAATCAGGAATACATTTCTTTTTTTATTTGTCATAAATTCT

CTTATCGAGTTAGAAAAAGAGCATAAATTTAACTCTCTTTGTTTTGTCTTTATGGCACCT

CTTTTCCATAGTTTAGGCATTGTTTATGTATTGGCGTGGGTAATAATCCAATTTCGTACC

TGGAGGGGTTATAATAAGTTAATGGTTTTTGGACTGGTGCTGTCTTTTATTGTAGTGCCA

CTCTTGATTAAAATGTTAATTTTATTATTTAACACTAGGACGTTACATGCATATATAGCT

GATGGCATTAAGGTTCATTCTCTTATTATATGGGCAGGTCCTTATCTTTTTGATCTTTTTC

TGTTATGTTACTTCAGAAAAAAAATAGTAATAACTGATTTACATACTAAACAATGGATT

GATATAATATTCTCGCTAATGTTATTTCTTTCCGTATTTTCACCACTACTTTTATATATCG

ACGAAATAAATAGGATTTTTCGAAATGCGCTATTACTGAAGTATCTGGTAATGATGTCT

ATCGCACAGTATTTAAGTAGACCGACCAGATATATACTTTATTCATATTTACTGTTATTC

ACTTTTGCATTATCAATATATTATACACTCCAAATCGATTATGATTACATTGTATTTGGG

TTACCATACTCATTATGATACTTATGAGGATATATGTTTTATTTTATCTGTGTAAATTATA

ATAACTCTGATTATACAGAAGCATTAATTAAGAGCGTTATTAATCAAGAAAAAGATAGC

TTTGTAATTGTTGTAGATAACTGTTCTAATGAGCAAGAGCTAAAAAAGTTAAATGATAT

TGAGAGTAAATATAACGAGAAGGTCAGATTAATTAAAAGTGATGTGAATTTGGGATATT

TTGGCGGATTGAATCTTGGCCTAAAAGGACTACCAAGAAATCATCCAATAGTTGTTGGG

AATAATGATTTGGTTTATGAGAGTAATTTTACGCAAATAATATCACAGACTACATATCC

GGACGATGCTTTAGTTATTGCTCCAAATGTGATTACAAAGGATGGTTATCACCAGAACC

CACACTGCCGTAAGCGAGTAAGTAAGTTTAGGAAATTTTTGTATGATATATATTTTTCAA

ATTATATCGCTGCTTTAGTTTTAACGTGGGGAAGCAGGTTTTTAAATTATTTGAAAGGTG

GAAGAAATAATTCCTTTGATCAGGGTAGAGGTTATATACATATGGGTATTGGAGCCTGT

TATGTCCTTATGCCTTCCTTCTTCAAATATTTTGATGAATTAGATAACAAAGTTTTTTTAT

ATGGTGAGGAAGCATATTTGGCTGGCCAATTAATGGAAGTAAATGGGAAGATTTTCTAT

GAGCCTGATGCTATTGTCCATCATGAAGAAAGTGCAACTTTGGCGAAAGTTGCTTCTAA

AACAAAATATGGCTATATGAAAAGCTCATATTACGACTATAAAAAATATCTGTAAAAG

GTGAAAATATGTTTAAGAATAAAACACTCGTTATCACTGGTGGCACTGGTTCTTTTGGT

AATGCCGTACTTAAGCGTTTTCTAGATACAGATATTACTGAAATACGAATATTTAGCAG

GGATGAAAAAAACAAGATGATATGCGGAAAAAATATAATAACTCAAAATTAAAATTT

TATATAGGTGATGTGCGAGACTATAATTCCGTTCTAAATGCAACGCGTGGTGCCGATTT

TCTGTATCATGCAGCAGCCCTTAAACAAGTTCCTTCATGTGAATTTCACCCTATGGAGGC

GGTTAAGACAAATGTTCTGGGTACGGAAAATGTTCTGGAGGCTGCTATTGCGAATGGGA

TTAAACGCGTGGTGTGCTTGAGTACCGATAAAGCCGTTTATCCTATCAATGCAATGGGC

ATATCTAAGGCAATGATGGAAAAAGTTATTGTTGCAAAATCACGTAATCTTGACAGTTC

AAAAACAGTTATCTGTGGAACTCGTTATGGAAATGTAATGGCTTCACGTGGATCGGTCA

TCCCATTATTTGTTGATCTAATCAAAGCTGGTAAACCATTGACCATAACCGATCCCAATA

TGACTCGTTTCATGATGACGCTTGAGGATGCTGTCGATCTGGTCCTTTATGCTTTCGAAC

ATGGAAATAATGGTGACATTTTCGTTCAGAAAGCACCTGCGGCAACAATTCAAACATTA
```

-continued

```
GCCATTGCACTTAAGGAATTGCTAAATGCCCATGAGCATCCAATCAATATTATTGGAAC

TCGACACGGGGAAAAACTTTACGAAGCGTTATTGAGCCGAGAGGAAATGATTGCAGCG

GAAGATATGGGTGATTATTATCGTGTTCCACCAGATCTCCGCGATTTGAACTATGGAAA

ATATGTGGAACATGGTGACCGTCGTATCTCGGAAGTGGAAGATTATAATTCTCATAATA

CTGAGAGATTAGATGTTGAGGGAATGAAAGAATTACTGCTAAAACTTCCTTTTATCCGG

GCACTTCGTTCTGGTGAAGATTATGAGTTGGATTCATAATATGAAAATTTTAGTTACTGG

CGCTGCAGGGTTTATCGGTCGAAATTTGGTTTTCCGCCTTAAGGAAGCTGGATATAACG

AACTTATTGCGATAGATCGTAACTCTTCTTTGACGGATTTAGAGCAGGGACTTAAGCAG

GCAGATTTCATTTTTCATCTTGCTGGAGTAAATCGTCCTGTGAAGGAGAGTGAGTTTGA

AGAGGGGAATTGCGATCTAACTCAACAGATTGTTGATATTCTGAAAAAAAATAATAAA

GATACTCCTATCATGCTTAGTTCATCCATCCAAGCTGAATGTGATAACGCTTATGAAA

GAGTAAAGCAGTTGCGGAAAAAATCATTCAGCAGTATGGGGAAACGACAAACGCTAAA

TATTATATTTATCGCTTGCCGAATGTATTCGGTAAGTGGTGTCAACCAAATTATAACTCC

TTTATAGCAACTTTCTGCCATCGCATTGCAAATGATGAAGCTATTACAATTAATGATCCT

TCAGCAGTTGTAAATTTGGTGTATATAGATGACTTTTGTTCTGACATATTAAAGCTATTA

GAAGGAGCGAACGAAACTGGTTACAGGACATTTGGTCCAATTTATTCTGTTACTGTTGG

TGAGGTGGCACAATTAATTTATCGATTTAAAGAAAGTCGCCAAACATTAATCATCGAAG

ATGTAGGTAATGGATTCACTCGAGCATTGTACTCAACATGGTTAAGTTACCTTTCTCCTA

AACAGTTTGCGTATACGGTTCCTTCTTATAGTGATGACAGAGGGGTATTCTGTGAAGTA

TTGAAAACGAAAAACGCGGGCCAGTTTTCGTTTTTTACTGCGCATCCAGGAATTACTCG

GGGGGGGCATTATCATCATTCCAAAAATGAGAAATTTATTATCATCCGAGGAAGTGCTT

GTTTCAAATTTGAAAATATTGTCACGGGTGAACGATATGAACTTAATGTTTCATCAGAT

GATTTTAAAATTGTTGAAACAGTTCCGGGATGGACGCATGACATTACTAATAATGGCTC

GGATGAGCTAGTTGTTATGCTTTGGGCAAATGAAATATTTAATCGTTCTGAACCAGATA

CTATAGCGAGAGTTTTATCGTGAAAAAATTGAAAGTCATGTCGGTTGTTGGGACTCGTC

CAGAAATTATTCGACTCTCGCGTGTCCTTGCAAAATTAGATGAATATTGTGATCACCTTA

TTGTTCATACTGGGCAAAATTACGATTATGAATTGAATGAGGTTTTTTTCAAGGATTTGG

GTGTTCGCAAACCTGATTATTTTCTTAATGCCGCAGGTAAAAATGCAGCAGAGACTATT

GGACAAGTTATCATTAAAGTTGATGAGGTCTTTGAACAGGAAAAACCAGAAGCCATGTT

AGTTCTTGGCGATACTAACTCCTGTATTTCAGCAATACCAGCAAAGCGTCGAAGAATTC

CGATTTTCCATATGGAGGCTGGGAATCGTTGTTTTGATCAACGCGTACCGGAAGAAACT

AACAGAAAAATAGTTGACCACACCGCTGATATCAATATGACATATAGTGATATCGCGCG

TGAATATCTTTTGGCTGAAGGTGTACCAGCCGATAGGATTATTAAAACCGGTAGCCCAA

TGTTTGAAGTACTCACTCATTATATGTCGCAGATTGATGGTTCCGATGTACTTTCTCGCC

TGAATTTAACACCTGGGAATTTCTTTGTGGTAAGTGCCCACAGAGAAGAAAATGTTGAT

ACCCCTAAACAGCTTGCGAAACTGGCAAATATACTTAATACCGTGGCTGAAAAATATGA

TATCCCGGTAGTTGTTTCTACTCATCCGCGCACTCGTAACCGCATCAACGAAACGGTA

TTCAATTTCATAAAAATATCTTGCTACTTAAGCCATTAGGATTTCACGATTACAACCATC

TGCAAAAAAATGCACGTGCTGTTTTATCGGATAGCGGGACTATTACAGAGGAGTCCTCC

ATTATGAACTTCCCTGCGCTCAATATACGAGAAGCGCACGAACGCCCTGAAGGCTTCGA
```

-continued

AGAAGGGGCTGTAATGATGGTTGGTCTTGAGTCTGCCCGTGTGTTACAGGCATTAGAAA

TTATTGCAACACAGCCTCGTGGAGAAGTACGCTTACTTCGTCAGGTCAGTGACTATAGT

ATGCCAAATGTTTCAGATAAAGTTGTGCGTATTATCCATTCATATACTGACTACGTTAAA

CGGGTTGTCTGGAAGCAATACTAATGAAACTTGCATTAATCATTGATGATTATTTGCCCC

ATAGCACACGAGTTGGGGCTAAAATGTTTCATGAGTTAGGCCTGGAATTGCTGAGCAGA

GGCCATGATGTAACTGTAATTACGCCTGACAACACATTACAGGCAATCTATTCTGTTAG

CATGACTGATGGTATAAAGGTTTGGCGTTTCAAAAGTGGACCTTTAAAGGATATAGGTA

AGGCTAAACGTGCCATAAATGAAACTCTTTTATCTTTTCGTGCATGGCACGCATTAAAG

CATCTCATCCAACATGATACATTTGATGGTATCGTTTATTATTCCCCCTCTATTTTTGGG

GAGGCTTGGTTAAAAAAATTAAAGAGCGATGCCAGTGCCCAAGCTATCTGGTCCTAAG

GGATATGTTCCCACAGTGGGTCATTGATGCTGGTATGATAAAAGCCGGCTCGCCAATTG

AAAAATATTTCAGGTATTTTGAAAAAAAATCATATCAACAGGCTGACTGGATTGGGTTA

ATGTCTGATAAGAATCTTGAGATATTTCGTCAGGCCAATAAAGGTTATCCGTGTGAAGT

TTTACGTAATTGGGCCTCAATGACTCCTGTGTCTGCCGGCGATGATTATCATTCACTTCG

TCAAAAATACGCTCTAAAAGATAAAATCATTTTTTTCTATGGCGGTAATATTGGGCATG

CTCAGGATATGGCAAACTTAATGCGCCTTGCGCGTAATATGATGCGTCATCATGATGCT

CATTTCCTGTTTATAGGGCAGGGTGATGAAGTTGACCTGATTAAATCTCTTTCTGCAGAA

TGGAATTTAACTAATTTCACTCATCTACCTTCAGTGAACCAGGAAGAGTTTAAATTAATT

TTATCTGAAGTTGATGTTGGCCTGTTCTCCCTTTCGTCTCGCCATTCTTCACATAATTTCC

CCGGAAAATTACTAGGGTATATGGTTCAATCAATCCCGATCCTTGGGAGTGTGAATGGC

GGTAATGATCTAATGGATGTAATTAATAAGCACAGGGCTGGGTTCATTCATGTTAATGG

TGAAGATGATAAACTGTTTGAATCTGCACAATTGCTTCTTAGTGATTCAGTTTTAAGAAA

ACAGTTAGGTCAGAACGCCAATGTGTTGTTAAAGTCTCAATTTTCGGTTGAATCGGCGG

CACATACTATCGAAGTCCGACTGGAGGCAGGAGAATGCGTTTAGTTGATGACAATATTA

TGGATGAACTTTTTCGCACTGCAGCAAATTCTGAACGTTTGCGCGCTCATTATTTATTGC

ACGCATCTCATCAGGAGAAGGTTCAACGTTTACTTATTGCATTTGTACGCGACAGCTAT

GTTGAACCCCATTGGCATGAGTTACCGCATCAGTGGGAAATGTTTGTCGTCATGCAAGG

GCAATTAGAAGTTTGTTTGTATGAGCAAAATGGTGAGCTCCAAAAAAGTTTGTTGTTG

GAGACGGTACGGGAATAAGTGTCGTGGAATTTTCCCCAGGAGATATACATAGTGTCAA

ATGCCTGTCACCAAAAGCCCTTATGTTAGAGATAAAGGAGGGGCCATTTGACCCACTGA

AAGCTAAGGCTTTTTCTAAGTGGTTATAGGGCGATACACCACCGTTTATTCTTCTATCTT

ATTCTATACATGCTGGGTTACCATCTTAGCTTCTTCAAGCCGCGTAACCCCGCGTGACCA

CCCCTGACAGGAGTAAACAATGTCA

AF078736.1 Escherichia coli O111 O antigen
gene cluster, partial sequence

SEQ ID NO: 6

GATCTGATGGCCGTAGGGCGCTACGTGCTTTCTGCTGATATCTGGGCTGAGTTGGAAAA

AACTGCTCCAGGTGCCTGGGGACGTATTCAACTGACTGATGCTATTGCAGAGTTGGCTA

AAAAACAGTCTGTTGATGCCATGCTGATGACCGGCGACAGCTACGACTGCGGTAAGAA

GATGGGCTATATGCAGGCATTCGTTAAGTATGGGCTGCGCAACCTTAAAGAAGGGGCG

AAGTTCCGTAAGAGCATCAAGAAGCTACTGAGTGAGTAGAGATTTACACGTCTTTGTGA

CGATAAGCCAGAAAAAATAGCGGCAGTTAACATCCAGGCTTCTATGCTTTAAGCAATGG

-continued
```
AATGTTACTGCCGTTTTTTATGAAAAATGACCAATAATAACAAGTTAACCTACCAAGTT
TAATCTGCTTTTTGTTGGATTTTTTCTTGTTTCTGGTCGCATTTGGTAAGACAATTAGCGT
GAGTTTTAGAGAGTTTTGCGGGATCTCGCGGAACTGCTCACATCTTTGGCATTTAGTTAG
TGCACTGGTAGCTGTTAAGCCAGGGGCGGTAGCTTGCCTAATTAATTTTTAACGTATAC
ATTTATTCTTGCCGCTTATAGCAAATAAAGTCAATCGGATTAAACTTCTTTTCCATTAGG
TAAAAGAGTGTTTGTAGTCGCTCAGGGAAATTGGTTTTGGTAGTAGTACTTTTCAAATTA
TCCATTTTCCGATTTAGATGGCAGTTGATGTTACTATGCTGCATACATATCAATGTATAT
TATTTACTTTTAGAATGTGATATGAAAAAAATAGTGATCATAGGCAATGTAGCGTCAAT
GATGTTAAGGTTCAGGAAAGAATTAATCATGAATTTAGTGAGGCAAGGTGATAATGTAT
ATTGTCTAGCAAATGATTTTTCCACTGAAGATCTTAAAGTACTTTCGTCATGGGCGTTA
AGGGGGTTAAATTCTCTCTTAACTCAAAGGGTATTAATCCTTTTAAGGATATAATTGCTG
TTTATGAACTAAAAAAAATTCTTAAGGATATTTCCCCAGATATTGTATTTTCATATTTTG
TAAAGCCAGTAATATTTGGAACTATTGCTTCAAAGTTGTCAAAAGTGCCAAGGATTGTT
GGAATGATTGAAGGTCTAGGTAATGCCTTCACTTATTATAAGGGAAAGCAGACCACAA
AAACTAAAATGATAAAGTGGATACAAATTCTTTTATATAAGTTAGCATTACCGATGCTT
GATGATTTGATTCTATTAAATCATGATGATAAAAAAGATTTAATCGATCAGTATAATAT
TAAAGCTAAGGTAACAGTGTTAGGTGGGATTGGATTGGATCTTAATGAGTTTTCATATA
AAGAGCCACCGAAAGAGAAAATTACCTTTATTTTTATAGCAAGGTTATTAAGAGAGAA
AGGGATATTTGAGTTTATTGAAGCCGCAAAGTTCGTTAAGACAACTTATCCAAGTTCTG
AATTTGTAATTTTAGGAGGTTTTGAGAGTAATAATCCTTTCTCATTACAAAAAAATGAA
ATTGAATCGCTAAGAAAAGAACATGATCTTATTTATCCTGGTCATGTGGAAAATGTTCA
AGATTGGTTAGAGAAAAGTTCTGTTTTTGTTTTACCTACATCATATCGAGAAGGCGTACC
AAGGGTGATCCAAGAAGCTATGGCTATTGGTAGACCTGTAATAACAACTAATGTACCTG
GGTGTAGGGATATAATAAATGATGGGGTCAATGGCTTTTTGATACCTCCATTTGAAATT
AATTTACTGGCAGAAAAAATGAAATATTTTATTGAGAATAAAGATAAAGTACTCGAAAT
GGGGCTTGCTGGAAGGAAGTTTGCAGAAAAAAACTTTGATGCTTTTGAAAAAAATAAT
AGACTAGCATCAATAATAAAATCAAATAATGATTTTTGACTTGAGCAGAAATTATTTAT
ATTTCAATCTGAAAAATAAAGGCTGTTATTATGAATAAAGTGGCATTAATTACTGGTAT
CACTGGGCAAGATGGCTCCTATTTGGCAGAATTATTGTTAGAAAAAGGTTATGAAGTTC
ATGGTATTAAACGCCGTGCATCTTCATTTAATACTGAGCGAGTGGATCACATCTATCAG
GATTCACATTTAGCTAATCCTAAACTTTTTCTACACTATGGCGATTTGACAGATACTTCC
AATCTGACCCGTATTTTAAAAGAAGTTCAACCAGATGAAGTTTACAATTTGGGGCGAT
GAGCCATGTAGCGGTATCATTTGAGTCACCAGAATACACTGCTGATGTTGATGCGATAG
GAACATTGCGTCTTCTTGAAGCTATCAGGATATTGGGGCTGGAAAAAAAGACAAAATTT
TATCAGGCTTCAACTTCAGAGCTTTATGGTTTGGTTCAAGAAATTCCACAAAAAGAGAC
TACGCCATTTTATCCACGTTCGCCTTATGCTGTTGCAAAATTATATGCCTATTGGATCAC
TGTTAATTATCGTGAGTCTTATGGTATGTTTGCCTGCAATGGTATTCTCTTTAACCACGA
ATCACCTCGCCGTGGCGAGACCTTTGTTACTCGTAAAATAACACGCGGGATAGCAAATA
TTGCTCAAGGTCTTGATAAATGCTTATACTTGGGAAATATGGATTCTCTGCGTGATTGGG
GACATGCTAAGGATTATGTCAAAATGCAATGGATGATGCTGCAGCAAGAAACTCCAGA
AGATTTTGTAATTGCTACAGGAATTCAATATTCTGTCCGTGAGTTTGTCACAATGGCGGC
```

-continued

```
AGAGCAAGTAGGCATAGAGTTAGCATTTGAAGGTGAGGGAGTAAATGAAAAAGGTGTT
GTTGTTTCGGTCAATGGCACTGATGCTAAAGCTGTAAACCCGGGCGATGTAATTATATC
TGTAGATCCAAGGTATTTTAGGCCTGCAGAAGTTGAAACCTTGCTTGGCGATCCTACTA
ATGCGCATAAAAAATTAGGATGGAGCCCTGAAATTACATTGCGTGAAATGGTAAAAGA
AATGGTTTCCAGCGATTTAGCAATAGCGAAAAAGAACGTCTTGCTGAAAGCTAATAACA
TTGCCACTAATATTCCGCAAGAATAAAAAAGATAATACATTAAATAATTAAAAATGGTG
CTAGATTTATTAGTACCATTATTTTTTTTGGGTGACTAATGTTTATTACATCAGATAAAT
TTAGAGAAATTATCAAGTTAGTTCCATTAGTATCAATTGATCTGCTAATTGAAAACGAG
AATGGTGAATATTTATTTGGTCTTAGGAATAATCGACCGGCCAAAAATTATTTTTTTGTT
CCAGGTGGTAGGATTCGCAAAAATGAATCTATTAAAAATGCTTTTAAAAGAATATCATC
TATGGAATTAGGTAAAGAGTATGGTATTTCAGGAAGTGTTTTTAATGGTGTATGGGAAC
ATTTCTATGATGATGGTTTTTTTTCTGAAGGCGAGGCAACACATTATATAGTGCTTTGTT
ACACACTGAAAGTTCTTAAAAGTGAATTGAATCTCCCAGATGATCAACATCGTGAATAC
CTTTGGCTAACTAAACACCAAATAAATGCTAAACAAGATGTTCATAACTATTCAAAAAA
TTATTTTTTGTAATTTTTATTAAAAATTAATATGCGAGAGAATTGTATGTCTCAATGTCTT
TACCCTGTAATTATTGCCGGAGGAACCGGAAGCCGTCTATGGCCGTTGTCTCGAGTATT
ATACCCTAAACAATTTTTAAATTTAGTTGGGGATTCTACAATGTTGCAAACAACAATTA
CGCGTTTGGATGGCATCGAATGCGAAAATCCAATTGTTATCTGCAATGAAGATCACCGA
TTTATTGTAGCAGAGCAATTACGACAGATTGGTAAGCTAACCAAGAATATTATACTTGA
GCCGAAAGGCCGTAATACTGCACCTGCCATAGCTTTAGCTGCTTTTATCGCTCAGAAGA
ATAATCCTAATGACGACCCTTTATTATTAGTACTTGCGGCAGACCACTCTATAAATAATG
AAAAAGCATTTCGAGAGTCAATAATAAAAGCTATGCCGTATGCAACTTCTGGGAAGTTA
GTAACATTTGGAATTATTCCGGACACGGCAAATACTGGTTATGGATATATTAAGAGAAG
TTCTTCAGCTGATCCTAATAAAGAATTCCCAGCATATAATGTTGCGGAGTTTGTAGAAA
AACCAGATGTTAAAACAGCACAGGAATATATTTCGAGTGGGAATTATTACTGGAATAGC
GGAATGTTTTTATTTCGCGCCAGTAAATATCTTGATGAACTACGGAAATTTAGACCAGA
TATTTATCATAGCTGTGAATGTGCAACCGCTACAGCAAATATAGATATGGACTTTGTCC
GAATTAACGAGGCTGAGTTTATTAATTGTCCTGAAGAGTCTATCGATTATGCTGTGATG
GAAAAAACAAAAGACGCTGTAGTTCTTCCGATAGATATTGGCTGGAATGACGTGGGTTC
TTGGTCATCACTTTGGGATATAAGCCAAAAGGATTGCCATGGTAATGTGTGCCATGGGG
ATGTGCTCAATCATGATGGAGAAAATAGTTTTATTTACTCTGAGTCAAGTCTGGTTGCG
ACAGTCGGAGTAAGTAATTTAGTAATTGTCCAAACCAAGGATGCTGTACTGGTTGCGGA
CCGTGATAAAGTCCAAAATGTTAAAAACATAGTTGACGATCTAAAAAAGAGAAAACGT
GCTGAATACTACATGCATCGTGCAGTTTTTCGCCCTTGGGGTAAATTCGATGCAATAGA
CCAAGGCGATAGATATAGAGTAAAAAAAATAATAGTTAAACCAGGAGAAGGGTTAGAT
TTAAGGATGCATCATCATAGGGCAGAGCATTGGATTGTTGTATCCGGTACTGCTAAAGT
TTCACTAGGTAGTGAAGTTAAACTATTAGTTTCTAATGAGTCTATATATATCCCTCAGGG
AGCAAAATATAGTCTTGAGAATCCAGGCGTAATACCTTTGCATCTAATTGAAGTAAGTT
CTGGTGATTACCTTGAATCAGATGATATAGTGCGTTTTACTGACAGATATAACAGTAAA
CAATTCCTAAAGCGAGATTGATAAATATGAATAAAATAACTTGCTTCAAAGCATATGAT
```

-continued

```
ATACGTGGGCGTCTTGGTGCTGAATTGAATGATGAAATAGCATATAGAATTGGTCGCGC
TTATGGTGAGTTTTTTAAACCTCAAACTGTAGTTGTGGGAGGAGATGCTCGCTTAACAA
GTGAGAGTTTAAAGAAATCACTCTCAAATGGGCTATGTGATGCAGGCGTAAATGTCTTA
GATCTTGGAATGTGTGGTACTGAAGAGATATATTTTTCCACTTGGTATTTAGGAATTGAT
GGTGGAATCGAGGTAACTGCAAGCCATAATCCAATTGATTATAATGGAATGAAATTAGT
AACCAAAGGTGCTCGACCAATCAGCAGTGACACAGGTCTCAAAGATATACAACAATTA
GTAGAGAGTAATAATTTTGAAGAGCTCAACCTAGAAAAAAAAGGGAATATTACCAAAT
ATTCCACCCGAGATGCCTACATAAATCATTTGATGGGCTATGCTAATCTGCAAAAAATA
AAAAAAATCAAATAGTTGTGAATTCTGGGAATGGTGCAGCTGGTCCTGTTATTGATGC
TATTGAGGAATGCTTTTTACGGAACAATATTCCGATTCAGTTTGTAAAAATAAATAATA
CACCCGATGGTAATTTTCCACATGGTATCCCTAATCCATTACTACCTGAGTGCAGAGAA
GATACCAGCAGTGCGGTTATAAGACATAGTGCTGATTTTGGTATTGCATTTGATGGTGA
TTTTGATAGGTGTTTTTTCTTTGATGAAAATGGACAATTTATTGAAGGATACTACATTGT
TGGTTTATTAGCGGAAGTTTTTTTAGGGAAATATCCAAACGCAAAAATCATTCATGATC
CTCGCCTTATATGGAATACTATTGATATCGTAGAAAGTCATGGTGGTATACCTATAATG
ACTAAAACCGGTCATGCTTACATTAAGCAAAGAATGCGTGAAGAGGATGCCGTATATG
GCGGCGAAATGAGTGCGCATCATTATTTTAAAGATTTTGCATACTGCGATAGTGGAATG
ATTCCTTGGATTTTAATTTGTGAACTTTTGAGTCTGACAAATAAAAAATTAGGTGAACTG
GTTTGTGGTTGTATAAACGACTGGCCGGCAAGTGGAGAAATAAACTGTACACTAGACA
ATCCGCAAAATGAAATAGATAAATTATTTAATCGTTACAAAGATAGTGCCTTAGCTGTT
GATTACACTGATGGATTAACTATGGAGTTCTCTGATTGGCGTTTTAATGTTAGATGCTCA
AATACAGAACCTGTAGTACGATTGAATGTAGAATCTAGGAATAATGCTATTCTTATGCA
GGAAAAAACAGAAGAAATTCTGAATTTTATATCAAAATAAATTTGCACCTGAGTTCATA
ATGGGAACAAGAAATATATGAAAGTACTTCTGACTGGCTCAACTGGCATGGTTGGTAAG
AATATATTAGAGCATGATAGTGCAAGTAAATATAATATACTTACTCCAACCAGCTCTGA
TTTGAATTTATTAGATAAAAATGAAATAGAAAAATTCATGCTTATCAACATGCCAGACT
GTATTATACATGCAGCGGGATTAGTTGGAGGCATTCATGCAAATATAAGCAGGCCGTTT
GATTTTCTGGAAAAAAATTTGCAGATGGGTTTAAATTTAGTTTCCGTCGCAAAAAAACT
AGGTATCAAGAAAGTGCTTAACTTGGGTAGTTCATGCATGTACCCCAAAAACTTTGAAG
AGGCTATTCCTGAGAAAGCTCTGTTAACTGGTGAGCTAGAAGAAACTAATGAGGGATAT
GCTATTGCGAAAATTGCTGTAGCAAAAGCATGCGAATATATATCAAGAGAAAACTCTA
ATTATTTTTATAAAACAATTATCCCATGTAATTTATATGGGAAATATGATAAATTTGATG
ATAACTCGTCACATATGATTCCGGCAGTTATAAAAAAAATCCATCATGCGAAAATTAAT
AATGTCCCAGAGATCGAAATTTGGGGGGATGGTAATTCGCGCCGTGAGTTTATGTATGC
AGAAGATTTAGCTGATCTTATTTTTTATGTTATTCCTAAAATAGAATTCATGCCTAATAT
GGTAAATGCTGGTTTAGGTTACGATTATTCAATTAATGACTATTATAAGATAATTGCAG
AAGAAATTGGTTATACTGGGAGTTTTTCTCATGATTTAACAAAACCAACAGGAATGAAA
CGGAAGCTAGTAGATATTTCATTGCTTAATAAAATTGGTTGGTCAAGTCACTTTGAACTC
AGAGATGGCATCAGAAAGACCTATAATTATTACTTGGAGAATCAAAATAAATGATTAC
ATACCCACTTGCTAGTAATACTTGGGATGAATATGAGTATGCAGCAATACAGTCAGTAA
TTGACTCAAAAATGTTTTACCATGGGTAAAAAGGTTGAGTTATATGAGAAAAATTTTGCT
```

-continued

```
GATTTGTTTGGTAGCAAATATGCCGTAATGGTTAGCTCTGGTTCTACAGCTAATCTGTTA
ATGATTGCTGCCCTTTTCTTCACTAATAAACCAAAACTTAAAAGAGGTGATGAAATAAT
AGTACCTGCAGTGTCATGGTCTACGACATATTACCCTCTGCAACAGTATGGCTTAAAGG
TGAAGTTTGTCGATATCAATAAAGAAACTTTAAATATTGATATCGATAGTTTGAAAAAT
GCTATTTCAGATAAAACAAAAGCAATATTGACAGTAAATTTATTAGGTAATCCTAATGA
TTTTGCAAAAATAAATGAGATAATAAATAATAGGGATATTATCTTACTAGAAGATAACT
GTGAGTCGATGGGCGCGGTCTTTCAAAATAAGCAGGCAGGCACATTCGGAGTTATGGGT
ACCTTTAGTTCTTTTTACTCTCATCATATAGCTACAATGGAAGGGGCTGCGTAGTTACT
GATGATGAAGAGCTGTATCATGTATTGTTGTGCCTTCGAGCTCATGGTTGGACAAGAAA
TTTACCAAAAGAGAATATGGTTACAGGCACTAAGAGTGATGATATTTTCGAAGAGTCGT
TTAAGTTTGTTTTACCAGGATACAATGTTCGCCCACTTGAAATGAGTGGTGCTATTGGA
TAGAGCAACTTAAAAAGTTACCAGGTTTTATATCCACCAGACGTTCCAATGCACAATAT
TTTGTAGATAAATTTAAAGATCATCCATTCCTTGATATACAAAAAGAAGTTGGTGAAAG
TAGCTGGTTTGGTTTTTCCTTCGTTATAAAGGAGGGAGCTGCTATTGAGAGGAAGAGTT
TAGTAAATAATCTGATCTCAGCAGGCATTGAATGCCGACCAATTGTTACTGGGAATTTT
CTCAAAAATGAACGTGTTTTGAGTTATTTTGATTACTCTGTACATGATACGGTAGCAAAT
GCCGAATATATAGATAAGAATGGTTTTTTTGTCGGAAACCACCAGATACCTTTGTTTAAT
GAAATAGATTATCTACGAAAAGTATTAAAATAACTAACGAGGCACTCTATTTCGAATAG
AGTGCCTTTAAGATGGTATTAACAGTGAAAAAAATTTTAGCGTTTGGCTATTCTAAAGT
ACTACCACCGGTTATTGAACAGTTTGTCAATCCAATTTGCATCTTCATTATCACACCACT
AATACTCAACCACCTGGGTAAGCAAAGCTATGGTAATTGGATTTTATTAATTACTATTGT
ATCTTTTTCTCAGTTAATATGTGGAGGATGTTCCGCATGGATTGCAAAAATCATTGCAGA
ACAGAGAATTCTTAGTGATTTATCAAAAAAAATGCTTTACGTCAAATTTCCTATAATTT
TTCAATTGTTATTATCGCATTTGCGGTATTGATTTCTTTTCTTATATTAAGTATTTGTTTCT
TCGATGTTGCGAGGAATAATTCTTCATTCTTATTCGCGATTATTATTTGTGGTTTTTTCA
GGAAGTTGATAATTTATTTAGTGGTGCGCTAAAAGGTTTTGAAAAATTTAATGTATCAT
GTTTTTTTGAAGTAATTACAAGAGTGCTCTGGGCTTCTATAGTAATATATGGCATTTACG
GAAATGCACTCTTATATTTTACATGTTTAGCCTTTACCATTAAAGGTATGCTAAAATATA
TTCTTGTATGTCTGAATATTACCGGTTGTTTCATCAATCCTAATTTTAATAGAGTTGGGA
TTGTTAATTTGTTAAATGAGTCAAAATGGATGTTTCTTCAATTAACTGGTGGCGTCTCAC
TTAGTTTGTTTGATAGGCTCGTAATACCATTGATTTTATCTGTCAGTAAACTGGCTTCTT
ATGTCCCTTGCCTTCAACTAGCTCAATTGATGTTCACTCTTTCTGCGTCTGCAAATCAAA
TATTACTACCAATGTTTGCTAGAATGAAAGCATCTAACACATTTCCCTCTAATTGTTTTT
TTAAAATTCTGCTTGTATCACTAATTTCTGTTTTGCCTTGTCTTGCGTTATTCTTTTTGGT
CGTGATATATTATCAATATGGATAAACCCTACATTTGCAACTGAAAATTATAAATTAAT
GCAAATTTTAGCTATAAGTTACATTTTATTGTCAATGATGACATCTTTTCATTTCTTGTTA
TTAGGAATTGGTAAATCTAAGCTTGTTGCAAATTTAAATCTGGTTGCAGGGCTCGCACTT
GCTGCTTCAACGTTAATCGCAGCTCATTATGGCCTTTATGCAATATCTATGGTAAAAATA
ATATATCCGGCTTTTCAATTTATTACCTTTATGTAGCTTTTGTCTATTTTAATAGAGCGA
AAAATGTCTATTGATTTACTTTTTTCAATTACTGAAATCGCAATTGTTTTTTCTTGCACTA
```

-continued

```
TTTACATATTTACTCAATGTTTGTTAATGCGGAGGATCTATTTAGATAAAAGTATTTTAA

TTCTTTTATGCTTGCTCTTTTTTTAGTAATCATTCAACTTCCTGAGCTTAATGTAAACGG

TTTGGTCGATTCTTTAAAGTTATCACTGCCTTTATTGATGGTCTTTATCGCTTTTCAAAA

CCGAAATTATGCTTGTGGGTTATTATTGCATTGTTGTTTTTGAACTCTGCATTTAATTTTT

TATATTTAAAGACATTCGATAAGTTTAGCTCATTTCCTTTTACTTTTTTTATATTGCTGTT

TTACTTGTTTAGATTGGGAATTGGTAATTTACCGGTTTATAAAAATAAAAAATTTTACGC

GTTGATTTTCTCTTTATATTAATAGACATAATGCAGTCATTGTTAATAAATTATAGGGG

GCAGATTTTATATTCCGTAATTTGCATCCTGATACTTGTGTTTAAAGTTAATTTAAGAAA

AAAGATTCCATACTTTTTTTTAATGCTGCCAGTTTTATATGTAATTATTATGGCTTATATT

GGTTTTAATTATTTCAATAAAGGCGTAACTTTTTTTGAACCTACAGCAAGTAATATTGAA

CGTACGGGGATGATATATTATTTGGTTTCACAGCTTGGTGATTATATATTCCATGGTATG

GGGACATTAAATTTCTTAAATAACGGCGGACAATATAAGACGTTATATGGACTTCCATC

ATTAATTCCTAATGACCCTCATGATTTTTATTACGGTTCTTTATAAGTATTGGTGTGATA

GGAGCATTGGTTTATCATTCTATATTTTTGTTTTTTTAGGAGAATATCTTTCTTATTAT

ATGAGAGAAATGCTCCTTTCATTGTTGTAAGTTGTTTGTTACTGTTACAAGTTGTGTTAA

TTTATACATTAAACCCTTTTGATGCTTTTAATCGATTGATTTGCGGGCTTACAGTTGGAG

TTGTTTATGGATTTGCAAAAATTAGATAAGTATACCTGTAATGGAAATTTAGACGCTCC

ACTTGTTTCAATAATCATTGCAACTTATAATTCTGAACTTGATATAGCTAAGTGTTTGCA

ATCGGTAACTAATCAATCTTATAAGAATATTGAAATCATAATAATGGATGGAGGATCTT

CTGATAAAACGCTTGATATTGCAAAATCGTTTAAAGACGACCGAATAAAAATAGTTTCA

GAGAAAGATCGTGGAATTTATGATGCCTGGAATAAAGCAGTTGATTTATCCATTGGTGA

TTGGGTAGCATTTATTGGTTCAGATGATGTTTACTATCATACAGATGCAATTGCTTCATT

GATGAAGGGGTTATGGTATCAATGGCGCCCCTGTGGTTTATGGGAGGACAGCGCACG

AAGGTCCCGATAGGAACATATCTGGATTTTCAGGCAGTGAATGGTACAACCTAACAGG

ATTTAAGTTTAATTATTACAAATGTAATTTACCATTGCCCATTATGAGCGCAATATATTC

TCGTGATTTCTTCAGAAACGAACGTTTTGATATTAAATTAAAAATTGTTGCTGACGCTGA

TTGGTTTCTGAGATGTTTCATCAAATGGAGTAAAGAGAAGTCACCTTATTTTATTAATGA

CACGACCCCTATTGTTAGAATGGGATATGGTGGGGTTTCGACTGATATTTCTTCTCAAGT

TAAAACTACGCTAGAAAGTTTCATTGTACGCAAAAGAATAATATATCCTGTTTAAACA

TACAGCTGATTCTTAGATATGCTAAAATTCTGGTGATGGTAGCGATCAAAAATATTTTTG

GCAATAATGTTTATAAATTAATGCATAACGGGTATCATTCCCTAAAGAAAATCAAGAAT

AAAATATGAAGATTGTTTATATAATAACCGGGCTTACTTGTGGTGGAGCCGAACACCTT

ATGACGCAGTTAGCAGACCAAATGTTTATACGCGGGCATGATGTTAATATTATTTGTCT

AACTGGTATATCTGAGGTAAAGCCAACACAAAATATTAATATTCATTATGTTAATATGG

ATAAAAATTTTAGAAGCTTTTTTAGAGCTTTATTTCAAGTAAAAAAAATAATTGTCGCCT

TAAAGCCAGATATAATACATAGTCATATGTTTCATGCTAATATTTTTAGTCGTTTTATTA

GGATGCTGATTCCAGCGGTGCCCCTGATATGTACCGCACACAACAAAAATGAAGGTGG

CAATGCAAGGATGTTTTGTTATCGACTGAGTGATTTTTTAGCTTCTATTACTACAAATGT

AAGTAAAGAGGCTGTTCAAGAGTTTATAGCAAGAAAGGCTACACCTAAAAATAAAATA

GTAGAGATTCCGAATTTTATTAATACAAATAAATTTGATTTTGATATTAATGTCAGAAA

GAAAACGCGAGATGCTTTTAATTTGAAAGACAGTACAGCAGTACTGCTCGCAGTAGGA
```

-continued

```
AGACTTGTTGAAGCAAAAGACTATCCGAACTTATTAAATGCAATAAATCATTTGATTCT

TTCAAAAACATCAAATTGTAATGATTTTATTTTGCTTATTGCTGGCGATGGCGCATTAAG

AAATAAATTATTGGATTTGGTTTGTCAATTGAATCTTGTGGATAAAGTTTTCTTCTTGGG

GCAAAGAAGTGATATTAAAGAATTAATGTGTGCTGCAGATCTTTTTGTTTTGAGTTCTGA

GTGGGAAGGTTTTGGTCTCGTTGTTGCAGAAGCTATGGCGTGTGAACGTCCCGTTGTTG

CTACCGATTCTGGTGGAGTTAAAGAAGTCGTTGGACCTCATAATGATGTTATCCCTGTC

AGTAATCATATTCTGTTGGCAGAGAAAATCGCTGAGACACTTAAAATAGATGATAACGC

AAGAAAAATAATAGGTATGAAAAATAGAGAATATATTGTTTCCAATTTTTCAATTAAAA

CGATAGTGAGTGAGTGGGAGCGCTTATATTTTAAATATTCCAAGCGTAATAATATAATT

GATTGAAAATATAAGTTTGTACTCTGGATGCAATAGTTTCTCTATGCTGTTTTTTTACTG

GCTCCGTATTTTTACTTATAGCTGGATTTTGTTATATATCAGTATTAATCTGTCTCAACTT

CATCTAGACTACATTCAAGCCGCGCATGCGTCGCGCGGTGACTACACCTGACAGGAGTA

TGTAATGTCCAAGCAACAGATCGGCGTCGTCGGTATGGCAGTGATGGGCGCAACCTG

GCGCTCAACATCGAAAGCCGCGGTTATACCGTCTCCATCTTCAACCGCTCCCGCGAGAA

AACTGAAGAAGTTGTTGCCGAGAACCCGGATAAGAAACTGGTTCCTTATTACACGGTGA

AAGAGTTCGTCGAGTCTCTTGAAACCCCACGTCGTATCCTGTTAATGGTAAAAGCAGGG

GCGGGAACTGATGCTGCTATCGATTCCCTGAAGCCGTATCTGGATAAAGGCGACATCAT

TATTGATGGTGGCAACACCTTCTTCCAGGACACTATCCGTCGTAACCGTGAACTGTCCG

CGGAAGGCTTTAACTTCATCGGTACCGGCGTGTCCGGCGGTGAAGAGGGCGCCCTGAA

AGGCCCATCTATCATGCCAGGTGGCCAGAAAGAAGCGTATGAGCTGGTTGCGCCTATCC

TGACCAAGATTGCTGCGGTTGCTGAAGATGGCGAACCATGTATAACTTACATCGGTGCT

GACGGTGCGGGTCACTACGTGAAGATGGTGCACAACGGTATCGAATATGGCGATATGC

AGCTGATTGCTGAAGCCTATTCTCTGCTTAAAGGCGGCCTTAATCTGTCTAACGAAGAG

CTGGCAACCACTTTTACCGAGTGGAATGAAGGCGAGCTAAGTAGCTACCTGATTGACAT

CACCAAAGACATCTTCACCAAAAAAGATGAAGAGGGTAAATACCTGGTTGATGTGATC

CTGGACGAAGCTGCGAACAAAGGCACCGGTAAATGGACCAGCCAGAGCTCTCTGGATC

TGGGTGAACCGCTGTCGCTGATCACCGAATCCGTATTCGCTCGCTACATCTCTTCTCTGA

AAGACCAGCGCATTGCGGCATCTAAAGTGCTGTCTGGTCCGCAGGCTAAACTGGCTGGT

GATAAAGCAGAGTTCGTTGAGAAAGTCCGTCGCGCGCTGTACCTGGGTAAAATCGTCTC

TTATGCCCAAGGCTTCTCTCAACTGCGTGCCGCGTCTGACGAATACAACTGGGATCTGA

ACTACGGCGAAATCGCGAAGATCTTCCGCGCGGGCTGCATCATTCGTGCGCAGTTCCTG

CAGAAAATTACTGACGCGTATGCTGAAAACAAAGGCATTGCTAACCTGTTGCTGGCTCC

GTACTTCAAAAATATCGCTGATGAATATCAGCAAGCGCTGCGTGATGTAGTGGCTTATG

CTGTGCAGAACGGTATTCCGGTACCGACCTTCTCTGCAGCGGTAGCCTACTACGACAGC

TACCGTTCTGCGGTACTGCCGGCTAATCTGATTCAGGCACAGCGTGATTACTTCGGTGC

GCACACGTATAAACGCACTGATAAAGAAGGTGTGTTCCACACCG
```

SEQ ID NO: 7: PRIMER FOR O103-wbtD+E-850F (forward)
GATGAAACAAACGGTAAAT

SEQ ID NO: 8: PRIMER FOR O103-wbtD+E-995R (reverse)
TTTCATATTTAGCTAACAAGTTT

SEQ ID NO: 9: PRIMER FOR O121-vioA-257F (forward)
CAACTGCACACTCCTTGGTC

-continued

SEQ ID NO: 10 PRIMER FOR O121-vioA-354R (reverse)
CGCCTCTTCAATTCTTCTCG

SEQ ID NO: 11 O26-Vir-Probe
CAGATATTACTGAAATACG-

SEQ ID NO: 12 O26 A Vir Probe
CA GAT ATT GCTGAA ATA CG-

SEQ ID NO: 13: O111 A Vir Probe
TG GTT ACA GGCACT AAG AGT-

SEQ ID NO: 14: O111 Vir Probe
TG GTT ACA GGT ACT AAG AGT-3'-

SEQ ID NO: 15: O103 A Vir Probe
AT TAA CCT GCA TAT TAA A-3'-

SEQ ID NO: 16: O103 Vir Probe
AT TAA CCT GTATAT TAA A-

SEQ ID NO: 17: O121 Vir Probe
CG ATA TTG ATC CCA AAA CC-

SEQ ID NO: 18 O121 Vir Probe
CG ATA TTG ATT CCA AAA CC-

SEQ ID NO: 19: 16S RNA-F
CCT CTT GCC ATC GGA TGT G

SEQ ID NO: 20: 16S RNA-R
GGC TGG TCA TCC TCT CAG ACC

SEQ ID NO: 21: 16S rRNA Probe
GTG GGG TAA CGG CTC ACC TAG GCG AC-

REFERENCES

1. Boer, E. D., & Heuvelink, A. E. (2000). Methods for the detection and isolation of Shiga toxin-producing *Escherichia coli*. Journal of Applied Microbiology, 88 (S1), 133S-143S. doi.org/10.1111/j.1365-2672.2000.tb05341.x
2. Etcheverría, A. I., & Padola, N. L. (2013). Shiga toxin-producing *Escherichia coli*. Virulence, 4 (5), 366-372. doi.org/10.4161/viru.24642
3. Fratamico, P. M., Bagi, L. K., Cray, W. C., Narang, N., Yan, X., Medina, M., & Liu, Y. (2011). Detection by Multiplex Real-Time Polymerase Chain Reaction Assays and Isolation of Shiga Toxin-Producing *Escherichia coli* Serogroups O26, O45, O103, O111, O121, and O145 in Ground Beef. Foodborne Pathogens and Disease, 8 (5), 601-607. doi.org/10.1089/fpd.2010.0773
4. Jana, M., Adriana, V., & Eva, K. (2020). Evaluation of DNA Extraction Methods for Culture-Independent Real-Time PCR-Based Detection of *Listeria monocytogenes* in Cheese. Food Analytical Methods, 13 (3), 667-677. doi.org/10.1007/s12161-019-01686-2
5. Li, F., Li, B., Dang, H., Kang, Q., Yang, L., Wang, Y., Aguilar, Z. P., Lai, W., & Xu, H. (2017). Viable pathogens detection in fresh vegetables by quadruplex PCR. LWT-Food Science and Technology, 81, 306-313. doi.org/10.1016/j.lwt.2017.03.064
6. Liu, Y., Singh, P., & Mustapha, A. (2018). High-resolution melt curve PCR assay for specific detection of *E. coli* O157: H7 in beef. Food Control, 86, 275-282. doi.org/10.1016/j.foodcont.2017.11.025
7. Lusk, T. S., Strain, E., & Kase, J. A. (2013). Comparison of six commercial DNA extraction kits for detection of *Brucella neotomae* in Mexican and Central American-style cheese and other milk products. Food Microbiology, 34 (1), 100-105. doi.org/10.1016/j.fm.2012.11.007
8. Norman, K. N., Strockbine, N. A., & Bono, J. L. (2012). Association of Nucleotide Polymorphisms within the O-Antigen Gene Cluster of *Escherichia coli* O26, O45, O103, O111, O121, and O145 with Serogroups and Genetic Subtypes. Applied and Environmental Microbiology, 78 (18), 6689-6703. doi.org/10.1128/AEM.01259-12
9. Singh, P., Liu, Y., Bosilevac, J. M., & Mustapha, A. (2019). Detection of Shiga toxin-producing *Escherichia coli*, stx1, stx2 and *Salmonella* by two high resolution melt curve multiplex real-time PCR. Food Control, 96, 251-259. doi.org/10.1016/j.foodcont.2018.09.024
10. Singh, P., & Mustapha, A. (2015). Multiplex real-time PCR assays for detection of eight Shiga toxin-producing *Escherichia coli* in food samples by melting curve analysis. International Journal of Food Microbiology, 215, 101-108. doi.org/10.1016/j.ijfoodmicro.2015.08.022
11. Untergasser, A., Cutcutache, I., Koressaar, T., Ye, J., Faircloth, B. C., Remm, M., & Rozen, S. G. (2012). Primer3-new capabilities and interfaces. Nucleic Acids Research, 40 (15), e115-e115.
12. Wasilenko, J. L., Fratamico, P. M., Narang, N., Tillman, G. E., Ladely, S., Simmons, M., & Cray, W. C. (2012). Influence of Primer Sequences and DNA Extraction Method on Detection of Non-O157 Shiga Toxin-Producing *Escherichia coli* in Ground Beef by Real-Time PCR Targeting the eae, stx, and Serogroup-Specific Genes. Journal of Food Protection, 75 (11), 1939-1950. doi.org/10.4315/0362-028X.JFP-12-087

What is claimed is:

1. A method for discriminating a virulent Shiga toxin-producing *E. coli* (STEC) O26 strain DNA from an avirulent Shiga toxin-producing *E. coli* (STEC) O26 strain DNA in a biological sample, the method comprising the steps of:
   (i) enriching bacterial concentration of the biological sample to result in an enriched sample;
   (ii) isolating a DNA sample from said enriched biological sample; and
   (iii) hybridizing a target region of the DNA sample to at least one primer pair or at least one probe, wherein the at least one primer pair comprises SEQ ID NO: 1 and SEQ ID NO: 2 and the at least one primer pair discriminates between the virulent STEC O26 DNA and the avirulent STEC O26 DNA, or the at least one probe comprises SEQ ID NO: 11 or SEQ ID NO: 12 and the at least one probe discriminates between the virulent STEC O26 DNA and the avirulent STEC O26 DNA, and wherein the at least one probe comprises a locked nucleic acid (LNA) base.

2. The method of claim 1, further comprising performing a real-time PCR high resolution melt curve assay on the virulent STEC O26 DNA and/or the avirulent STEC O26 DNA to determine a melting temperature of the virulent STEC O26 DNA and a melting temperature of the avirulent STEC O26 DNA, wherein the melting temperature of the virulent STEC O26 DNA is decreased relative to the melting temperature of the avirulent STEC O26 DNA.

3. The method of claim 2, wherein said real-time PCR uses as an internal amplification control SEQ ID NO: 19, SEQ ID NO: 20 and SEQ ID NO: 21.

4. The method of claim 2, wherein the melting temperature between virulent and avirulent O26 DNA differs by 0.2-4° C.

5. The method of claim 1, wherein said biological sample comprises a food or a beverage.

6. The method of claim 5, wherein said food or beverage comprises meat, produce, or juice.

7. The method of claim 1, wherein said biological sample comprises a clinical sample.

8. The method of claim 7, wherein said clinical sample comprises stool, urine, or blood.

9. The method of claim 1, wherein the at least one probe comprises a detectable label.

10. The method of claim 1, further comprising performing a probe-based assay on the virulent STEC O26 DNA and/or the avirulent STEC O26 DNA to visualize an amplicon of the virulent STEC O26 DNA and to visualize an amplicon of the avirulent STEC O26 DNA, wherein the amplicon of the virulent STEC O26 DNA and/or the amplicon of the avirulent STEC O26 DNA are visualized according to size.

11. A kit comprising at least one primer pair comprising SEQ ID NO: 1 and SEQ ID NO: 2; and at least one probe comprising SEQ ID NO: 11, a locked nucleic acid (LNA) base, and a detectable label and/or SEQ ID NO: 12, an LNA, and a detectable label.

12. The kit of claim 11, wherein said kit further comprises additional reagents for amplification.

* * * * *

SEQUENCE LISTING

<160> NUMBER OF SEQ ID NOS: 21

<210> SEQ ID NO 1
<211> LENGTH: 20
<212> TYPE: DNA
<213> ORGANISM: Artificial sequence
<220> FEATURE:
<223> OTHER INFORMATION: Description of sequence: O26 fnl1-32F (forward primer)

<400> SEQUENCE: 1
gtggcactgg ttcttttggt                                                                20

<210> SEQ ID NO 2
<211> LENGTH: 22
<212> TYPE: DNA
<213> ORGANISM: Artificial sequence
<220> FEATURE:
<223> OTHER INFORMATION: Description of sequence: O26 fnl1-118R (reverse primer)

<400> SEQUENCE: 2
tttcatccct gctaaatatt cg                                                             22

<210> SEQ ID NO 3
<211> LENGTH: 20
<212> TYPE: DNA
<213> ORGANISM: Artificial sequence
<220> FEATURE:
<223> OTHER INFORMATION: Description of sequence: O111 wbdK-634F (forward primer)

<400> SEQUENCE: 3
cttcgagctc atggttggac                                                                20

<210> SEQ ID NO 4
<211> LENGTH: 19
<212> TYPE: DNA
<213> ORGANISM: Artificial sequence
<220> FEATURE:
<223> OTHER INFORMATION: Description of sequence: O111 wbdK-717R (reverse primer)

<400> SEQUENCE: 4
cgactcttcg aaaatatca                                                                 19

<210> SEQ ID NO 5
<211> LENGTH: 11706
<212> TYPE: DNA
<213> ORGANISM: Artificial sequence
<220> FEATURE:
<223> OTHER INFORMATION: Description of sequence: AY763106.1, O26 Escherichia coli serotype O26, H11 O-antigen operon, partial sequence

<400> SEQUENCE: 5
gcattaatac ccctattaat caacctaaga gccgcttatt tcacagcatg ctctgaagta          60
atatggaata ataaagtgaa gatacttgtt actggtggcg caggatttat tggttctgct        120
gtagttcgtc acattataaa taatacgcag gatagtgttg ttaatgtcga taaattaacg        180
tacgccggaa acctggaatc acttgctgat gtttctgatt ctgaacgcta tgttttgaa         240 catgcggata tttgcgatgc agctgcaatg gcgcggattt tgctcagca tcagccggat         300 gcagtgatgc acctggctgc tgaaagccat gttgaccgtt caattaccgg ccctgcggca        360
tttattgaaa ccaatattgt tggtacttat gtccttttgg aagccgctcg caattactgg        420

| | |
|---|---|
| tctgctcttg atagcgacaa gaaaaatagc ttccgttttc atcatatttc tactgacgaa | 480 |
| gtctatggtg atttgcctca tcctgacgaa gtaaataata cagaagaatt acccttattt | 540 |
| actgagacga cagcttacgc gccaagcagt ccttattccg catccaaagc atctagcgat | 600 |
| catttagtcc gcgcgtggaa acgtacctat ggtttaccga ccattgtgac taactgttcg | 660 |
| aataactacg gcccttatca ctttccggaa aaattgattc cgctggtaat tcttaatgct | 720 |
| ctggaaggta aggcattacc tatttatggc aaagggatc aaattcgcga ttggctatat | 780 |
| gttgaagatc atgcgcgtgc gttatatacc gttgtcaccg aaggtaaagc gggtgaaact | 840 |
| tataacattg gcggacacaa cgaaaagaaa acatcgatg ttgtgctgac tatttgtgat | 900 |
| ttgttggatg agattgtacc gaaagagcaa tcttatcgtg agcaaattac ttatgttgcc | 960 |
| gatcgtccgg gacacgatcg ccgttatgcg attgatgctg agaagattag ccgcgaattg | 1020 |
| ggctggaaac cgcaggaaac gtttgagagc gggattcgga agacagtgga atggtacctg | 1080 |
| tccaatacaa aatgggtcga aaatgtgaaa agtggtgcct atcagtcatg gattgcacag | 1140 |
| aactatgagg gccgtcagta atgaatatcc tcctttcgg caaaacaggg caggtaggtt | 1200 |
| gggaactaca gcgtgctctg gcacctctgg gtaatttgat tgctcttgat gttcactcta | 1260 |
| ctgattattg cggtgatttt agtaatcctg aaggtgtagc tgaaaccgta agaagcattc | 1320 |
| ggcctgatat tattgtcaac gcagccgctc acaccgcagt agacaaagca gaatcagaac | 1380 |
| cggagtttgc acaattactt aacgcaacaa gtgtcgaagc gattgcgaaa gcagccaatg | 1440 |
| aagtcggcgc ctggcttatt cattactcga ctgattacgc cttccctgga atggcgata | 1500 |
| tgccatggcg ggagacggat gcaaccgcac cactaaatgt ttacggtgaa accaagttag | 1560 |
| ccggagaaaa agcgttacag gaatattgcg caaagcatct tattttccgg accagctggg | 1620 |
| tctatgcagg aaaaggaaat aacttcgcca aaacgatgtt acgtctggca aaagagcgtg | 1680 |
| aagaattagc ggttattaat gatcagtttg gtgcgccaac aggtgctgaa ctgctggctg | 1740 |
| attgtacagc acatgccatt cgtgtcgcac tgaataaacc agaagtcgca ggcttgtacc | 1800 |
| atctggtagc cagtggtacc acaacctggc acgattatgc tgcgctggtt tttgaagagg | 1860 |
| cacgcaaagc aggtattccc cttgcactca acaagctcaa cgcagtacca acaacagcct | 1920 |
| atcctacacc agctcgtcgt ccgcataact ctcgccttaa tacagaaaaa tttcagcaga | 1980 |
| aatttgcgct tgttttgcct gattggcagg ttggcgtgaa acgaatgctc aacgaattat | 2040 |
| ttacgactac agcaatttaa tagttttttgc atcttgttcg tgatggtgga gcaagatgaa | 2100 |
| ttaaaaggaa tgatgaaatg aaaacgcgta aggtattat tttagctggt ggttcgggta | 2160 |
| ctcgtctta tcctgtaact atggctgtca gtaaacagtt gttaccgatt tatgataaac | 2220 |
| cgatgatcta ttacccgttg tctacactga tgttagcggg tcttcgcgat attctgatta | 2280 |
| ttagtacgcc acaggatact cctcgttttc aacaactgct gggtgacggg agccagtggg | 2340 |
| ggctaaatct tcagtacaaa gtgcaaccga gtccagatgg tcttgcgcag gcatttatca | 2400 |
| tcggtgaaga gtttatcggt ggtgatgatt gtgctttggt tctaggtgat aatatcttt | 2460 |
| acggtcacga tctgccgaag ttaatggatg tcgctgttaa caagaaagt ggtgcaacgg | 2520 |
| tatttgccta tcacgttaat gatcctgaac gctacggtgt cgttgagttt gataaaacg | 2580 |
| gtacggcgat cagcctggaa gaaaaaccgc tacaaccaaa agtaattat gcggtaaccg | 2640 |
| ggcttatttt ttatgataac tacgttgtcg aaatggcgaa aaatcttaag ccttctgccc | 2700 |
| gcggtgaact ggaaattacc gatattaacc gtatttatat ggaacagggg cgtttatccg | 2760 |

```
ttgccatgat gggacgtggt tatgcatggc tggacacggg gacacatcaa agtcttattg   2820
aggcaagcaa ttttatcgca acaatagaag aacgtcaggg gctgaaagtt tcctgcccgg   2880
aagaaattgc ttaccgtaaa gggtttatcg atgctgagca ggtgaaagta ttagctgaac   2940
cgttgaagaa aaatgcttat ggtcagtatc tgctgaaaat gattaaaggt tattaataaa   3000
atgaacgtaa ttaaaacaga aattccagat gtactgattt ttgaaccgaa agttttggt    3060 gatgagcgtg gtttctttat ggaaagcttt aatcagaaag ttttgaaga gctgtaggg    3120 cggaaggttg aatttgttca ggataatcat tctaaatcat ctaagggtgt gttacgcgga   3180
ctgcactatc agctggaacc ctatgctcaa ggtaaattag ttcgttgtgt ggtcggtgaa   3240
gtatttgatg tagcagttga tattcgtaaa tcgtcaccta catttgggaa atgggttggg   3300
gtgaatttgt ctgctgagaa taagcgtcag ttgtggatcc ctgaggggtt tgcgcatggt   3360 ttttggtgt taagcgagat agcagagttt gtttataaga cgacaaatta ttatcatcct    3420
gaatcagaag gttgcataaa atgggatgat ctttttttga tgattgattg ccaaataaa    3480 ccgatagcaa tctcagaaaa agataaaaaa ggctcatcaa ttttgaggct aaatgactat   3540
tgatgttgaa aaaaaaactt caaaaaataa aggaatatca ttcagtattg gagttggcaa   3600
taattcaggg tgcgaatgcc atatttcctg tgttggtatt cccattttt cttattacct    3660 taggggaaaa catcttttca gtattgctg ttggtgaagt actagcacta tatgtgctta    3720
tattttcgct atacagtttt gatattataa gtgtgcagaa ggtaatttca gtgtgacaa    3780 aagatgaaat atttaaagtt tacattctga cactaatctg taggttgtgt ttatttgtta   3840
tttcaggaat atgtctttta tttataacgt atttaattaa taaacatta agtgtatact    3900 tgggattgtt tttattgtac ccagtaggga tgatattgca atctaattat ttttttcagg   3960
ctacgaataa caataggcca ttggctgtt ttgtactaat tgctcgtggt atgtcattat    4020
gtcttattta tttttataat ggaccagcag gctatttaac aagttattat tatgtcattt    4080
gtgtgtctgg ttcgtatttt ttatctggcg tgctatcgct tatatatata tattatcaaa    4140
ataagactaa taaagctaaa attcaatggg cggaaatttt agaatatata tgcacaggtt    4200
atcatctgtt tattgctaat atatttgtta ttctatacag aaatagtaat attattattc   4260
ttggcactct tgcttcgcct gttgcaacgt ctctgtacgc gacggcagag aaaattatta   4320
aatgtattca gtctatagca accccgttaa atcaatacta tttcacgagg ttgataaagc   4380
aacatgaatt gaaattagaa ccatacaaag ttggagaata taaaagcctg ctatatgcaa   4440
gcacaaatat tcagctaaag ttcatggttt tcattgtcct gagttagggg ggggtgggta   4500
ctatattggg atataaggtt caaagtatcg ctgaaattag aagcgcgttc atcccttat    4560 caataatgtc ttttgcaata tttatgggga tatacaattt tatgtttggt tcggttggat   4620
tgtccataag agggtataaa aaagaatttt cttatatagt ggccattacg ggtgtttcaa   4680
ctattatttt atcattatgc ctgagttatt tctttgctga ataggcgct gcaattgctt    4740 atgtatttgc tgagtttatc ttacttattc tcatacttag aatttataaa gtgaaacgat   4800
tataattccc ggtaagaact gatagtgcaa atcatcatg gctatagact gaataaattg     4860
cggggaaaga atgtattaca tcatatttgt gatggtttta ggtttatgga ttattgcatt   4920
caactacgct agagcaaaca agctaagtaa tttggtaatt gtgcttatta ttactacttt    4980
atttattatt aataggcaga atcaagacta tgaagcgtat gttgatatat ttaatgtcaa    5040
tgaactttat gccgagattg gttatcgctg gttaatttat ggtgttaagt atttaggcgg   5100
tacccatgaa gtcataattg gcttgctggg tttattcctt gggaccacat tcctacgatt    5160
```

| | |
|---|---|
| aatacaatac agtaagtata cagcatttgg tttgctgctt tacatgttgt gtccaatgcc | 5220 |
| tattgacatt gttcaaatca ggaatacatt tctttttta tttgtcataa attctcttat | 5280 |
| cgagttagaa aaagagcata aatttaactc tctttgtttt gtctttatgg cacctctttt | 5340 |
| ccatagttta ggcattgttt atgtattggc gtgggtaata atccaatttc gtacctggag | 5400 |
| gggttataat aagttaatgg ttttggact ggtgctgtct tttattgtag tgccactctt | 5460 |
| gattaaaatg ttaattttat tatttaacac taggacgtta catgcatata tagctgatgg | 5520 |
| cattaaggtt cattctctta ttatatgggc aggtccttat cttttgatc ttttctgtt | 5580 |
| atgttacttc agaaaaaaaa tagtaataac tgatttacat actaaacaat ggattgatat | 5640 |
| aatattctcg ctaatgttat ttcttccgt attttcacca ctacttttat atatcgacga | 5700 |
| aataaatagg atttttcgaa atgcgctatt actgaagtat ctggtaatga tgtctatcgc | 5760 |
| acagtattta agtagaccga ccagatatat actttattca tatttactgt tattcacttt | 5820 |
| tgcattatca atatattata cactccaaat cgattatgat tacattgtat ttgggttacc | 5880 |
| atactcatta tgatacttat gaggatatat gttttatttt atctgtgtaa attataataa | 5940 |
| ctctgattat acagaagcat taattaagag cgttattaat caagaaaaag atagctttgt | 6000 |
| aattgttgta gataactgtt ctaatgagca agagctaaaa aagttaaatg atattgagag | 6060 |
| taaatataac gagaaggtca gattaattaa aagtgatgtg aatttgggat attttggcgg | 6120 |
| attgaatctt ggcctaaaag gactaccaag aaatcatcca atagttgttg ggaataatga | 6180 |
| tttggtttat gagagtaatt ttacgcaaat aatatcacag actacatatc cggacgatgc | 6240 |
| tttagttatt gctccaaatg tgattacaaa ggatggttat caccagaacc cacactgccg | 6300 |
| taagcgagta agtaagttta ggaaattttt gtatgatata tatttttcaa attatatcgc | 6360 |
| tgctttagtt ttaacgtggg aagcaggtt tttaaattat ttgaaaggtg aagaaataa | 6420 |
| ttcctttgat cagggtagag gttatataca tatgggtatt ggagcctgtt atgtccttat | 6480 |
| gccttccttc ttcaaatatt ttgatgaatt agataacaaa gttttttat atggtgagga | 6540 |
| agcatatttg gctggccaat taatggaagt aaatgggaag attttctatg agcctgatgc | 6600 |
| tattgtccat catgaagaaa gtgcaacttt ggcgaaagtt gcttctaaaa caaaatatgg | 6660 |
| ctatatgaaa agctcatatt acgactataa aaaatatctg taaaaggtga aaatatgttt | 6720 |
| aagaataaaa cactcgttat cactggtggc actggttctt ttggtaatgc cgtacttaag | 6780 |
| cgttttctag atacagatat tactgaaata cgaatattta gcagggatga aaaaaaacaa | 6840 |
| gatgatatgc ggaaaaaata taataactca aaattaaaat tttatatagg tgatgtgcga | 6900 |
| gactataatt ccgttctaaa tgcaacgcgt ggtgccgatt ttctgtatca tgcagcagcc | 6960 |
| cttaaacaag ttccttcatg tgaatttcac cctatggagg cggttaagac aaatgttctg | 7020 |
| ggtacggaaa atgttctgga ggctgctatt gcgaatggga ttaaacgcgt ggtgtgcttg | 7080 |
| agtaccgata aagccgttta tcctatcaat gcaatgggca tatctaaggc aatgatggaa | 7140 |
| aaagttattg ttgcaaaatc acgtaatctt gacagttcaa aaacagttat ctgtggaact | 7200 |
| cgttatggaa atgtaatggc ttcacgtgga tcggtcatcc cattatttgt tgatctaatc | 7260 |
| aaagctggta aaccattgac cataaccgat cccaatatga ctcgtttcat gatgacgctt | 7320 |
| gaggatgctg tcgatctggt cctttatgct ttcgaacatg gaaataatgg tgacattttc | 7380 |
| gttcagaaag cacctgcggc aacaattcaa acattagcca ttgcacttaa ggaattgcta | 7440 |
| aatgcccatg agcatccaat caatattatt ggaactcgac acggggaaaa actttacgaa | 7500 |

```
gcgttattga gccgagagga aatgattgca gcggaagata tgggtgatta ttatcgtgtt   7560
ccaccagatc tccgcgattt gaactatgga aaatatgtgg aacatggtga ccgtcgtatc   7620
tcggaagtgg aagattataa ttctcataat actgagagat tagatgttga gggaatgaaa   7680
gaattactgc taaaacttcc ttttatccgg gcacttcgtt ctggtgaaga ttatgagttg   7740
gattcataat atgaaaattt tagttactgg cgctgcaggg tttatcggtc gaaatttggt   7800
tttccgcctt aaggaagctg gatataacga acttattgcg atagatcgta actcttcttt   7860
gacggattta gagcagggac ttaagcaggc agatttcatt tttcatcttg ctggagtaaa   7920
tcgtcctgtg aaggagagtg agtttgaaga ggggaattgc gatctaactc aacagattgt   7980
tgatattctg aaaaaaaata ataaagatac tcctatcatg cttagttcat ccatccaagc   8040
tgaatgtgat aacgcttatg gaaagagtaa agcagttgcg gaaaaaatca ttcagcagta   8100
tggggaaacg acaaacgcta atattatat ttatcgcttg ccgaatgtat tcggtaagtg   8160
gtgtcaacca aattataact cctttatagc aactttctgc catcgcattg caaatgatga   8220
agctattaca attaatgatc cttcagcagt tgtaaatttg gtgtatatag atgactttg   8280 ttctgacata ttaaagctat tagaaggagc gaacgaaact ggttacagga catttggtcc   8340
aatttattct gttactgttg gtgaggtggc acaattaatt tatcgattta agaaagtcg   8400 ccaaacatta atcatcgaag atgtaggtaa tggattcact cgagcattgt actcaacatg   8460
gttaagttac ctttctccta acagtttgc gtatacggtt ccttcttata gtgatgacag   8520
aggggtattc tgtgaagtat tgaaaacgaa aaacgcgggc cagttttcgt ttttactgc   8580 gcatccagga attactcggg gggggcatta tcatcattcc aaaaatgaga aattattat   8640 catccgagga agtgcttgtt tcaaatttga aaatattgtc acgggtgaac gatatgaact   8700
taatgtttca tcagatgatt ttaaaattgt tgaaacagtt ccgggatgga cgcatgacat   8760
tactaataat ggctcggatg agctagttgt tatgctttgg gcaaatgaaa tatttaatcg   8820
ttctgaacca gatactatag cgagagtttt atcgtgaaaa aattgaaagt catgtcggtt   8880
gttgggactc gtccagaaat tattcgactc tcgcgtgtcc ttgcaaaatt agatgaatat   8940
tgtgatcacc ttattgttca tactgggcaa aattacgatt atgaattgaa tgaggttttt   9000
ttcaaggatt tgggtgttcg caaacctgat tatttctta atgccgcagg taaaaatgca   9060
gcagagacta ttgacaagt tatcattaaa gttgatgagg tctttgaaca ggaaaaacca   9120
gaagccatgt tagttcttgg cgatactaac tcctgtattt cagcaatacc agcaaagcgt   9180
cgaagaattc cgattttcca tatggaggct gggaatcgtt gttttgatca acgcgtaccg   9240
gaagaaacta acagaaaaat agttgaccac accgctgata tcaatatgac atatagtgat   9300
atcgcgcgtg aatatctttt ggctgaaggt gtaccagccg ataggattat taaaaccggt   9360
agcccaatgt ttgaagtact cactcattat atgtcgcaga ttgatggttc cgatgtactt   9420
tctcgcctga atttaacacc tgggaatttc tttgtggtaa gtgccacag agaagaaaat   9480 gttgataccc ctaaacagct tgcgaaactg gcaaatatac ttaataccgt ggctgaaaaa   9540
tatgatatcc cggtagttgt ttctactcat ccgcgcactc gtaaccgcat caacgaaaac   9600
ggtattcaat ttcataaaaa tatcttgcta cttaagccat taggatttca cgattacaac   9660
catctgcaaa aaaatgcacg tgctgtttta tcggatagcg ggactattac agaggagtcc   9720
tccattatga acttccctgc gctcaatata cgagaagcgc acgaacgccc tgaaggcttc   9780
gaagaagggg ctgtaatgat ggttggtctt gagtctgccc gtgtgttaca ggcattagaa   9840
attattgcaa cacagcctcg tggagaagta cgcttacttc gtcaggtcag tgactatagt   9900
```

```
atgccaaatg tttcagataa agttgtgcgt attatccatt catatactga ctacgttaaa   9960
cgggttgtct ggaagcaata ctaatgaaac ttgcattaat cattgatgat tatttgcccc  10020
atagcacacg agttggggct aaaatgtttc atgagttagg cctggaattg ctgagcagag  10080
gccatgatgt aactgtaatt acgcctgaca acacattaca ggcaatctat tctgttagca  10140
tgactgatgg tataaaggtt tggcgtttca aaagtggacc tttaaaggat ataggtaagg  10200
ctaaacgtgc cataaatgaa actcttttat cttttcgtgc atggcacgca ttaaagcatc  10260
tcatccaaca tgatacattt gatggtatcg tttattattc ccctctatt ttttggggag  10320
gcttggttaa aaaaattaaa gagcgatgcc agtgcccaag ctatctggtc ctaagggata  10380
tgttcccaca gtgggtcatt gatgctggta tgataaaagc cggctcgcca attgaaaaat  10440
atttcaggta ttttgaaaaa aaatcatatc aacaggctga ctggattggg ttaatgtctg  10500
ataagaatct tgagatattt cgtcaggcca taaaggtta tccgtgtgaa gttttacgta  10560
attgggcctc aatgactcct gtgtctgccg gcgatgatta tcattcactt cgtcaaaaat  10620
acgctctaaa agataaaatc attttttct atggcggtaa tattgggcat gctcaggata  10680
tggcaaactt aatgcgcctt gcgcgtaata tgatgcgtca tcatgatgct catttcctgt  10740
ttatagggca gggtgatgaa gttgacctga ttaaatctct ttctgcagaa tggaatttaa  10800
ctaatttcac tcatctacct tcagtgaacc aggaagagtt taaattaatt ttatctgaag  10860
ttgatgttgg cctgttctcc ctttcgtctc gccattcttc acataatttc cccggaaaat  10920
tactagggta tatggttcaa tcaatcccga tccttgggag tgtgaatggc ggtaatgatc  10980
taatggatgt aattaataag cacagggctg ggttcattca tgttaatggt gaagatgata  11040
aactgtttga atctgcacaa ttgcttctta gtgattcagt tttaagaaaa cagttaggtc  11100
agaacgccaa tgtgttgtta aagtctcaat tttcggttga atcggcggca catactatcg  11160
aagtccgact ggaggcagga gaatgcgttt agttgatgac aatattatgg atgaactttt  11220
tcgcactgca gcaaattctg aacgtttgcg cgctcattat ttattgcacg catctcatca  11280
ggagaaggtt caacgtttac ttattgcatt tgtacgcgac agctatgttg aaccccattg  11340
gcatgagtta ccgcatcagt gggaaatgtt tgtcgtcatg caagggcaat tagaagtttg  11400
tttgtatgag caaaatggtg agctccaaaa aaagtttgtt gttggagacg gtacgggaat  11460
aagtgtcgtg gaattttccc caggagatat acatagtgtc aaatgcctgt caccaaaagc  11520
ccttatgtta gagataaagg aggggccatt tgacccactg aaagctaagg cttttttctaa  11580
gtggttatag ggcgatacac caccgtttat tcttctatct tattctatac atgctgggtt  11640
accatcttag cttcttcaag ccgcgtaacc ccgcgtgacc accctgaca ggagtaaaca  11700
atgtca                                                              11706
```

<210> SEQ ID NO 6
<211> LENGTH: 14516
<212> TYPE: DNA
<213> ORGANISM: Artificial sequence
<220> FEATURE:
<223> OTHER INFORMATION: Description of sequence: AF078736.1 Escherichia
      coli O111 O antigen gene cluster, partial sequence

<400> SEQUENCE: 6

```
gatctgatgg ccgtagggcg ctacgtgctt tctgctgata tctgggctga gttggaaaaa    60
actgctccag gtgcctgggg acgtattcaa ctgactgatg ctattgcaga gttggctaaa   120
aaacagtctg ttgatgccat gctgatgacc ggcgacagct acgactgcgg taagaagatg   180
```

```
ggctatatgc aggcattcgt taagtatggg ctgcgcaacc ttaaagaagg ggcgaagttc    240
cgtaagagca tcaagaagct actgagtgag tagagattta cacgtctttg tgacgataag    300
ccagaaaaaa tagcggcagt taacatccag gcttctatgc tttaagcaat ggaatgttac    360
tgccgttttt tatgaaaaat gaccaataat aacaagttaa cctaccaagt ttaatctgct    420
ttttgttgga ttttttcttg tttctggtcg catttggtaa dacaattagc gtgagtttta    480
gagagttttg cgggatctcg cggaactgct cacatctttg gcatttagtt agtgcactgg    540
tagctgttaa gccaggggcg gtagcttgcc taattaattt ttaacgtata catttattct    600
tgccgcttat agcaaataaa gtcaatcgga ttaaacttct tttccattag gtaaaagagt    660
gtttgtagtc gctcagggaa attggttttg gtagtagtac ttttcaaatt atccattttc    720
cgatttagat ggcagttgat gttactatgc tgcatacata tcaatgtata ttatttactt    780
ttagaatgtg atatgaaaaa aatagtgatc ataggcaatg tagcgtcaat gatgttaagg    840
ttcaggaaag aattaatcat gaatttagtg aggcaaggtg ataatgtata ttgtctagca    900
aatgattttt ccactgaaga tcttaaagta ctttcgtcat ggggcgttaa ggggggttaaa    960 ttctctctta actcaagggg tattaatcct tttaaggata taattgctgt ttatgaacta    1020
aaaaaaattc ttaaggatat ttccccagat attgtatttt catattttgt aaagccagta    1080
atatttggaa ctattgcttc aaagttgtca aaagtgccaa ggattgttgg aatgattgaa    1140
ggtctaggta atgccttcac ttattataag ggaaagcaga ccacaaaaac taaaatgata    1200
aagtggatac aaattctttt atataagtta gcattaccga tgcttgatga tttgattcta    1260
ttaaatcatg atgataaaaa agatttaatc gatcagtata atattaaagc taaggtaaca    1320
gtgttaggtg ggattggatt ggatcttaat gagttttcat ataaagagcc accgaaagag    1380 aaaattaccct ttattttta agcaaggtta ttaagagaga aagggatatt tgagtttatt    1440
gaagccgcaa agttcgttaa gacaacttat ccaagttctg aatttgtaat tttaggaggt    1500
tttgagagta ataatccttt ctcattacaa aaaaatgaaa ttgaatcgct aagaaaagaa    1560
catgatctta tttatcctgg tcatgtggaa aatgttcaag attggttaga gaaaagttct    1620 gttttttgttt tacctacatc atatcgagaa ggcgtaccaa gggtgatcca agaagctatg    1680
gctattggta gacctgtaat aacaactaat gtacctgggt gtagggatat aataaatgat    1740
ggggtcaatg gctttttgat acctccattt gaaattaatt tactggcaga aaaaatgaaa    1800
tattttattg agaataaaga taaagtactc gaaatggggc ttgctggaag gaagtttgca    1860
gaaaaaaact ttgatgcttt tgaaaaaaat aatagactag catcaataat aaaatcaaat    1920
aatgattttt gacttgagca gaaattattt atatttcaat ctgaaaaata aaggctgtta    1980
ttatgaataa agtggcatta attactggta tcactgggca agatggctcc tatttggcag    2040
aattattgtt agaaaaaggt tatgaagttc atggtattaa acgccgtgca tcttcattta    2100
atactgagcg agtggatcac atctatcagg attcacattt agctaatcct aaactttttc    2160
tacactatgg cgatttgaca gatacttcca atctgacccg tattttaaaa gaagttcaac    2220
cagatgaagt ttacaatttg ggggcgatga gccatagtagc ggtatcattt gagtcaccag    2280
aatacactgc tgatgttgat gcgataggaa cattgcgtct tcttgaagct atcaggatat    2340
tggggctgga aaaaaagaca aaatttttat caggcttcaac ttcagagctt tatggttttgg    2400 ttcaagaaat tccacaaaaa gagactacgc catttttatcc acgttcgcct tatgctgttg    2460
caaaattata tgcctattgg atcactgtta attatcgtga gtcttatggt atgtttgcct    2520
```

-continued

```
gcaatggtat tctctttaac cacgaatcac ctcgccgtgg cgagaccttt gttactcgta    2580
aaataacacg cgggatagca aatattgctc aaggtcttga taaatgctta tacttgggaa    2640
atatggattc tctgcgtgat tggggacatg ctaaggatta tgtcaaaatg caatggatga    2700
tgctgcagca agaaactcca gaagattttg taattgctac aggaattcaa tattctgtcc    2760
gtgagtttgt cacaatggcg gcagagcaag taggcataga gttagcattt gaaggtgagg    2820
gagtaaatga aaaaggtgtt gttgtttcgg tcaatggcac tgatgctaaa gctgtaaacc    2880
cgggcgatgt aattatatct gtagatccaa ggtattttag gcctgcagaa gttgaaacct    2940
tgcttggcga tcctactaat gcgcataaaa aattaggatg gagccctgaa attacattgc    3000
gtgaaatggt aaagaaatg gtttccagcg atttagcaat agcgaaaaag aacgtcttgc    3060
tgaaagctaa taacattgcc actaatattc cgcaagaata aaaaagataa tacattaaat    3120
aattaaaaat ggtgctagat ttattagtac cattattttt ttttgggtga ctaatgttta    3180
ttacatcaga taaatttaga gaaattatca agttagttcc attagtatca attgatctgc    3240
taattgaaaa cgagaatggt gaatatttat ttggtcttag gaataatcga ccggccaaaa    3300 attattttt tgttccaggt ggtaggattc gcaaaaatga atctattaaa aatgcttttta   3360 aaagaatatc atctatggaa ttaggtaaag agtatgtgat ttcaggaagt gttttaatg     3420 gtgtatggga acatttctat gatgatggtt ttttttctga aggcgaggca acacattata    3480
tagtgctttg ttacacactg aaagttctta aaagtgaatt gaatctccca gatgatcaac    3540
atcgtgaata ccctttggcta actaaacacc aaataaatgc taaacaagat gttcataact    3600
attcaaaaaa ttatttttg taattttat taaaattaa tatgcgagag aattgtatgt       3660
ctcaatgtct ttaccctgta attattgccg gaggaaccgg aagccgtcta tggccgttgt    3720
ctcgagtatt atacectaaa caattttaa atttagttgg ggattctaca atgttgcaaa     3780
caacaattac gcgtttggat ggcatcgaat gcgaaaatcc aattgttatc tgcaatgaag    3840
atcaccgatt tattgtagca gagcaattac gacagattgg taagctaacc aagaatatta    3900
tacttgagcc gaaaggccgt aatactgcac ctgccatagc tttagctgct tttatcgctc    3960
agaagaataa tcctaatgac gacccttat tattagtact tgcggcagac cactctataa     4020
ataatgaaaa agcatttcga gagtcaataa taaaagctat gccgtatgca acttctggga    4080
agttagtaac atttggaatt attccggaca cggcaaatac tggttatgga tatattaaga    4140
gaagttcttc agctgatcct aataaagaat tcccagcata taatgttgcg gagtttgtag    4200
aaaaaccaga tgttaaaaca gcacaggaat atatttcgag tgggaattat tactggaata    4260
gcggaatgtt tttatttcgc gccagtaaat atcttgatga actacggaaa tttagaccag    4320
atatttatca tagctgtgaa tgtgcaaccg ctacagcaaa tatagatatg gactttgtcc    4380
gaattaacga ggctgagttt attaattgtc ctgaagagtc tatcgattat gctgtgatgg    4440
aaaaaacaaa agacgctgta gttcttccga tagatattgg ctggaatgac gtgggttctt    4500
ggtcatcact ttgggatata agccaaaagg attgccatgg taatgtgtgc catggggatg    4560
tgctcaatca tgatggagaa aatagtttta tttactctga gtcaagtctg gttgcgacag    4620
tcggagtaag taatttagta attgtccaaa ccaaggatgc tgtactggtt gcggaccgtg    4680
ataaagtcca aaatgttaaa aacatagttg acgatctaaa aaagagaaaa cgtgctgaat    4740
actacatgca tcgtgcagtt tttcgccctt ggggtaaatt cgatgcaata gaccaaggcg    4800
atagatatag agtaaaaaaa ataatagtta accaggaga agggttagat ttaaggatgc     4860
atcatcatag ggcagagcat tggattgttg tatccggtac tgctaaagtt tcactaggta    4920
```

```
gtgaagttaa actattagtt tctaatgagt ctatatatat ccctcaggga gcaaaatata    4980
gtcttgagaa tccaggcgta ataccttttgc atctaattga agtaagttct ggtgattacc    5040
ttgaatcaga tgatatagtg cgttttactg acagatataa cagtaaacaa ttcctaaagc    5100
gagattgata aatatgaata aaataacttg cttcaaagca tatgatatac gtgggcgtct    5160
tggtgctgaa ttgaatgatg aaatagcata tagaattggt cgcgcttatg gtgagttttt    5220
taaacctcaa actgtagttg tgggaggaga tgctcgctta acaagtgaga gtttaaagaa    5280
atcactctca aatgggctat gtgatgcagg cgtaaatgtc ttagatcttg aatgtgtgg    5340 tactgaagag atatatttt ccacttggta tttaggaatt gatggtggaa tcgaggtaac    5400
tgcaagccat aatccaattg attataatgg aatgaaatta gtaaccaaag gtgctcgacc    5460
aatcagcagt gacacaggtc tcaaagatat acaacaatta gtagagagta ataatttga    5520 agagctcaac ctagaaaaaa aagggaatat taccaaatat tccacccgag atgcctacat    5580
aaatcatttg atgggctatg ctaatctgca aaaaataaaa aaaatcaaaa tagttgtgaa    5640
ttctgggaat ggtgcagctg gtcctgttat tgatgctatt gaggaatgct ttttacggaa    5700
caatattccg attcagtttg taaaaataaa taatacaccc gatggtaatt ttccacatgg    5760
tatccctaat ccattactac ctgagtgcag agaagatacc agcagtgcgg ttataagaca    5820
tagtgctgat tttggtattg catttgatgg tgatttgat aggtgttttt tctttgatga    5880
aaatggacaa tttattgaag gatactacat tgttggttta ttagcggaag tttttttagg    5940
gaaatatcca aacgcaaaaa tcattcatga tcctcgcctt atatggaata ctattgatat    6000
cgtagaaagt catggtggta tacctataat gactaaaacc ggtcatgctt acattaagca    6060
aagaatgcgt gaagaggatg ccgtatatgg cggcgaaatg agtgcgcatc attattttaa    6120
agattttgca tactgcgata gtggaatgat tccttggatt ttaatttgtg aacttttgag    6180
tctgacaaat aaaaaattag gtgaactggt ttgtggttgt ataaacgact ggccggcaag    6240
tggagaaata aactgtacac tagacaatcc gcaaaatgaa atagataaat tatttaatcg    6300
ttacaaagat agtgccttag ctgttgatta cactgatgga ttaactatgg agttctctga    6360
ttggcgtttt aatgttagat gctcaaatac agaacctgta gtacgattga atgtagaatc    6420
taggaataat gctattctta tgcaggaaaa aacagaagaa attctgaatt ttatatcaaa    6480
ataaatttgc acctgagttc ataatgggaa caagaaatat atgaaagtac ttctgactgg    6540
ctcaactggc atggttggta agaatatatt agagcatgat agtgcaagta aatataatat    6600
acttactcca accagctctg atttgaattt attagataaa aatgaaatag aaaaattcat    6660
gcttatcaac atgccagact gtattataca tgcagcggga ttagttggag gcattcatgc    6720
aaatataagc aggccgtttg attttctgga aaaaaatttg cagatgggtt taaatttagt    6780
ttccgtcgca aaaaaactag gtatcaagaa agtgcttaac ttgggtagtt catgcatgta    6840
ccccaaaaac tttgaagagg ctattcctga gaaagctctg ttaactggtg agctagaaga    6900
aactaatgag ggatatgcta ttgcgaaaat tgctgtagca aaagcatgcg aatatatatc    6960
aagagaaaac tctaattatt tttataaaac aattatccca tgtaatttat atgggaaata    7020
tgataaattt gatgataact cgtcacatat gattccggca gttataaaaa aaatccatca    7080
tgcgaaaatt aataatgtcc cagagatcga aatttggggg gatggtaatt cgcgccgtga    7140
gtttatgtat gcagaagatt tagctgatct tattttttat gttattccta aaatagaatt    7200
catgcctaat atggtaaatg ctggtttagg ttacgattat tcaattaatg actattataa    7260
```

```
gataattgca gaagaaattg gttatactgg gagttttttct catgatttaa caaaaccaac    7320
aggaatgaaa cggaagctag tagatatttc attgcttaat aaaattggtt ggtcaagtca    7380
ctttgaactc agagatggca tcagaaagac ctataattat tacttggaga atcaaaataa    7440
atgattacat acccacttgc tagtaatact tgggatgaat atgagtatgc agcaatacag    7500
tcagtaattg actcaaaaat gtttaccatg ggtaaaaagg ttgagttata tgagaaaaat    7560
tttgctgatt tgtttggtag caaatatgcc gtaatggtta gctctggttc tacagctaat    7620
ctgttaatga ttgctgccct tttcttcact aataaaccaa aacttaaaag aggtgatgaa    7680
ataatagtac ctgcagtgtc atggtctacg acatattacc ctctgcaaca gtatggctta    7740
aaggtgaagt ttgtcgatat caataaagaa actttaaata ttgatatcga tagtttgaaa    7800 aatgctatt cagataaaac aaaagcaata ttgacagtaa atttattagg taatcctaat    7860
gattttgcaa aaataaatga gataataaat aatagggata ttatcttact agaagataac    7920
tgtgagtcga tgggcgcggt cttcaaaaat aagcaggcag gcacattcgg agttatgggt    7980
acctttagtt cttttactc tcatcatata gctacaatgg aaggggctg cgtagttact     8040 gatgatgaag agctgtatca tgtattgttg tgccttcgag ctcatggttg gacaagaaat    8100
ttaccaaaag agaatatggt tacaggcact aagagtgatg atattttcga agagtcgttt    8160
aagtttgttt taccaggata caatgttcgc ccacttgaaa tgagtggtgc tattgggata    8220
gagcaactta aaaagttacc aggttttata tccaccagac gttccaatgc acaatatttt    8280
gtagataaat ttaaagatca tccattcctt gatatacaaa aagaagttgg tgaaagtagc    8340
tggtttggtt tttccttcgt tataaaggag ggagctgcta ttgagaggaa gagtttagta    8400
aataatctga tctcagcagg cattgaatgc cgaccaattg ttactgggaa ttttctcaaa    8460
aatgaacgtg ttttgagtta ttttgattac tctgtacatg atacgtagc aaatgccgaa     8520 tatatagata agaatggttt ttttgtcgga aaccaccaga tacctttgtt taatgaaata    8580
gattatctac gaaaagtatt aaaataacta acgaggcact ctatttcgaa tagagtgcct    8640
ttaagatggt attaacagtg aaaaaaattt tagcgtttgg ctattctaaa gtactaccac    8700
cggttattga acagtttgtc aatccaattt gcatcttcat tatcacacca ctaatactca    8760
accacctggg taagcaaagc tatggtaatt ggattttatt aattactatt gtatcttttt    8820
ctcagttaat atgtggagga tgttccgcat ggattgcaaa atcattgca gaacagagaa     8880 ttcttagtga tttatcaaaa aaaaatgctt tacgtcaaat ttcctataat ttttcaattg    8940
ttattatcgc atttgcggta ttgatttctt ttcttatatt aagtatttgt ttcttcgatg    9000
ttgcgaggaa taattcttca ttcttattcg cgattattat ttgtggtttt tttcaggaag    9060
ttgataattt atttagtggt gcgctaaaag gttttgaaaa atttaatgta tcatgttttt    9120
ttgaagtaat tacaagagtg ctctgggctt ctatagtaat atatggcatt tacggaaatg    9180
cactcttata ttttacatgt ttagccttta ccattaaagg tatgctaaaa tatattcttg    9240
tatgtctgaa tattaccggt tgtttcatca atcctaattt taatagagtt gggattgtta    9300
atttgttaaa tgagtcaaaa tggatgtttc ttcaattaac tggtggcgtc tcacttagtt    9360
tgtttgatag gctcgtaata ccattgattt tatctgtcag taaactggct tcttatgtcc    9420
cttgccttca actagctcaa ttgatgttca ctctttctgc gtctgcaaat caaatattac    9480
taccaatgtt tgctagaatg aaagcatcta acacatttcc ctctaattgt ttttttaaaa    9540 ttctgccttgt atcactaatt tctgttttgc cttgtcttgc gttattcttt tttggtcgtg    9600
atatattatc aatatggata aaccctacat ttgcaactga aaattataaa ttaatgcaaa    9660
```

```
ttttagctat aagttacatt ttattgtcaa tgatgacatc ttttcatttc ttgttattag    9720
gaattggtaa atctaagctt gttgcaaatt taaatctggt tgcagggctc gcacttgctg    9780
cttcaacgtt aatcgcagct cattatggcc tttatgcaat atctatggta aaaataatat    9840
atccggcttt tcaattttat tacctttatg tagcttttgt ctattttaat agagcgaaaa    9900
atgtctattg atttactttt ttcaattact gaaatcgcaa ttgttttttc ttgcactatt    9960
tacatattta ctcaatgttt gttaatgcgg aggatctatt tagataaaag tattttaatt   10020
cttttatgct tgctcttttt tttagtaatc attcaacttc ctgagcttaa tgtaaacggt   10080
ttggtcgatt ctttaaagtt atcactgcct ttattgatgg tctttatcgc ttttcaaaaa   10140
ccgaaattat gcttgtgggt tattattgca ttgttgtttt tgaactctgc atttaatttt   10200
ttatatttaa agacattcga taagtttagc tcatttcctt ttacttttt tatattgctg    10260 ttttacttgt ttagattggg aattggtaat ttaccggttt ataaaaataa aaaattttac   10320
gcgttgattt ttctctttat attaatagac ataatgcagt cattgttaat aaattatagg   10380
gggcagattt tatattccgt aatttgcatc ctgatacttg tgtttaaagt taatttaaga   10440
aaaaagattc catactttt tttaatgctg ccagttttat atgtaattat tatggcttat    10500
attggtttta attatttcaa taaaggcgta acttttttg aacctacagc aagtaatatt    10560
gaacgtacgg ggatgatata ttatttggtt tcacagcttg gtgattatat attccatggt   10620
atggggacat taaatttctt aaataacggc ggacaatata agacgttata tggacttcca   10680
tcattaattc ctaatgaccc tcatgatttt ttattacggt tctttataag tattggtgtg   10740
ataggagcat tggtttatca ttctatattt tttgtttttt ttaggagaat atctttctta   10800
ttatatgaga gaaatgctcc tttcattgtt gtaagttgtt tgttactgtt acaagttgtg   10860
ttaatttata cattaaaccc ttttgatgct tttaatcgat tgatttgcgg gcttacagtt   10920
ggagttgttt atggatttgc aaaaattaga taagtatacc tgtaatgaa atttagacgc    10980 tccacttgtt tcaataatca ttgcaactta taattctgaa cttgatatag ctaagtgttt   11040
gcaatcggta actaatcaat cttataagaa tattgaaatc ataataatgg atggaggatc   11100
ttctgataaa acgcttgata ttgcaaaatc gtttaaagac gaccgaataa aaatagtttc   11160
agagaaagat cgtggaattt atgatgcctg gaataaagca gttgatttat ccattggtga   11220
ttgggtagca tttattggtt cagatgatgt ttactatcat acagatgcaa ttgcttcatt   11280
gatgaagggg gttatggtat ctaatggcgc ccctgtggtt tatgggagga cagcgcacga   11340
aggtcccgat aggaacatat ctggattttc aggcagtgaa tggtacaacc taacaggatt   11400
taagtttaat tattacaaat gtaatttacc attgcccatt atgagcgcaa tatattctcg   11460
tgatttcttc agaaacgaac gttttgatat taaattaaaa attgttgctg acgctgattg   11520
gtttctgaga tgtttcatca aatggagtaa agagaagtca ccttattta ttaatgacac    11580 gaccctatt gttagaatgg gatatggtgg ggtttcgact gatatttctt ctcaagttaa    11640
aactacgcta gaaagtttca ttgtacgcaa aaagaataat atatcctgtt taaacataca   11700
gctgattctt agatatgcta aaattctggt gatggtagcg atcaaaaata ttttggcaa    11760 taatgtttat aaattaatgc ataacgggta tcattcccta agaaaatca agaataaaat    11820 atgaagattg tttatataat aaccgggctt acttgtggtg gagccgaaca ccttatgacg   11880
cagttagcag accaaatgtt tatacgcggg catgatgtta atattatttg tctaactggt   11940
atatctgagg taaagccaac acaaaatatt aatattcatt atgttaatat ggataaaaat   12000
```

```
tttagaagct tttttagagc tttatttcaa gtaaaaaaaa taattgtcgc cttaaagcca    12060
gatataatac atagtcatat gtttcatgct aatattttta gtcgttttat taggatgctg    12120
attccagcgg tgccctgat atgtaccgca cacaacaaaa atgaaggtgg caatgcaagg     12180
atgttttgtt atcgactgag tgattttta gcttctatta ctacaaatgt aagtaaagag     12240
gctgttcaag agtttatagc aagaaaggct acacctaaaa ataaaatagt agagattccg    12300
aattttatta atacaaataa atttgatttt gatattaatg tcagaaagaa aacgcgagat    12360
gcttttaatt tgaaagacag tacagcagta ctgctcgcag taggaagact tgttgaagca    12420
aaagactatc cgaacttatt aaatgcaata aatcatttga ttctttcaaa aacatcaaat    12480
tgtaatgatt ttattttgct tattgctggc gatggcgcat taagaaataa attattggat    12540
ttggtttgtc aattgaatct tgtggataaa gttttcttct tggggcaaag aagtgatatt    12600
aaagaattaa tgtgtgctgc agatcttttt gttttgagtt ctgagtggga aggttttggt    12660
ctcgttgttg cagaagctat ggcgtgtgaa cgtcccgttg ttgctaccga ttctggtgga    12720
gttaaagaag tcgttggacc tcataatgat gttatccctg tcagtaatca tattctgttg    12780
gcagagaaaa tcgctgagac acttaaaata gatgataacg caagaaaaat aataggtatg    12840
aaaaatagag aatatattgt ttccaatttt tcaattaaaa cgatagtgag tgagtgggag    12900
cgcttatatt ttaaatattc caagcgtaat aatataattg attgaaaata taagtttgta    12960
ctctggatgc aatagtttct ctatgctgtt tttttactgg ctccgtatt ttacttatag    13020 ctggattttg ttatatatca gtattaatct gtctcaactt catctagact acattcaagc    13080
cgcgcatgcg tcgcgcggtg actacacctg acaggagtat gtaatgtcca agcaacagat    13140
cggcgtcgtc ggtatggcag tgatggggcg caacctggcg ctcaacatcg aaagccgcgg    13200
ttataccgtc tccatcttca accgctcccg cgagaaaact gaagaagttg ttgccgagaa    13260
cccggataag aaactggttc cttattacac ggtgaaagag ttcgtcgagt ctcttgaaac    13320
cccacgtcgt atcctgttaa tggtaaaagc aggggcggga actgatgctg ctatcgattc    13380
cctgaagccg tatctggata aaggcgacat cattattgat ggtggcaaca ccttcttcca    13440
ggacactatc cgtcgtaacc gtgaactgtc cgcggaaggc tttaacttca tcggtaccgg    13500
cgtgtccggc ggtgaagagg gcgccctgaa aggcccatct atcatgccag gtggccagaa    13560
agaagcgtat gagctggttg cgcctatcct gaccaagatt gctgcggttg ctgaagatgg    13620
cgaaccatgt ataacttaca tcggtgctga cggtgcgggt cactacgtga agatggtgca    13680
caacggtatc gaatatggcg atatgcagct gattgctgaa gcctattctc tgcttaaagg    13740
cggccttaat ctgtctaacg aagagctggc aaccactttt accgagtgga atgaaggcga    13800
gctaagtagc tacctgattg acatcaccaa agacatcttc accaaaaaag atgaagaggg    13860
taaatacctg gttgatgtga tcctggacga agctgcgaac aaaggcaccg gtaaatggac    13920
cagccagagc tctctggatc tgggtgaacc gctgtcgctg atcaccgaat ccgtattcgc    13980
tcgctacatc tcttctctga agaccagcg cattgcggca tctaaagtgc tgtctggtcc    14040
gcaggctaaa ctggctggtg ataaagcaga gttcgttgag aaagtccgtc gcgcgctgta    14100
cctgggtaaa atcgtctctt atgcccaagg cttctctcaa ctgcgtgccg cgtctgacga    14160
atacaactgg gatctgaact acggcgaaat cgcgaagatc ttccgcgcgg gctgcatcat    14220
tcgtgcgcag ttcctgcaga aaattactga cgcgtatgct gaaaacaaag gcattgctaa    14280
cctgttgctg gctccgtact tcaaaaatat cgctgatgaa tatcagcaag cgctgcgtga    14340
tgtagtggct tatgctgtgc agaacggtat tccggtaccg accttctctg cagcggtagc    14400
```

```
ctactacgac agctaccgtt ctgcggtact gccggctaat ctgattcagg cacagcgtga      14460
ttacttcggt gcgcacacgt ataaacgcac tgataaagaa ggtgtgttcc acaccg          14516
```

<210> SEQ ID NO 7
<211> LENGTH: 19
<212> TYPE: DNA
<213> ORGANISM: Artificial sequence
<220> FEATURE:
<223> OTHER INFORMATION: Description of sequence: PRIMER FOR
     O103-wbtD850F (forward)

<400> SEQUENCE: 7
gatgaaacaa acggtaaat                                                   19

<210> SEQ ID NO 8
<211> LENGTH: 23
<212> TYPE: DNA
<213> ORGANISM: Artificial sequence
<220> FEATURE:
<223> OTHER INFORMATION: Description of sequence: PRIMER FOR
     O103-wbtD995R (reverse)

<400> SEQUENCE: 8
tttcatattt agctaacaag ttt                                              23

<210> SEQ ID NO 9
<211> LENGTH: 20
<212> TYPE: DNA
<213> ORGANISM: Artificial sequence
<220> FEATURE:
<223> OTHER INFORMATION: Description of sequence: PRIMER FOR
     O121-vioA-257F (forward)

<400> SEQUENCE: 9
caactgcaca ctccttggtc                                                  20

<210> SEQ ID NO 10
<211> LENGTH: 20
<212> TYPE: DNA
<213> ORGANISM: Artificial sequence
<220> FEATURE:
<223> OTHER INFORMATION: Description of sequence: PRIMER FOR
     O121-vioA-354R (reverse)

<400> SEQUENCE: 10
cgcctcttca attcttctcg                                                  20

<210> SEQ ID NO 11
<211> LENGTH: 19
<212> TYPE: DNA
<213> ORGANISM: Artificial sequence
<220> FEATURE:
<223> OTHER INFORMATION: Description of sequence: O26-Vir-Probe

<400> SEQUENCE: 11
cagatattac tgaaatacg                                                   19

<210> SEQ ID NO 12
<211> LENGTH: 19
<212> TYPE: DNA
<213> ORGANISM: Artificial sequence
<220> FEATURE:
<223> OTHER INFORMATION: Description of sequence: O26 AVir Probe

<400> SEQUENCE: 12

```
cagatattgc tgaaatacg                                              19

<210> SEQ ID NO 13
<211> LENGTH: 20
<212> TYPE: DNA
<213> ORGANISM: Artificial sequence
<220> FEATURE:
<223> OTHER INFORMATION: Description of sequence: O111 AVir Probe

<400> SEQUENCE: 13
tggttacagg cactaagagt                                             20

<210> SEQ ID NO 14
<211> LENGTH: 20
<212> TYPE: DNA
<213> ORGANISM: Artificial sequence
<220> FEATURE:
<223> OTHER INFORMATION: Description of sequence: O111 Vir Probe

<400> SEQUENCE: 14
tggttacagg tactaagagt                                             20

<210> SEQ ID NO 15
<211> LENGTH: 18
<212> TYPE: DNA
<213> ORGANISM: Artificial sequence
<220> FEATURE:
<223> OTHER INFORMATION: Description of sequence: O103 AVir Probe

<400> SEQUENCE: 15
attaacctgc atattaaa                                               18

<210> SEQ ID NO 16
<211> LENGTH: 18
<212> TYPE: DNA
<213> ORGANISM: Artificial sequence
<220> FEATURE:
<223> OTHER INFORMATION: Description of sequence: O103 Vir Probe

<400> SEQUENCE: 16
attaacctgt atattaaa                                               18

<210> SEQ ID NO 17
<211> LENGTH: 19
<212> TYPE: DNA
<213> ORGANISM: Artificial sequence
<220> FEATURE:
<223> OTHER INFORMATION: Description of sequence: O121 Vir Probe

<400> SEQUENCE: 17
cgatattgat cccaaaacc                                              19

<210> SEQ ID NO 18
<211> LENGTH: 19
<212> TYPE: DNA
<213> ORGANISM: Artificial sequence
<220> FEATURE:
<223> OTHER INFORMATION: Description of sequence: O121 Vir Probe

<400> SEQUENCE: 18
cgatattgat tccaaaacc                                              19

<210> SEQ ID NO 19
<211> LENGTH: 19
<212> TYPE: DNA
<213> ORGANISM: Artificial sequence
```

```
<220> FEATURE:
<223> OTHER INFORMATION: Description of sequence: 16S RNA-F

<400> SEQUENCE: 19
cctcttgcca tcggatgtg                                                    19

<210> SEQ ID NO 20
<211> LENGTH: 21
<212> TYPE: DNA
<213> ORGANISM: Artificial sequence
<220> FEATURE:
<223> OTHER INFORMATION: Description of sequence: 16S RNA-R

<400> SEQUENCE: 20
ggctggtcat cctctcagac c                                                 21

<210> SEQ ID NO 21
<211> LENGTH: 26
<212> TYPE: DNA
<213> ORGANISM: Artificial sequence
<220> FEATURE:
<223> OTHER INFORMATION: Description of sequence: 16S rRNA Probe

<400> SEQUENCE: 21
gtggggtaac ggctcaccta ggcgac                                            26
```